US011713474B2

(12) United States Patent
Bootsma

(10) Patent No.: US 11,713,474 B2
(45) Date of Patent: Aug. 1, 2023

(54) PROCESSES FOR PRODUCING ONE OR MORE FERMENTATION PRODUCTS IN A SECOND FERMENTATION

(71) Applicant: POET Grain (Octane), LLC, Sioux Falls, SD (US)

(72) Inventor: Jason Bootsma, Wichita, KS (US)

(73) Assignee: POET GRAIN (OCTANE), LLC, Sioux Falls, SD (US)

( * ) Notice: Subject to any disclaimer, the term of this patent is extended or adjusted under 35 U.S.C. 154(b) by 0 days.

(21) Appl. No.: 17/675,928

(22) Filed: Feb. 18, 2022

(65) Prior Publication Data

US 2022/0170054 A1 Jun. 2, 2022

Related U.S. Application Data

(60) Continuation of application No. 16/102,835, filed on Aug. 14, 2018, now Pat. No. 11,254,955, which is a division of application No. 15/604,507, filed on May 24, 2017, now Pat. No. 10,059,966, which is a continuation-in-part of application No. 15/529,025, filed as application No. PCT/US2016/063666 on Nov. 23, 2016, now Pat. No. 11,248,197, which is a continuation-in-part of application No. 15/529,014, filed as application No. PCT/US2016/063657 on Nov. 23, 2016, now Pat. No. 10,837,029.

(60) Provisional application No. 62/324,159, filed on Apr. 18, 2016, provisional application No. 62/260,181, filed on Nov. 25, 2015, provisional application No. 62/260,181, filed on Nov. 25, 2015.

(51) Int. Cl.
| | | |
|---|---|---|
| C12P 7/10 | (2006.01) | |
| C12P 7/14 | (2006.01) | |
| C12P 19/14 | (2006.01) | |
| C12P 19/02 | (2006.01) | |
| C12M 1/00 | (2006.01) | |
| C12P 7/6409 | (2022.01) | |
| C12N 9/42 | (2006.01) | |

(52) U.S. Cl.
CPC .............. *C12P 7/10* (2013.01); *C12M 47/10* (2013.01); *C12P 7/14* (2013.01); *C12P 7/6409* (2013.01); *C12P 19/02* (2013.01); *C12P 19/14* (2013.01); *C12M 45/04* (2013.01); *C12M 47/06* (2013.01); *C12N 9/2437* (2013.01); *C12P 2201/00* (2013.01)

(58) Field of Classification Search
None
See application file for complete search history.

(56) References Cited

U.S. PATENT DOCUMENTS

| | | |
|---|---|---|
| 2,446,913 A | 8/1948 | Erlich |
| 2,478,937 A | 8/1949 | Niethamer |
| 2,698,826 A | 1/1955 | Peltzer |
| 3,538,551 A | 11/1970 | Joa |
| 3,761,027 A | 9/1973 | Mendoza |
| 4,056,636 A | 11/1977 | Muller |
| 4,361,651 A | 11/1982 | Keim |
| 4,565,330 A | 1/1986 | Katoh |
| 5,195,684 A | 3/1993 | Radzins |
| 5,250,182 A | 10/1993 | Bento et al. |
| 5,662,810 A | 9/1997 | Willgohs |
| 5,795,477 A | 8/1998 | Herman et al. |
| 6,106,673 A | 8/2000 | Walker |
| 6,117,321 A | 9/2000 | Johnston |
| 6,230,995 B1 | 5/2001 | Niemi et al. |
| 6,475,132 B2 | 11/2002 | Zettier |
| 6,509,180 B1 | 1/2003 | Verser et al. |
| 6,962,722 B2 | 11/2005 | Dawley et al. |
| 7,083,954 B2 | 8/2006 | Jakel et al. |
| 7,101,691 B2 | 9/2006 | Kinley et al. |
| 7,300,680 B2 | 11/2007 | Prevost et al. |
| 7,384,010 B2 | 6/2008 | Horigane et al. |
| 7,497,955 B2 | 3/2009 | Scheimann et al. |
| 7,507,562 B2 | 3/2009 | Verser et al. |
| 7,572,353 B1 | 8/2009 | Griend |
| 7,601,858 B2 | 10/2009 | Cantrell et al. |
| 7,608,729 B2 | 10/2009 | Winsness et al. |

(Continued)

FOREIGN PATENT DOCUMENTS

| | | |
|---|---|---|
| AU | 199528333 A | 2/1996 |
| WO | 2005029974 A1 | 4/2005 |

(Continued)

OTHER PUBLICATIONS

"Flottweg Separation Technology," Web page <https://www.flottweg.com/fileadmin/user_upload/data/pdf-downloads/Sedicanter-EN.pdf>, 12 pages, Aug. 10, 2016, retrieved from Internet Archive Wayback Machine<https://web.archive.org/web/20160810032610/https://www.flottweg.com/fileadmin/user_upload/data/pdf-downloads/Sedicanter-EN.pdf> on Jul. 12, 2022.

Pleasant Hill Grain, "ABC Hansen Disc Mill", website catalog pp. 1-8, retrieved on Aug. 9, 2015, (8 pages).

Rausch et al., "Particle Size Distributions of Ground Corn and DDGS from Dry Grind Processing", Transactions of the ASAE, vol. 48, No. 1, pp. 273-277, 2005, (5 pages).

"Disc Mill DM 400-Retsch-Powerful grinding and robust design", retrieved from 'https://www.retsch.com/products/milling/disc-mills/dm-400/function-features/', on Aug. 19, 2015, (2 pages).

(Continued)

*Primary Examiner* — Christian L Fronda
(74) *Attorney, Agent, or Firm* — Kagan Binder, PLLC

(57) ABSTRACT

Processes and systems for recovering products from a fermentation mash. In some examples, a process for recovering products from a fermentation mash can include processing a ground corn product to produce a fermentation mash that can include ethanol. At least a portion of the ethanol can be separated from the fermentation mash to produce a whole stillage. The whole stillage can be separated to produce a fiber rich product and a filtrate. The fiber rich product can be hydrolyzed to produce a saccharification mash. The saccharification mash can be processed to produce additional ethanol and a stillage protein product.

20 Claims, 8 Drawing Sheets

(56) References Cited

U.S. PATENT DOCUMENTS

| | | |
|---|---|---|
| 7,699,255 B2 | 4/2010 | Kapper |
| 7,829,680 B1 | 11/2010 | Sander et al. |
| 7,842,484 B2 | 11/2010 | Lewis |
| 7,857,608 B2 | 12/2010 | Fabbricante et al. |
| 7,858,140 B2 | 12/2010 | Paustian et al. |
| 7,886,996 B2 | 2/2011 | Horigane et al. |
| 7,888,082 B2 | 2/2011 | Verser et al. |
| 7,915,458 B2 | 3/2011 | Bruckmayer |
| 7,919,289 B2 | 4/2011 | Lewis |
| 7,935,370 B1 | 5/2011 | Prevost et al. |
| 7,954,734 B2 | 6/2011 | Hata |
| 8,017,365 B1 | 9/2011 | Rein et al. |
| 8,093,023 B1 | 1/2012 | Prevost et al. |
| 8,103,385 B2 | 1/2012 | Macharia et al. |
| 8,126,606 B2 | 2/2012 | Hung |
| 8,168,037 B2 | 5/2012 | Winsness |
| 8,192,627 B2 | 6/2012 | Gallop et al. |
| 8,236,086 B2 | 8/2012 | Janssen et al. |
| 8,236,977 B2 | 8/2012 | Woods et al. |
| 8,257,951 B2 | 9/2012 | Prevost et al. |
| 8,449,728 B2 | 5/2013 | Redford |
| 8,454,802 B2 | 6/2013 | Redford |
| 8,524,473 B2 | 9/2013 | Hammond et al. |
| 8,563,282 B2 | 10/2013 | Galvez, III et al. |
| 8,597,917 B2 | 12/2013 | Medoff et al. |
| 8,603,786 B2 | 12/2013 | Redford |
| 8,679,353 B2 | 3/2014 | Winsness |
| 8,702,819 B2 | 4/2014 | Bootsma |
| 8,722,372 B2 | 5/2014 | Kiuchi et al. |
| 8,722,911 B2 | 5/2014 | Bleyer et al. |
| 8,735,544 B1 | 5/2014 | Prevost et al. |
| 8,748,141 B2 | 6/2014 | Lewis et al. |
| 8,778,433 B2 | 7/2014 | Lee |
| 8,813,973 B2 | 8/2014 | Lee et al. |
| 8,927,239 B2 | 1/2015 | Allen et al. |
| 8,956,460 B2 | 2/2015 | Ahmed et al. |
| 8,962,059 B1 | 2/2015 | Froderman et al. |
| 8,986,551 B2 | 3/2015 | Kohl et al. |
| 9,012,191 B2 | 4/2015 | Lee |
| 9,012,668 B2 | 4/2015 | Winsness |
| 9,029,126 B2 | 5/2015 | Bleyer et al. |
| 9,040,270 B2 | 5/2015 | Prevost et al. |
| 9,061,987 B2 | 6/2015 | Bootsma |
| 9,108,140 B2 | 8/2015 | Winsness |
| 9,114,114 B2 | 8/2015 | Anderson et al. |
| 9,150,790 B2 | 10/2015 | Thorn et al. |
| 9,169,498 B2 | 10/2015 | Woods et al. |
| 9,212,334 B2 | 12/2015 | Cantrell et al. |
| 9,320,990 B2 | 4/2016 | Winsness |
| 9,328,311 B2 | 5/2016 | Jenkins et al. |
| 9,340,767 B2 | 5/2016 | Narendranath |
| 9,353,332 B2 | 5/2016 | Lewis et al. |
| 9,375,731 B2 | 6/2016 | Dieker et al. |
| 9,376,504 B2 | 6/2016 | Dieker et al. |
| 9,388,475 B2 | 7/2016 | Lee |
| 9,516,891 B1 | 12/2016 | Roa-Espinosa |
| 9,631,161 B2 | 4/2017 | Sungail et al. |
| 9,695,381 B2 | 7/2017 | Lee |
| 9,714,267 B2 | 7/2017 | Emanuele et al. |
| 9,718,006 B2 | 8/2017 | Lee et al. |
| 9,730,463 B1 | 8/2017 | Roa-Espinosa |
| 9,745,540 B2 | 8/2017 | Sungail et al. |
| 9,896,643 B2 | 2/2018 | Redford |
| 9,963,671 B2 | 5/2018 | Williams et al. |
| 10,059,966 B2 | 8/2018 | Bootsma |
| 10,093,891 B2 | 10/2018 | Kohl et al. |
| 10,113,007 B2 | 10/2018 | Kohl |
| 10,214,559 B2 | 2/2019 | Modinger et al. |
| 10,226,774 B2 | 3/2019 | Franko |
| 10,260,031 B2 | 4/2019 | Gallop et al. |
| 10,400,201 B2 | 9/2019 | Yu |
| 10,449,469 B2 | 10/2019 | Lewis |
| 10,465,152 B2 | 11/2019 | Bootsma |
| 10,683,479 B2 | 6/2020 | Lucas |
| 10,745,643 B2 | 8/2020 | Gallop et al. |
| 10,774,303 B2 | 9/2020 | Dieker et al. |
| 10,837,029 B2 | 11/2020 | Bootsma et al. |
| 11,028,378 B2 | 6/2021 | Jump et al. |
| 11,078,500 B2 | 8/2021 | Hansen et al. |
| 11,104,873 B2 | 8/2021 | Bootsma |
| 11,166,478 B2 | 11/2021 | Lee |
| 11,248,197 B2 * | 2/2022 | Bootsma ............... B01D 3/002 |
| 11,254,955 B2 * | 2/2022 | Bootsma .................. C12P 7/14 |
| 11,273,455 B2 | 3/2022 | Xu |
| 11,286,509 B2 * | 3/2022 | Bootsma ............... C12P 7/6409 |
| 11,337,442 B2 | 5/2022 | Lecocq et al. |
| 2004/0087808 A1 | 5/2004 | Prevost et al. |
| 2004/0192896 A1 | 9/2004 | Finch |
| 2004/0234649 A1 | 11/2004 | Lewis et al. |
| 2005/0233030 A1 | 10/2005 | Lewis et al. |
| 2005/0239181 A1 | 10/2005 | Lewis et al. |
| 2006/0194296 A1 | 8/2006 | Hammond et al. |
| 2007/0031953 A1 | 2/2007 | Dunson, Jr. et al. |
| 2007/0036881 A1 | 2/2007 | Griffith |
| 2007/0141691 A1 | 6/2007 | Hirl |
| 2007/0148318 A1 | 6/2007 | Rubio et al. |
| 2007/0190626 A1 | 8/2007 | Wilkening et al. |
| 2007/0238691 A1 | 10/2007 | Thompson et al. |
| 2007/0254089 A1 | 11/2007 | Hickey et al. |
| 2008/0009048 A1 | 1/2008 | Bhargava et al. |
| 2008/0110577 A1 | 5/2008 | Winsness |
| 2008/0193991 A1 | 8/2008 | Allen et al. |
| 2008/0277264 A1 | 11/2008 | Sprague |
| 2009/0093027 A1 | 4/2009 | Balan et al. |
| 2009/0176289 A1 | 7/2009 | Friedmann |
| 2009/0250412 A1 | 10/2009 | Winsness et al. |
| 2009/0269817 A1 | 10/2009 | Lantero |
| 2009/0311397 A1 | 12/2009 | Whalen et al. |
| 2010/0055741 A1 * | 3/2010 | Galvez, III ............ C12P 19/02 |
| | | 435/162 |
| 2010/0159519 A1 | 6/2010 | Diner et al. |
| 2010/0221804 A1 | 9/2010 | Veit et al. |
| 2010/0281765 A1 | 11/2010 | Schwartz |
| 2011/0003341 A1 | 1/2011 | Nojiri et al. |
| 2011/0086149 A1 | 4/2011 | Bootsma |
| 2011/0142788 A1 | 6/2011 | Sellier et al. |
| 2011/0143411 A1 | 6/2011 | Yuan et al. |
| 2012/0051980 A1 | 3/2012 | Gallop et al. |
| 2012/0064213 A1 | 3/2012 | Lee |
| 2012/0244590 A1 | 9/2012 | Lee |
| 2013/0165678 A1 | 6/2013 | Kohl et al. |
| 2013/0295661 A1 | 11/2013 | Roesch et al. |
| 2014/0024084 A1 | 1/2014 | Galvez, III et al. |
| 2014/0110512 A1 | 4/2014 | Lee |
| 2014/0155639 A1 | 6/2014 | Sticklen et al. |
| 2014/0178946 A1 | 6/2014 | Galvez, III et al. |
| 2014/0242251 A1 * | 8/2014 | Bootsma .................. C12F 3/10 |
| | | 426/624 |
| 2014/0273166 A1 | 9/2014 | Narendranath |
| 2014/0315259 A1 | 10/2014 | Woods et al. |
| 2015/0024451 A1 | 1/2015 | Williams |
| 2015/0037857 A1 | 2/2015 | Redford |
| 2015/0056327 A1 | 2/2015 | Redford |
| 2015/0076078 A1 | 3/2015 | Gallop |
| 2015/0118727 A1 | 4/2015 | Escudero et al. |
| 2015/0147786 A1 | 5/2015 | Clarkson et al. |
| 2015/0152196 A1 | 6/2015 | Phanopoulos et al. |
| 2015/0152372 A1 | 6/2015 | Kohl et al. |
| 2015/0181911 A1 | 7/2015 | Redford |
| 2015/0181912 A1 | 7/2015 | Redford |
| 2015/0182882 A1 | 7/2015 | Gallop et al. |
| 2015/0299645 A1 | 10/2015 | Williams |
| 2016/0024406 A1 | 1/2016 | Javers et al. |
| 2016/0145650 A1 | 5/2016 | Lewis et al. |
| 2016/0222135 A1 | 8/2016 | Lee |
| 2017/0051322 A1 | 2/2017 | Bushong et al. |
| 2017/0107452 A1 | 4/2017 | Dasari et al. |
| 2017/0114293 A1 | 4/2017 | Jakel et al. |
| 2017/0166834 A1 | 6/2017 | Jakel |
| 2017/0166835 A1 | 6/2017 | Jakel |
| 2017/0226165 A1 | 8/2017 | Franko et al. |
| 2017/0253892 A1 | 9/2017 | Bootsma |
| 2017/0268024 A1 | 9/2017 | Bootsma et al. |
| 2018/0016602 A1 | 1/2018 | Franko et al. |

(56) References Cited

U.S. PATENT DOCUMENTS

| | | | |
|---|---|---|---|
| 2018/0126302 A1 | 5/2018 | Gallop | |
| 2018/0242626 A1 | 8/2018 | Froderman et al. | |
| 2018/0355387 A1 | 12/2018 | Javers et al. | |
| 2020/0140899 A1 | 5/2020 | Bootsma | |
| 2021/0214659 A1 | 7/2021 | Bootsma | |
| 2021/0251256 A1 | 8/2021 | Gibbons et al. | |
| 2022/0015381 A1 | 1/2022 | Rindsig et al. | |
| 2022/0142200 A1 | 5/2022 | Gibbons et al. | |

FOREIGN PATENT DOCUMENTS

| | | |
|---|---|---|
| WO | 2017059083 A1 | 4/2017 |
| WO | 2017091760 A1 | 6/2017 |
| WO | 2017091766 A1 | 6/2017 |
| WO | 2018215965 A1 | 11/2018 |
| WO | 2018217202 A1 | 11/2018 |

OTHER PUBLICATIONS

Kotrba, "Ethanol Producers Talk Shop", restreived from 'http://www.ethanolproducer.com/articles/2213/ethanol-producers-talk-shop', dated Aug. 1, 2006, (3 pages).
"Corn Wet Milling Process Description", Fluid Quip-Ethanol Industry, website pp. 1-6, retrieved on Aug. 19, 2015, (6 pages).
International Standard, ISO 13320:2009(E), Particle Size Analysis—Laser Diffraction Methods, pp. 1-58, 2009, (58 pages).
Akinoso et al., "Work Index and Milling Efficiency of Size Reduction of Maize Using Plate Mill", Agricultural Engineering Today, vol. 36, pp. 22-28, 2012, (3 pages) (Abstract Only).
Rosentrater, "Production and use of evolving com-based fuel ethanol coproducts in the U.S", Biofuels—Status and Perspective, Chapter 5, pp. 81-98, 2015, (18 pages).
Olson, "A Lecture on Pressure Screening", Mechanical Engineering Department, University of British Columbia, 2003, (17 pages).
Kim et al., "Process simulation of modified dry grind ethanol plant with recycle of pretreated and enzymatically hydrolyzed distillers' grains", Bioresource Technology, vol. 99, pp. 5177-5192, 2008, (16 pages).
Nouroddini et al., "Stagewise Dilute-Acid Pretreatment and Enzyme Hydrolysis of Distillers' Grains and Corn Fiber", Appl Biochem Biotech, vol. 159, pp. 553-567, 2009, (15 pages).
Sluiter et al., "Determination of Total Solids in Biomass and Total Dissolved Solids in Liquid Process Samples", National Renewable Energy Laboratory, pp. 1-9, 2008, (9 pages).
Sluiter et al., "Determination of Ash in Biomass", National Renewable Energy Laboratory, pp. 1-8, 2005, (8 pages).
Hames et al., "Determination of Protein Content in Biomass", National Renewable Energy Laboratory, pp. 1-8, 2008, (8 pages).
Sluiter et al., "Determination of Extractives in Biomass", National Renewable Energy Laboratory, pp. 1-12, 2005, (12 pages).
Sluiter et al., "Determination of Structural Carbohydrates and Lignin in Biomass", National Renewable Energy Laboratory, pp. 1-18, 2012, (18 pages).
Sluiter et al., "Determination of starch in solid biomass samples", National Renewable Energy Laboratory, pp. 1-7, 2005, (4 pages). (Abstract only).
Ankom, "Acid Detergent Fiber in Feeds—Filter Bag Technique (for A2000 and A2000I)", ADF method, pp. 1-2, 2017, (2 pages).
Cheetham et al., "Variation in crystalline type with amylase content in maize starch granules: an X-ray powder diffraction study", Carbohydrate Polymers, vol. 36, pp. 277-284, 1998, (8 pages).
Nara et al., "Studies on the Relationship Between Water-satured State and Crystallinity by the Diffraction Method or Moistened Potato Starch", Starch, vol. 35, Issue 12, pp. 407-410, 1983, (3 pages). (Abstract only).
Beneditti et al., "X-ray diffraction methods to determine crystallinity and preferred orientation of lithium disilicate in Li—Zn-silicate glass-ceramic fibres", Journal of Materials Science, vol. 18, pp. 1039-1048, 1983, (8 pages). (Abstract Only).

AOAC International "AOAC 965.22-1966", p. 1, 1996, (1 page).
Wongsagonsup et al., "Effects of Different Mill Types on Ethanol Production Using Uncooked Dry-Grind Fermentation and Characteristics of Residual Starch in Distiller's Dried Grains (DDG)", Cereal Chemistry, vol. 94, Issue 4, pp. 645-653, 2017, (2 pages). (Abstract only).
Chatzifragkou et al., "Biorefinery strategies for upgrading distillers' dried grains with solubles (DOGS)", Process Biochemistry, vol. 50, pp. 2194-2207, 2015, (14 pages).
"Thin Stillage Solids Separation System", retrieved on Jun. 26, 2018 via http://www.icminc.com/products/thin-stillagesolids-separation-system.html, (2 pages).
"About Harvesting Technology: Bringing Profitable Innovation for Ethanol Production", retrieved on Jun. 26, 2018 via http://harvestingtech.com/#benefits, (11 pages).
Hunt, et al. "Corn Stillage as a Feedstuff for Broilers and Turkeys", Applied Poultry Science, Inc., Research Report 1997, published online at http://japr.fass.org/contenl/6/3/310.full.pdf, (9 pages).
Abdel-Tawwab et al., "Evaluation of commercial live bakers' yeast, *Saccharomyces cerevisiae* as a growth and immunity promoter for Fry Nile tilapia, *Oreochromis niloticus* (L.) challenged in situ with Aeromonas hydrophila", Aquaculture, vol. 280, Issues 1-4, pp. 185-189, 2008, (5 pages).
Kim et al., "Composition of corn dry-grind ethanol by-products: DDGS, wet cake, and thin stillage", ScienceDirect, Bioresource Technology, vol. 99, pp. 5165-5176, 2008, (12 pages).
Rausch et al., "The Future of Coproducts From Corn Processing", Applied Biochemistry and Biotechnology, vol. 128, pp. 47-86, 2006, (40 pages).
Yamada et al., "Yeast (*Saccharomyces cerevisiae*) Protein Concentrate: Preparation, Chemical Composition, and Nutritional and Functional Properties", Journal of Agricultural and Food Chemistry, vol. 53, No. 10, pp. 3931-3936, 2005, (6 pages).
Svonja,"From Operating Ease to Operating Costs: Weighing Differences in DDGS Dryers", retreived from http://ethanolproducer.com/articles/3032/from-operating-ease-to-operating-costs-weighing-differences-in-ddgs-dryers, May 22, 2007, (3 pages).
Flash Dryer, retrieved from https://www.gea.com/en/products/dryers-particle-processing/flash-dryers-coolers/flash-dryer.jsp, on Jun. 9, 2020, (11 pages).
Ring Dryer, retrieved from https://www.gea.com/en/products/dryers-particle-processing/ring-dryers/ring-dryer.jsp, on Jun. 9, 2020, (12 pages).
International Search Report and Written Opinion for International Application No. PCT/US2016/063657, dated Feb. 7, 2017, (11 pages).
International Search Report and Written Opinion for International Application No. PCT/US2016/063666, dated Mar. 27, 2017, (11 pages).
International Search Report and Written Opinion for International Application No. PCT/US2017/034324, dated Aug. 14, 2017, (8 pages).
International Search Report and Written Opinion for International Application No. PCT/IB2018/053688, dated Aug. 21, 2018, (14 pages).
International Preliminary Report on Patentability for International Application No. PCT/IB2018/053688, dated Nov. 26, 2019, (11 pages).
International Preliminary Report on Patentability for International Application No. PCT/US2017/034324, dated Nov. 26, 2019, (7 pages).
International Preliminary Report on Patentability for International Application No. PCT/US2016/063657, dated May 29, 2018, (9 pages).
International Preliminary Report on Patentability for International Application No. PCT/US2016/063666, dated May 29, 2018, (10 pages).
Unpublished Utility U.S. Appl. No. 17/666,092, filed Feb. 7, 2022 (no attachment).

* cited by examiner

PROCESSES FOR PRODUCING ONE OR MORE FERMENTATION PRODUCTS IN A SECOND FERMENTATION

CROSS REFERENCE TO RELATED APPLICATIONS

This application is a continuation of U.S. application Ser. No. 16/102,835 filed Aug. 14, 2018, which is a divisional of U.S. patent application Ser. No. 15/604,507, filed on May 24, 2017, which is a continuation-in-part of U.S. patent application Ser. No. 15/529,025, filed on May 23, 2017, which is a National Stage Application under 35 U.S.C. § 371 of PCT/US2016/063666, filed on Nov. 23, 2016, which claims priority to U.S. Provisional Patent Application No. 62/324,159, filed on Apr. 18, 2016, and to U.S. Provisional Patent Application No. 62/260,181, filed on Nov. 25, 2015. U.S. patent application Ser. No. 15/604,507, filed on May 24, 2017, is also a continuation-in-part of U.S. patent application Ser. No. 15/529,014, filed on May 23, 2017, which is a National Stage Application under 35 U.S.C. § 371 of PCT/US16/63657, filed on Nov. 23, 2016, which claims priority to U.S. Provisional Patent Application No. 62/260,181, filed on Nov. 25, 2015. All of which are incorporated by reference herein.

BACKGROUND

Field

Embodiments described generally relate to processes and systems for recovering products derived from ground corn. More particularly, such embodiments relate to processes and systems for recovering products from a corn fermentation mash.

Description of the Related Art

Corn or maize is often used as a starch source to produce ethanol by fermentation. Corn is traditionally ground by a hammer mill in ethanol production facilities. Hammer milled corn has a very wide range of sizes and generally includes relatively large particle sizes.

The fermentation process produces a corn fermentation mash that includes a mixture of ethanol and multiple corn products. Ethanol is removed from the corn fermentation mash by distillation to produce a whole stillage that contains a mixture of corn products. Many of these corn products are too time consuming and/or costly to separate from the stillage and therefore are never recovered as separate products.

There is a need, therefore, for improved processes and systems for recovering products from a corn fermentation mash.

SUMMARY

Processes and systems for recovering products from a fermentation mash are provided. In some examples, a process for recovering products from a fermentation mash can include processing a ground corn product to produce a fermentation mash that can include ethanol. At least a portion of the ethanol can be separated from the fermentation mash to produce a whole stillage. The whole stillage can be separated to produce a fiber rich product and a filtrate. The fiber rich product can be hydrolyzed to produce a saccharification mash. The saccharification mash can be processed to produce additional ethanol and a stillage protein product.

In other examples, a process for recovering products from a fermentation mash can include processing a ground corn product to produce a fermentation mash that can include ethanol. At least a portion of the ethanol can be separated from the fermentation mash to produce a whole stillage. The whole stillage can be separated with a fiber filter to produce a fiber rich product and a filtrate. The fiber rich product can be hydrolyzed to produce a saccharification mash. The saccharification mash can be processed to produce additional ethanol and a stillage protein product.

In some examples, a process for recovering products from a fermentation mash can include processing a ground corn product to produce a fermentation mash that can include ethanol. At least a portion of the ethanol can be separated from the fermentation mash to produce a whole stillage. The whole stillage can be separated to produce a fiber rich product and a filtrate. The fiber rich product can have an ethanol potential of at least 90 gallons of ethanol per 1,000 kilograms of the fiber rich product.

BRIEF DESCRIPTION OF THE DRAWINGS

So that the manner in which the above recited features can be understood in detail, a more particular description, briefly summarized above, may be had by reference to embodiments, some of which are illustrated in the appended drawing. It is to be noted, however, that the appended drawing illustrate only typical embodiments and are therefore not to be considered limiting of its scope, for the invention may admit to other equally effective embodiments.

DETAILED DESCRIPTION

Figure 1:
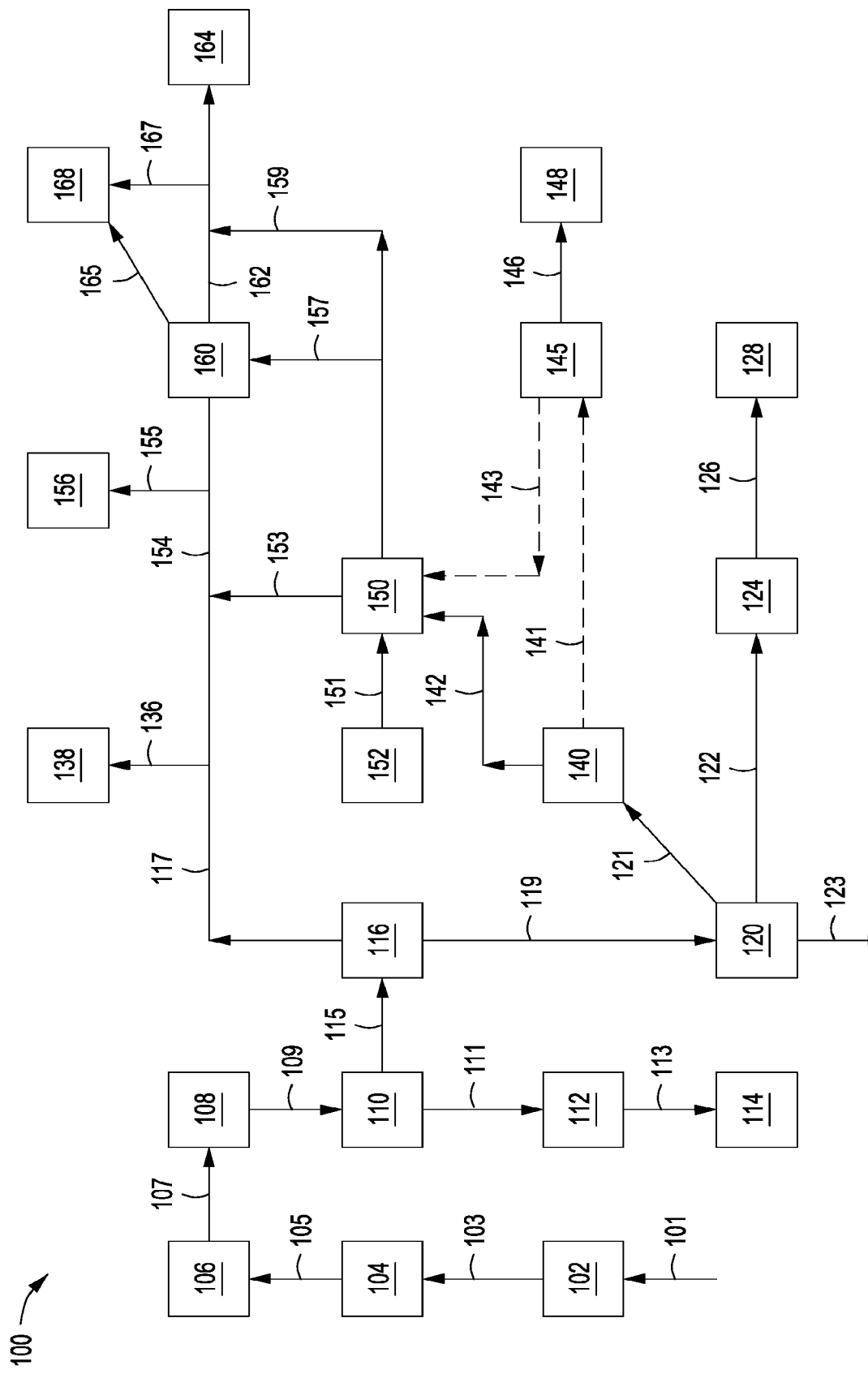
FIG. 1 depicts a schematic view of an illustrative system for recovering products derived from corn fermentation mash, according to one or more embodiments described.

FIG. 1 depicts a schematic view of an illustrative separation system 100 for recovering products derived from fermented corn. Illustrative products derived from fermented corn can include, but are not limited to, ethanol, distillers grains, protein rich products, oil, and other products. A ground corn product that can be produced from the corn, can be processed to produce the fermented corn. The ground corn product can be milled from a plurality of corn pieces by one or more high shear mills. For example, the plurality of corn pieces via line 101 can be introduced into one or more high shear mills 102. The corn pieces, prior to being high shear milled, can be or include, but are not limited to, whole corn kernels, fragmented corn kernels, size-reduced corn kernels, milled corn kernels, ground corn kernels, fresh corn kernels, dried corn kernels, or any mixture thereof. In some examples, whole corn kernels can be size-reduced via one or more non-high shear mills, such as one or more hammer mills and/or one or more roller mills using a non-shearing technique, to produce a coarse ground corn. The coarse ground corn can be further size-reduced, such as sheared, milled, or otherwise ground, in the high shear mill 102 to produce the ground corn product. The high shear mill 102 can be or include, but is not limited to, one or more disk mill fiberizers, one or more air swept pulverizers, one or more other high shear mills, or any combination thereof.

The ground corn product can have a particle size of less than a particle size of conventional ground corn (e.g., hammer milled corn or roller milled corn). For example, the ground corn product can have a $d_{50}$ by volume percent of about 100 μm to about 500 μm, as measured according to ISO 13320:2009. In contrast, hammer milled corn generally has a $d_{50}$ by volume percent of greater than 500 μm and roller milled corn generally has a $d_{50}$ by volume percent of greater than 600 μm.

In some examples, greater than 25 wt % of the ground corn product can have a particle size of greater than 105 μm and greater than 80 wt % of the ground corn product can have a particle size of 425 μm or less, as measured according to AOAC 965.22-1966. The particle size distribution of the ground corn product produced in the high shear mill is further discussed and described below. It has been surprisingly and unexpectedly discovered that when 80 wt % or more of the ground corn product has a particle size of 425 μm or less and when greater than 25 wt % of the ground corn product has a particle size of greater than 105 μm, one or more product yields (e.g., corn oil) and/or one or more system efficiencies is realized as compared to conventional ethanol production processes that use aground corn in which less than 80 wt % of the ground corn has a particle size of 425 μm or less or when less than 25 wt % (e.g., less than 20 wt %) of the ground corn product has a particle size of greater than 105 μm.

The ground corn product produced in the high shear mill 102 can be processed or otherwise treated in one or more process units to produce a fermentation mash. The process units can include one or multiple vessels and/or apparatuses, such as slurry tanks and/or liquefaction tanks, for heating, mixing, separating, and/or carrying out other operations on the slurry. In some examples, the ground corn product via line 103 can be transferred from the high shear mill 102 to one or more slurry tanks 104. Other components or products from downstream in the separation system 100 can also be mixed, blended, or otherwise combined with the ground corn product in the slurry tank 104. The ground corn product can be mixed, blended, or otherwise combined with water and one or more enzymes, such as alpha-amylase, to produce a slurry tank mixture. One or more optional additives and/or one or more optional recycled downstream components can also be mixed, blended, or otherwise combined with the ground corn product, water, and enzyme to produce the slurry tank mixture. The slurry tank mixture can be processed to produce the fermentation mash. The slurry tank mixture can be heated to produce a gelatinized starch. The gelatinized starch can be hydrolyzed to produce a liquefaction mash. The liquefaction mash can be subjected to saccharification and fermentation to produce the fermentation mash.

The slurry tank mixture can be heated in a cooker (e.g., a pressurized jet cooker) to solubilize the starch in the ground corn product to produce a solubilized mixture of gelatinized starch. The slurry tank mixture can be mixed using a paddle mixer, a ribbon blender, a dense phase slurry mixer, or any combination thereof. The slurry tank mixture can be heated to a temperature that is at or above the onset of starch gelatinization where the alpha amylase can solubilize the starch. In one example, this temperature can be above the temperature where the onset of gelatinization occurs, but below the temperature needed to complete gelatinization. The starch is hydrolyzed by the enzyme into maltodextrins and oligosaccharides. Given sufficiently small particle size the hydrolysis can occur without complete gelatinization. Lower temperature liquefaction offers the benefit of reduced energy use and reduced damage to starch due to undesirable side reactions, such as the Maillard reaction, as well as a reduced formation of "dough balls", which are lumps of corn flour that can form in the slurry tank mixture and can reduce or cease the production of ethanol.

The slurry tank mixture in the slurry tank 104 can be heated to a temperature of less than 90° C., less than 85° C., less than 80° C., less than 75° C., less than 72° C., or less than 70° C. For example, the slurry tank mixture can be heated to a temperature of greater than 50° C., greater than 55° C., greater than 60° C., greater than 62° C., greater than 64° C., or greater than 66° C. to less than 90° C., less than 85° C., less than 80° C., less than 75° C., less than 72° C., or less than 70° C.

The solubilized mixture of gelatinized starch via line 105 can be transferred from the slurry tank 104 to one or more liquefaction tanks 106. One or more enzymes, such as alpha-amylase, can be added to the solubilized mixture of gelatinized starch in a liquefaction process to produce a liquefaction mash containing a hydrolyzed mixture. The enzyme can hydrolyze the gelatinized starch into maltodextrins and oligosaccharides.

The liquefaction mash via line 107 can be transferred from the liquefaction tank 106 to one or more fermenters 108. The liquefaction mash containing the hydrolyzed mixture can be further processed in one or more saccharification and fermentation processes to produce the fermentation mash. The saccharification and fermentation can occur sequentially or simultaneously. During saccharification, the liquefied mash can be cooled and one or more enzymes, such as glucoamylase, can be added to hydrolyze the maltodextrins and oligosaccharides into single glucose sugar molecules. During fermentation, one or more strains of yeast, such as *Saccharomyces cerevisae*, can be added to metabolize the glucose sugars into ethanol and carbon dioxide. After saccharification and fermentation, in some examples, the fermentation mash can include about 15 vol % to about 25 vol % of ethanol (volume/volume basis), as well as remaining grain components.

The fermentation mash via line 109 can be pumped or otherwise transferred from the fermenter 108 to one or more distillers 110 where the fermentation mash can be heated to vaporize at least a portion of the ethanol. The distiller 110 can be or include, but is not limited to, one or more distillation columns, one or more distillation trains, one or more condensers, or other device(s) configured to vaporize the ethanol and to condense the vaporized ethanol. The ethanol can be distilled or otherwise separated from the fermentation mash within the distiller 110 to produce a whole stillage. The whole stillage can include, but is not limited to, water, fibers, starches, oils, and proteins.

The vaporized ethanol can be condensed in a condenser within the distiller 110, and liquid alcohol (e.g., ethanol) can be recovered from the distiller 110 at about 95 vol % purity (190 proof). The 190 proof ethanol via line 111 can be transferred into one or more dehydrators 112 and dried. The dehydrator 112 can be or include one or more dehydration columns, such as molecular sieve dehydration columns. The 190 proof ethanol can pass through the dehydration columns in the dehydrator 112 that can remove residual water from the ethanol, to yield a drier product of purified ethanol, such as about 99.75 vol % of ethanol (about 199.5 proof) that can be transferred via line 113 to one or more ethanol storage containers 114.

The whole stillage left in the distiller 110 can be further processed to separate and/or recover a variety of products. Illustrative products that can be derived from the whole stillage can include, but are not limited to, other alcohols, oil products (e.g., a corn oil product), distillers grains (e.g., a wet fiber rich product, a wet fiber rich product with syrup, a dried fiber rich product, and/or a dried fiber rich product with syrup), protein products (e.g., a protein rich product), and/or other products from the whole stillage (e.g., a syrup product).

The whole stillage left in the distiller 110 can be transferred via line 115 to one or more separators 116. The whole stillage can be contacted or otherwise processed in the separator 116 to separate or otherwise produce a fiber rich portion or fiber rich product via line 117 and a filtrate via line 119. For example, the fiber rich product can be filtered or otherwise removed from stillage by the separator 116 to produce the filtrate that passes through the separator 116. The fiber rich product can include fibrous material, such as fibers. The fiber rich product can be used alone or combined with other components to produce various types of products, as will be further discussed and described below.

The separator 116 can be or include, but is not limited to, one or more pressure screens, one or more centrifuges (e.g., a filtration centrifuge such as those discussed and described in U.S. Pat. Nos. 8,813,973 and 8,778,433), one or more paddle screens, one or more fiber filters, one or more rotary drum screens, one or more rotary vacuum drum filters, one or more brush strainers, one or more vibratory separators, one or more centrifugal screeners, one or more linear motion screens, one or more vacu-deck screens, or any combination thereof.

In some examples, the separator 116 can be or include a single pressure screen. In other examples, the separator 116 can be or include two or more pressure screens. In other examples, the separator 116 can be a single pressure screen or two or more pressure screens and can be free of or otherwise exclude any centrifuge. In another example, the separator 116 be a single pressure screen or two or more pressure screens and can be free of or otherwise exclude any centrifuge, paddle screen, fiber filter, or any combination of centrifuge, paddle screen, and filter. In another example, the separator 116 can be a single pressure screen or two or more pressure screens and can be free of or otherwise exclude any centrifuge, paddle screen, fiber filter, rotary drum screen, rotary vacuum drum filter, brush strainer, vibratory separator, centrifugal screener, linear motion screen, and vacuum deck screen. As such, in at least one example, the whole stillage in line 115 can be separated into the fiber rich product via line 117 and the filtrate via line 119 with only one or two or more pressure screens.

Illustrative pressure screens can be or include outflow pressure screens, inflow pressure screens, inflow/outflow pressure screens, and/or foils on accept side of plate pressure screens. In an outflow pressure screen, the whole stillage can flow from the inside of the screen plate cylinder to the outside, with the rotor being on the inside of the screen plate. The fibers can be held inside the plate until the fibers reach the reject port. In an inflow pressure screen, the whole stillage can flow from the outside of the screen cylinder to the inside with the rotor being on the outside of the screen plate. The fibers can be held on the outside of the cylinder. Suitable rotors can include foiled rotors, bump rotors, lobe rotors, and/or S-rotors. The openings in the pressure screens can be circular, slotted, or a combination thereof. The pressure screen can be made by milling slots into a single piece of metal and rolling the milled metal into a cylinder. The pressure screen can also be made by banding wires together to form a cylinder, which is also referred to as wedge-wire baskets.

Pressure screens that include slotted openings can have a width of about 12 μm, about 25 μm, about 50 μm, or about 75 μm to about 100 μm, about 130 μm, about 150 μm, about 175 μm, about 230 μm, about 255 μm, about 330 μm, about 380 μm, about 430 μm, about 500 μm, or more. In some examples, the pressure screen can include slotted openings having a width of about 10 μm, about 30 μm, about 50 μm, about 75 μm, about 100 μm, about 125 μm, or about 150 μm to less than 250 μm, less than 300 μm, less than 350 μm, less than 400 μm, less than 450 μm, or less than 500 μm.

In other examples, the separator 116 can be or include one or more fiber filters. In some examples, the separator 116 can be a single fiber filter. In other examples, the separator 116 can be a single fiber filter or two or more fiber filters. In some examples, the separator 116 can be or include 1, 2, 3, 4, 5, 6, 7, 8, 9, 10, or more fiber filters. In other examples, the separator 116 can be a single fiber filter or two or more fiber filters and can be free of or otherwise exclude any centrifuge, any pressure screen, any paddle screen, or any combination of a centrifuge, pressure screen, and paddle screen. In some examples, the separator 116 can be or include 1, 2, 3, 4, 5, 6, 7, 8, 9, 10, or more fiber filters and can be free of or otherwise exclude any centrifuge, any pressure screen, any paddle screen, or any combination of a centrifuge, pressure screen, and paddle screen. In another example, the separator 116 can be a single fiber filter or two or more fiber filters and can be free of or otherwise exclude any pressure screen, centrifuge, paddle screen, rotary drum screen, rotary vacuum drum filter, brush strainer, vibratory separator, centrifugal screener, linear motion screen, and vacuum deck screen. In some examples, the separator 116 can be or include 1, 2, 3, 4, 5, 6, 7, 8, 9, 10, or more fiber filters and can be free of or otherwise exclude any pressure screen, centrifuge, paddle screen, rotary drum screen, rotary vacuum drum filter, brush strainer, vibratory separator, centrifugal screener, linear motion screen, and vacuum deck screen. As such, in at least one example, the whole stillage in line 115 can be separated into the fiber rich product via line 117 and the filtrate via line 119 with only one or two or more fiber filters.

The whole stillage can be introduced, e.g., pumped, into a filter sleeve of the fiber filter. The filter sleeve can have hole sizes or openings of about 12.7 µm, about 25.4 µm, about 50.8 µm, or about 76.2 µm to about 101.6 µm, about 127 µm, about 152.4 µm, about 177.8 µm, about 230 µm, about 255 µm, about 330 µm, about 380 µm, about 430 µm, about 500 µm, or more. In another example, the filter sleeve can have hole sizes or openings of about 10 µm, about 12 µm, about 25 µm, about 50 µm, or about 75 µm to about 100 µm, about 130 µm, about 150 µm, about 175 µm, about 230 µm, about 255 µm, about 330 µm, about 380 µm, about 430 µm, about 500 µm, or more. In some examples, the filter sleeve can have hole sizes or openings of about 10 µm, about 30 µm, about 50 µm, about 75 µm, about 100 µm, about 125 µm, or about 150 µm to less than 250 µm, less than 300 µm, less than 350 µm, less than 400 µm, less than 450 µm, or less than 500 µm.

The filter sleeve can be vibrated, e.g., at high frequency. For example, vibration of the filter sleeve can be accomplished by (1) tensioning the filter sleeve with a pair of springs, (2) rotating a high speed rotor disposed inside the filter sleeve that can induce pulsed waves in the whole stillage, or (3) a combination thereof. The rotor can include one or more flights that can push or otherwise urge solids toward a sludge discharge at the end of the fiber filter. For example, the rotor can include straight paddles with ribbon flighting that can direct solids toward the discharge. The pulsing and/or vibrations can also force or otherwise urge the filtered liquid through the filter sleeve. The filter sleeve can be made of one or more polymer fabrics. The polymer can be or include, but is not limited to, polyester, polyether ether ketone (PEEK), or other suitable polymers. The polymer fabric can be a woven polymer fabric. Any type of weave can be used to produce a filter sleeve composed of a woven polymer fabric. Illustrative types of weaves can include plain weave, twill weave, satin weave, basket weave, leno weave, and mock leno weave. The filter sleeve can be formed by connecting opposing edges of a filter sleeve by a lap or double hook joint. One suitable fiber filter can include the fiber filter discussed and described in U.S. Pat. No. 6,117,321. In some examples, the fiber filter can include a filtering body that includes a filter unit. The filter unit can include, but is not limited to, a flexible filtering sleeve and a rotor disposed within the flexible filtering sleeve. The rotor can be configured to pulse a fluid radially outwardly against the filtering sleeve. The filtering sleeve can be assembled or otherwise located on the filtering body via one or more supports. The one or more supports can be elastic and can permit the filtering sleeve to expand and contract along a longitudinal axis thereof. The one or more supports can be adjusted and tensioned by one or more adjustment devices located outside of the flow of a filtrate. Some commercially available fiber filters can include, but are not limited to, the FF 6, the FF 12, and the FF 30, available from Vincent Corporation.

In other examples, the separator 116 can be or include one or more paddle screens. In some examples, the separator 116 can be a single paddle screen. In other examples, the separator 116 can be a single paddle screen or two or more paddle screens. In other examples, the separator 116 can be a single paddle screen or two or more paddle screens and can be free of or otherwise exclude any centrifuge, any pressure screen, and fiber filter, or any combination of a centrifuge, pressure screen, and fiber filter. In another example, the separator 116 can be a single paddle screen or two or more paddle screens and can be free of or otherwise exclude any pressure screen, centrifuge, fiber filter, rotary drum screen, rotary vacuum drum filter, brush strainer, vibratory separator, centrifugal screener, linear motion screen, and vacuum deck screen. As such, in at least one example, the whole stillage in line 115 can be separated into the fiber rich product via line 117 and the filtrate via line 119 with only one or two or more paddle screens.

The paddle screen can include a screen that can include openings of about 12.7 µm, about 25.4 µm, about 50.8 µm, or about 76.2 µm to about 101.6 µm, about 127 µm, about 152.4 µm, about 177.8 µm, about 230 µm, about 255 µm, about 330 µm, about 380 µm, about 430 µm, about 500 µm, or more. In another example, the screen can have openings of about 12 µm, about 25 µm, about 50 µm, or about 75 µm to about 100 µm, about 130 µm, about 150 µm, about 175 µm, about 230 µm, about 255 µm, about 330 µm, about 380 µm, about 430 µm, about 500 µm, or more. In some examples, the screen can have openings of about 10 µm, about 30 µm, about 50 µm, about 75 µm, about 100 µm, about 125 µm, or about 150 µm to less than 250 µm, less than 300 µm, less than 350 µm, less than 400 µm, less than 450 µm, or less than 500 µm. A commercially available paddle screen can include, but is not limited to, the FQ-PS32 Paddle Screen available from Fluid-Quip, Inc.

In other examples, the separator 116 can be or include one or more rotary drum screens. In some examples, the separator 116 can be or include a single rotary drum screen. In other examples, the separator 116 can be or include a single rotary drum screen or two or more rotary drum screens. In other examples, the separator 116 can be or include a single rotary drum screen or two or more rotary drum screens and can be free of or otherwise exclude any pressure screen, centrifuge, paddle screen, fiber filter, rotary vacuum drum filter, brush strainer, vibratory separator, centrifugal screener, linear motion screen, and vacuum deck screen. As such, in at least one example, the whole stillage in line 115 can be separated into the fiber rich product via line 117 and the filtrate via line 119 with only one or two or more rotary drum screens.

The rotary drum screen can include a filter element or screen having openings of about 10 µm, about 25 µm, about 50 µm, or about 75 µm to about 100 µm, about 130 µm, about 150 µm, about 175 µm, about 230 µm, about 255 µm, about 330 µm, about 380 µm, about 430 µm, about 500 µm, about 700 µm, about 900 µm, about 1 mm, about 1.5 mm, about 2 mm, or more. In some examples, the rotary drum screen can include openings of about 10 µm, about 30 µm, about 50 µm, about 75 µm, about 100 µm, about 125 µm, or about 150 µm to less than 250 µm, less than 300 µm, less than 350 µm, less than 400 µm, less than 450 µm, or less than 500 µm. A commercially available rotary drum screen can include, but is not limited to, the LIQUI-FUGE® LFS rotary drum screen available from Vulcan.

In other examples, the separator 116 can be or include one or more brush strainers. In some examples, the separator 116 can be or include a single brush strainer. In other examples, the separator 116 can be or include a single brush strainer or two or more brush strainers. In other examples, the separator 116 can be or include a single brush strainer or two or more brush strainers and can be free of or otherwise exclude any pressure screen, centrifuge, paddle screen, fiber filter, rotary drum screen, rotary vacuum drum filter, vibratory separator, centrifugal screener, linear motion screen, and vacuum deck screen. As such, in at least one example, the whole stillage in line 115 can be separated into the fiber rich product via line 117 and the filtrate via line 119 with only one or two or more brush strainers. The brush strainer can include a casing surrounding a filter element or perforated strainer cylinder, through which the liquid can flow through. Particles suspended in the whole stillage can be held back in the cylinder and forced downward by rotating brushes mounted on a shaft.

The filter element or perforated strainer cylinder can have openings of about 10 μm, about 25 μm, about 50 μm, or about 75 μm to about 100 μm, about 130 μm, about 150 μm, about 175 μm, about 230 μm, about 255 μm, about 330 μm, about 380 μm, about 430 μm, about 500 μm, about 700 μm, about 900 μm, about 1 mm, about 1.5 mm, about 2 mm, or more. In some examples, the perforated strainer cylinder can include openings of about 10 μm, about 30 μm, about 50 μm, about 75 μm, about 100 μm, about 125 μm, or about 150 μm to less than 250 μm, less than 300 μm, less than 350 μm, less than 400 μm, less than 450 μm, or less than 500 μm. A commercially available brush strainer can include, but is not limited to, the W-SIL self-cleaning brush strainer, available from Alfa Laval.

In other examples, the separator 116 can be or include one or more rotary vacuum drum filters. In some examples, the separator 116 can be or include a single rotary vacuum drum filter. In other examples, the separator 116 can be or include a single rotary vacuum drum filter or two or more rotary vacuum drum filters. In other examples, the separator 116 can be or include a single rotary vacuum drum filter or two or more rotary vacuum drum filters and can be free of or otherwise exclude any pressure screen, centrifuge, paddle screen, fiber filter, rotary drum screen, brush strainer, vibratory separator, centrifugal screener, linear motion screen, and vacuum deck screen. As such, in at least one example, the whole stillage in line 115 can be separated into the fiber rich product via line 117 and the filtrate via line 119 with only one or two or more rotary vacuum drum filters.

The rotary vacuum drum filter can include a vacuum pump, a filtrate pump, and a vacuum/filtrate receiver. The rotary vacuum drum filter can also include feed and/or drain pumps and pre-coat or chemical prep tanks. The drum can rotate while partially submerged in the whole stillage. A vacuum can draw liquid through the filter element or screen, e.g., a cloth or fabric filter element on the drum surface which retains the solids. The vacuum can pull a gas, e.g., air, through the cake and remove moisture as the drum rotates. The filter element can have openings of about 10 μm, about 25 μm, about 50 μm, or about 75 μm to about 100 μm, about 130 μm, about 150 μm, about 175 μm, about 230 μm, about 255 μm, about 330 μm, about 380 μm, about 430 μm, about 500 μm, about 700 μm, about 900 μm, about 1 mm, about 1.5 mm, about 2 mm, or more. In some examples, the filter medium can include openings of about 10 μm, about 30 μm, about 50 μm, about 75 μm, about 100 μm, about 125 μm, or about 150 μm to less than 250 μm, less than 300 μm, less than 350 μm, less than 400 μm, less than 450 μm, or less than 500 μm. A commercially available rotary vacuum drum filter can include, but is not limited to, the vacuum drum rotary filters available from Komline-Sanderson.

In other examples, the separator 116 can be or include one or more vibratory separators. In some examples, the separator 116 can be or include a single vibratory separator. In other examples, the separator 116 can be or include a single vibratory separator or two or more vibratory separators. In other examples, the separator 116 can be or include a single vibratory separator or two or more vibratory separators and can be free of or otherwise exclude any pressure screen, centrifuge, paddle screen, fiber filter, rotary drum screen, brush strainer, rotary vacuum drum filter, centrifugal screener, linear motion screen, and vacuum deck screen. As such, in at least one example, the whole stillage in line 115 can be separated into the fiber rich product via line 117 and the filtrate via line 119 with only one or two or more vibratory separators.

The vibratory separator can vibrate, e.g., about its center of mass. The vibration can be induced by eccentric weights on the upper and lower ends of a motion-generator shaft. The vibratory separator can include one or more filter elements, e.g., screen decks, e.g., 1, 2, 3, 4, or more filter elements. The filter element, e.g., screen decks, can have openings of about 10 μm, about 25 μm, about 50 μm, or about 75 μm to about 100 μm, about 130 μm, about 150 μm, about 175 μm, about 230 μm, about 255 μm, about 330 μm, about 380 μm, about 430 μm, about 500 μm, about 700 μm, about 900 μm, about 1 mm, about 1.5 mm, about 2 mm, or more. In some examples, the filter elements can include openings of about 10 μm, about 30 μm, about 50 μm, about 75 μm, about 100 μm, about 125 μm, or about 150 μm to less than 250 μm, less than 300 μm, less than 350 μm, less than 400 μm, less than 450 μm, or less than 500 μm. Some commercially available vibratory separators can include, but are not limited to, the VIBRO-ENERGY® Round Separators, the MX Separators, and the Super MX Separators, available from SWECO, Inc.

In other examples, the separator 116 can be or include one or more centrifugal screeners. In some examples, the separator 116 can be or include a single centrifugal screener. In other examples, the separator 116 can be or include a single centrifugal screener or two or more centrifugal screeners. In other examples, the separator 116 can be or include a single centrifugal screener or two or more centrifugal screeners and can be free of or otherwise exclude any pressure screen, centrifuge, paddle screen, fiber filter, rotary drum screen, brush strainer, rotary vacuum drum filter, vibratory separator, linear motion screen, and vacuum deck screen. As such, in at least one example, the whole stillage in line 115 can be separated into the fiber rich product via line 117 and the filtrate via line 119 with only one or two or more centrifugal screeners.

The whole stillage can be introduced to an inlet and redirected into a cylindrical sifting chamber via a feed screw. Helical paddles can be rotated within the chamber to propel the whole stillage against a screen, while the resultant, centrifugal force on the particles can accelerate the particles through apertures in the screen. The rotating paddles, which do not contact the screen, can breakup soft agglomerates. Over-sized particles and trash can be ejected via an oversize discharge spout. The screen can have openings of about 10 μm, about 25 μm, about 50 μm, or about 75 μm to about 100 μm, about 130 μm, about 150 μm, about 175 μm, about 230 μm, about 255 μm, about 330 μm, about 380 μm, about 430 μm, about 500 μm, about 700 μm, about 900 μm, about 1 mm, about 1.5 mm, about 2 mm, or more. In some examples, the screen can include openings of about 10 μm, about 30 μm, about 50 μm, about 75 μm, about 100 μm, about 125 μm, or about 150 μm to less than 250 μm, less than 300 μm, less than 350 μm, less than 400 μm, less than 450 μm, or less than 500 μm. A commercially available centrifugal screener can include, but is not limited to, the CENTRI-SIFTER™, available from Kason Corporation.

In other examples, the separator 116 can be or include one or more linear motion screens. In some examples, the separator 116 can be or include a single linear motion screen. In other examples, the separator 116 can be or include a single linear motion screen or two or more linear motion screens. In other examples, the separator 116 can be or include a single linear motion screen or two or more linear motion screens and can be free of or otherwise exclude any pressure screen, centrifuge, paddle screen, fiber filter, rotary drum screen, brush strainer, rotary vacuum drum filter, vibratory separator, centrifugal screener, and vacuum deck screen. As such, in at least one example, the whole stillage in line 115 can be separated into the fiber rich product via line 117 and the filtrate via line 119 with only one or two or more linear motion screens.

The whole stillage can be introduced to the linear motion screener, which can include an angled filter element, e.g., screen. The filter element can be at an angle of about +10° to about −15° relative to horizontal. The filter element or screen can have openings of about 10 µm, about 25 µm, about 50 µm, or about 75 µm to about 100 µm, about 130 µm, about 150 µm, about 175 µm, about 230 µm, about 255 µm, about 330 µm, about 380 µm, about 430 µm, about 500 µm, about 700 µm, about 900 µm, about 1 mm, about 1.5 mm, about 2 mm, or more. In some examples, the filter element or screen can include openings of about 10 µm, about 30 µm, about 50 µm, about 75 µm, about 100 µm, about 125 µm, or about 150 µm to less than 250 µm, less than 300 µm, less than 350 µm, less than 400 µm, less than 450 µm, or less than 500 µm. A commercially available linear motion screener can include, but is not limited to, the linear motion screeners available from Tinsley Company.

In other examples, the separator 116 can be or include one or more vacu-deck screens. In some examples, the separator 116 can be or include a single vacu-deck screen. In other examples, the separator 116 can be or include a single vacu-deck screen or two or more vacu-deck screens. In other examples, the separator 116 can be or include a single vacu-deck screen or two or more vacu-deck screens and can be free of or otherwise exclude any pressure screen, centrifuge, paddle screen, fiber filter, rotary drum screen, brush strainer, rotary vacuum drum filter, vibratory separator, centrifugal screener, and linear motion screener. As such, in at least one example, the whole stillage in line 115 can be separated into the fiber rich product via line 117 and the filtrate via line 119 with only one or two or more vacu-deck screens.

The vacu-deck screen can include one or more filter elements or screens that can have openings of about 10 µm, about 25 µm, about 50 µm, or about 75 µm to about 100 µm, about 130 µm, about 150 µm, about 175 µm, about 230 µm, about 255 µm, about 330 µm, about 380 µm, about 430 µm, about 500 µm, about 700 µm, about 900 µm, about 1 mm, about 1.5 mm, about 2 mm, or more. In some examples, the filter element or screen can include openings of about 10 µm, about 30 µm, about 50 µm, about 75 µm, about 100 µm, about 125 µm, or about 150 µm to less than 250 µm, less than 300 µm, less than 350 µm, less than 400 µm, less than 450 µm, or less than 500 µm. A commercially available vacu-deck screen can include, but is not limited to, the vacu-deck screens available from Tinsley Company.

The separator 116, e.g., a pressure screen and/or a fiber filter, can process or filter the whole stillage at a rate of about 94.6 liters per minute, about 379 liters per minute, about 946 liters per minute, or about 1,890 liters per minute to about 2,840 liters per minute, about 3,790 liters per minute, about 4,730 liters per minute, about 5,680 liters per minute, about 6,620 liters per minute, about 7,570 liters per minute, about 11,000 liters per minute, about 15,000 liters per minute, about 19,000 liters per minute, about 22,500 liters per minute, about 26,500 liters per minute, or about 30,500 liters per minute. In one example, the separator, e.g., a pressure screen and/or a fiber filter, can process or filter the whole stillage at a rate of at least 1,890 liters per minute, at least 2,460 liters per minute, at least 3,030 liters per minute, at least 3,600 liters per minute, at least 3,970 liters per minute, at least 4,540 liters per minute, at least 4,920 liters per minute, or at least 5,300 liters per minute to about 5,680 liters per minute, about 6,620 liters per minute, about 7,570 liters per minute, about 12,000 liters per minute, about 20,000 liters per minute, about 26,000 liters per minute, or about 30,500 liters per minute.

In some examples, if the separator 116 is or includes one or more fiber filters, the filtrate via line 119 can contains less solids as compared to if the separator 116 includes one or more centrifuges, one or more pressure screens, one or more paddle screens, or any combination thereof. In other examples, if the separator 116 includes only one or more fiber filters, i.e., does not include a centrifuge, a pressure screen, a paddle screen, or other separator, the filtrate via line 119 can contain less solids as compared to if the separator includes a centrifuge, a pressure screen, a paddle screen, or other separator, but not a fiber filter.

The filtrate can be transferred via line 119 from the separator 116 to one or more separators 120 (e.g., a two phase separator such as a nozzle centrifuge, or a three phase separator such as a TRICANTER®, available from Flottweg). As shown, the separator 120 can be a three phase separator and can separate or otherwise produce a protein rich product via line 122, an oil product via line 123, and a clarified stillage that can be free from or have a reduced oil content via line 121. In other examples, the separator 120 can be a centrifuge that can separate or otherwise produce the protein rich product via line 122 and a clarified stillage via line 121 from the filtrate in line 119. The separator 120 can be provided with washing capabilities so that water, along with the filtrate, can be supplied to the separator 120. If the separator 120 includes a centrifuge, the additional water can facilitate separation of the filtrate into the protein rich product and the clarified stillage. The heavier protein can separate from the lighter components and can be removed as an underflow containing the protein rich product, whereas the lighter components, which can include oil and starch, can be removed as an overflow containing the clarified stillage. In other examples, the separator 120 can also include or can be replaced with a cyclone separation apparatus or other device to separate the filtrate portion into the protein rich product and the clarified stillage.

The protein rich product can be dewatered or otherwise dried such that water can be removed from the protein rich product to produce a dried protein product. The protein rich product via line 122 can be transferred from the centrifuge 120 to one or more dryers 124. In some examples, as depicted in FIG. 1, the protein rich product via line 122 can be transferred to the dryer 124 to reduce the amount of water and/or otherwise dry the protein rich product to produce the dried protein product. The dried protein product via line 126 can be transferred from the dryer 124 to one or more storage containers 128. In some examples, the separated water portion or filtrate from the dryer 124 can be recycled back or otherwise transferred to the fermenter 108 for liquefaction and/or fermentation. The dried protein product can include less water than the protein rich product.

The dryer 124 can be or include one or more centrifuges (e.g., a decanter centrifuge), one or more ring dryers (e.g., P-ring dryers), one or more flash dryers, one or more fluid bed dryers, one or more heated air dryers, one or more heaters, one or more steam dryers (e.g., steam ring dryers, steam flash dryers, and/or steam tube dryers), one or more rotary dryers, one or more steam and rotary dryers (e.g., Swiss Combi's ecoDRY™ drying system), one or more superheated steam dryers, one or more spray dryers, one or more vacuum filtration dryers, one or more other drying devices, or any combination thereof to remove water and produce the dried protein product.

The dried protein product in line 126 can be or include high protein corn meal. In some examples, the dried protein product can be used as fish feed, shrimp feed, crab feed, other aquaculture feeds, pig feed, cattle feed, chicken feed, or other livestock feed. The dried protein product can include about 35 wt %, about 40 wt %, or about 45 wt % to about 50 wt %, about 55 wt %, about 60 wt %, about 70 wt %, about 80 wt %, or greater of protein on a dry matter basis. For example, the dried protein product can include about 35 wt % to about 80 wt %, about 35 wt % to about 70 wt %, about 35 wt % to about 60 wt %, about 35 wt % to about 55 wt %, about 35 wt % to about 50 wt %, about 45 wt % to about 80 wt %, about 45 wt % to about 70 wt %, about 45 wt % to about 60 wt %, about 45 wt % to about 55 wt %, or about 45 wt % to about 50 wt % of protein on a dry matter basis.

The clarified stillage via line 121, whether recovered from a three phase separator or a two phase separator, can be transferred via line 121 to one or more evaporators 140. The clarified stillage can be dewatered, i.e., water can be removed from the clarified stillage, to produce an evaporated clarified stillage. For example, the evaporator 140 can gasify at least a portion of the water in the clarified stillage to produce the evaporated clarified stillage.

In some examples, the evaporated clarified stillage via line 142 can be transferred from the evaporator 140 to one or more additional evaporators 150. For example, if the separator 120 is or includes a three phase separator, the evaporated clarified stillage via line 142 can be introduced to the additional evaporator 150. In other examples, the evaporated clarified stillage via line 141 can be transferred from the evaporator 140 to one or more oil recovery centrifuges 145. For example, if the separator 120 is or includes a centrifuge, the evaporated clarified stillage can be introduced to the oil recovery centrifuge 145 to separate and produce an oil product and an evaporated clarified stillage with reduced oil, also referred to as a stillage with reduced oil. One or more oil products via line 146 can be transferred from the oil recovery centrifuge 145 to one or more storage containers 148. The oil product can include a mixture of typical fatty acids found in corn oil. In some examples, the final recovered oil product can be about 30 wt %, about 40 wt %, about 45 wt % to about 50 wt %, about 60 wt %, or about 70 wt % of the total corn oil in the corn (e.g., corn kernels and/or other corn pieces). The oil recovery centrifuge 145 can function at a higher capacity because the evaporated clarified stillage, which can be subjected to the oil recovery centrifuge 145, can include less water and less protein than the clarified stillage. It should be noted that the evaporated clarified stillage in line 142, when the separator 120 is or includes a three phase separator and produces the oil product via line 123, can also be introduced to the oil recovery centrifuge 145 to produce additional oil product via line 146, provided less than all of the oil in the filtrate was separated by the separator 120.

The stillage with reduced oil via line 143 from the oil recovery centrifuge 145 can be introduced into one or more evaporators 150. The stillage with reduced oil can be further dewatered or dried in the evaporator 150 where water or other liquids can be further evaporated from the stillage with reduced oil to produce a syrup. The syrup can include, but is not limited to, minerals, sugars, starches, proteins, fibers, other components contained in water, or any mixture thereof. The syrup can be used alone or combined with other components or stream in the separation system 100 to produce various types of products. For example, the syrup via line 151 from the evaporator 150 can be transferred without any further processing to one or more storage containers 152 and can be used or sold as an independent product. In other examples, the syrup via line 153, 157, or 159 can be transferred from the evaporator 150 to one of several portions of the separation system 100 and combined with the fiber rich product, as will be further discussed and described below.

While the clarified stillage and the stillage with reduced oil can be subjected to the evaporators 140, 150, it should be understood that the number of evaporators and sets thereof can be varied depending on the particular application, conditions, and desired product compositions. In some configurations, each evaporator 140, 150 can be one evaporator or a plurality of evaporators, such as 2, 3, 4, 5, 6, or more evaporators coupled in series and in fluid communication with one another. For example, the evaporator 140 can have three or more evaporators and the evaporator 150 can also have three or more evaporators.

The fiber rich product via line 117 from the separator 116 can be transferred without any further processing via line 136 to one or more storage containers 138 and referred to as a wet fiber rich product that can be used or sold as an independent product. Alternatively, the fiber rich product via lines 117 and 154 can be transferred to one or more dryers 160. The fiber rich product can be further dried or dewatered by the dryer 160 to provide a dried fiber rich product that can be transferred via line 162 to one or more storage containers 164.

The dryer 160 can be or include one or more centrifuges (e.g., a decanter centrifuge), one or more ring dryers (e.g., P-ring dryers), one or more flash dryers, one or more fluid bed dryers, one or more heated air dryers, one or more heaters, one or more steam dryers (e.g., steam ring dryers, steam flash dryers, and/or steam tube dryers), one or more rotary dryers, one or more steam and rotary dryers (e.g., Swiss Combi's ecoDRY drying system), one or more superheated steam dryers, one or more spray dryers, one or more vacuum filtration dryers, one or more other drying devices, or any combination thereof to remove water and produce the dried protein product.

In other examples, the fiber rich product and the syrup can be combined together. For example, the fiber rich product via line 117 and the syrup via line 153 from the evaporator 150 can be combined and mixed in line 154 or other processing unit to produce a wet fiber rich product with syrup that can be transferred via line 155 to one or more storage containers 156.

In some examples, the wet fiber rich product with syrup via line 154 can be transferred to the dryer 160. The wet fiber rich product with syrup can be further dried or dewatered by dryer 160 to provide a dried fiber rich product with syrup that can be transferred via line 165 to one or more storage containers 168. The dried fiber rich product with syrup can be used or sold as an independent product.

Alternatively, in other examples, the fiber rich product and the syrup can be combined together in the dryer 160. For example, the fiber rich product via lines 117 and 154 and the syrup via line 157 from the evaporator 150 can be combined and mixed in dryer 160 to produce the wet fiber rich product with syrup that can be dried in the dryer 160 to produce the dried fiber rich product with syrup. The dried fiber rich product with syrup can be transferred from the dryer 160 via line 165 to the storage container 168. In other examples, the dried fiber rich product via line 162 from the dryer 160 and the syrup via line 159 from the evaporator 150 can be combined and mixed in line 167 or other processing unit to produce the dried fiber rich product with syrup that can be transferred via line 167 to the storage container 168.

Figure 2:
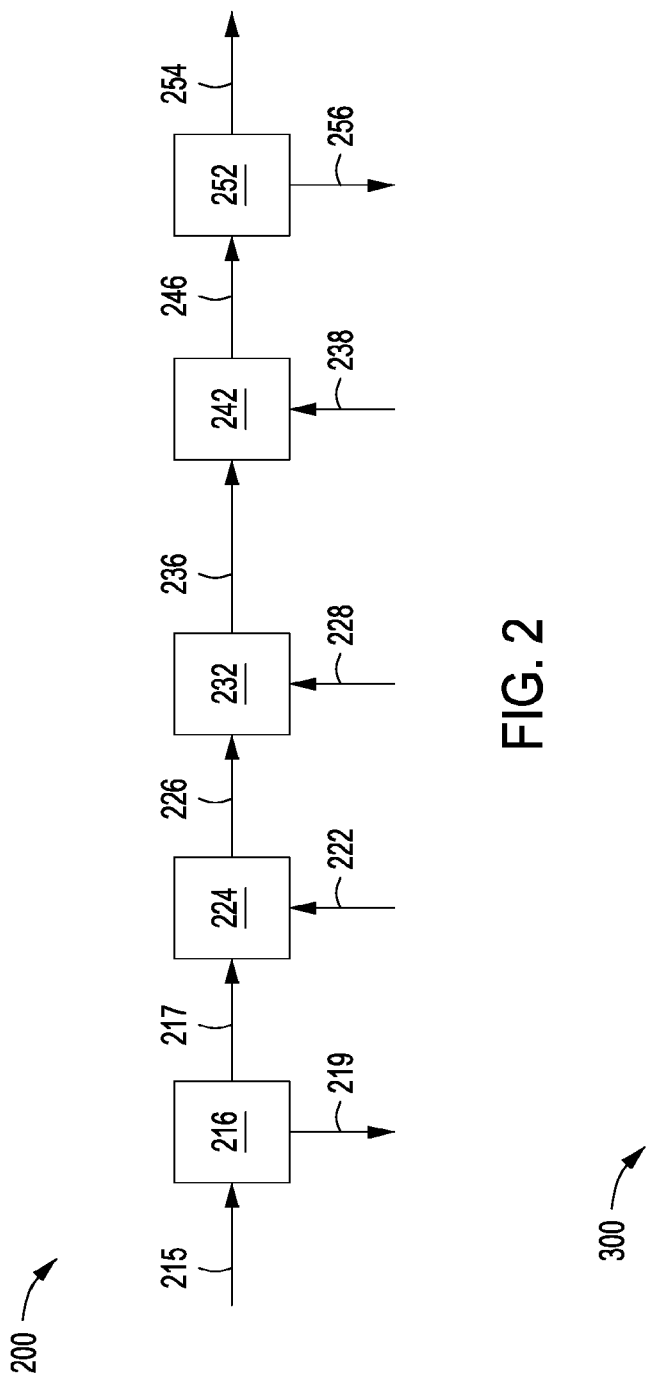
FIG. 2 depicts a schematic view of an illustrative system for producing ethanol from a fiber product recovered from a whole stillage, according to one or more embodiments described.

FIG. 2 depicts a schematic view of an illustrative system 200 for producing ethanol from a fiber product recovered from a whole stillage, according to one or more embodiments. A whole stillage via line 215 can be introduced to one or more separators 216. The whole stillage can be produced in the same or substantially the same way as the whole stillage in line 115 discussed and described above with reference to FIG. 1. The ground corn that can be processed to produce a fermentation mash that the whole stillage can be separated from can be ground with one or more disk mill fiberizers. The whole stillage can be contacted or otherwise processed in the separator 216 to separate or otherwise produce a fiber rich product via line 217 and a filtrate via line 219. The separator 216 can be or include any one or more of the separators 116 discussed and described above with reference to FIG. 1. For example, the separator 216 can be or include, but is not limited to, one or more pressure screens, one or more centrifuges (e.g., a filtration centrifuge such as those discussed and described in U.S. Pat. Nos. 8,813,973 and 8,778,433), one or more paddle screens, one or more fiber filters, one or more rotary drum screens, one or more rotary vacuum drum filters, one or more brush strainers, one or more vibratory separators, one or more centrifugal screeners, one or more linear motion screens, one or more vacu-deck screens, or any combination thereof. In some examples, the separator 216 can be or include one or more fiber filters. In other examples, the separator 216 can be or include one or more paddle screens.

In some examples, the filtrate in line 219 can be processed in the same or substantially the same manner as the filtrate in line 119 discussed and described above with reference to FIG. 1. The fiber rich product via line 217 can be introduced to one or more pretreatment vessels 224 to produce a pretreated fiber rich product via line 226. The pretreatment vessel 224 can be or include, for example, a slurry tank or a pressure vessel. The pretreatment vessel 224 can disrupt the structure of the fiber rich product to produce a fiber rich product that can be more readily accessible and digestible to hydrolysis with an enzyme, e.g., a cellulose enzyme. For example, hemicellulose can be converted to oligomers, xylose, and/or arabinose and the cellulose and/or hemicellulosic oligomers can be made more accessible and digestible to the cellulase enzyme.

In some examples, one or more acids and/or one or more bases via line 222 can be mixed, blended, combined, or otherwise contacted with the fiber rich product within the pretreatment vessel 224. In some examples, the fiber rich product and the acid and/or base can be heated to a temperature of about 50° C., about 75° C., or about 100° C., to about 115° C., about 125° C., about 150° C., about 175° C., about 200° C., or about 225° C. The fiber rich product and the acid and/or base can be heated for a time of about 10 minutes, about 30 minutes, or about 1 hour to about 2 hours, about 5 hours, or about 10 hours. Illustrative acids that can be contacted with the fiber rich product can include, but are not limited to, sulfuric acid, nitric acid, hydrochloric acid, phosphoric acid, strong acid resins, acetic acid, citric acid, trichloroacetic acid, or any mixture thereof. Illustrative bases that can be contacted with the fiber rich product can include, but are not limited to, ammonium hydroxide, potassium hydroxide, sodium hydroxide, calcium hydroxide, magnesium hydroxide, strong base resins, sodium carbonate, potassium carbonate, lime, or any mixture thereof. In some examples, the fiber rich product contacted with the acid and/or base can also be irradiated, e.g., microwaves and/or radio waves. In some examples, the fiber rich product, without being contacted with an acid or a base, can be irradiated, e.g., microwaves and/or radio waves. In some examples, the fiber rich product can be subjected to steam explosion, e.g., contact with steam at a temperature of about 160° C., to about 260° C., under a pressure of about 0.7 Mpa to about 5 Mpa, for a time of about 1 minute to about 20 minutes.

Other processes that can be used to produce the pretreated fiber rich product in lieu of or in addition to an acid and/or a base can include, but are not limited to, ionic liquid pretreatment; liquid hot water (LHW) pre-treatment; supercritical water; steam explosion; ammonia fiber explosion (AFEX); carbon dioxide explosion; contact with heteropolyacids, e.g., $H_5BW_{12}O_{40}$; ozonolysis; organosolvation treatment with an organic solvent such as acetone, methanol, ethanol, phenol, ethylene glycol, tetrahydrofuran, and/or tetrahydrofurfuryl; or any combination thereof.

The pretreated fiber rich product via line 226 can be introduced to one or more saccharification vessels 232. One or more enzymes via line 228 can also be introduced to the saccharification vessel 232. The pretreated fiber rich product can be contacted under conditions sufficient to produce a saccharification mash that can be recovered via line 236. During saccharification, the pretreated fiber rich product can be cooled and one or more enzymes, e.g., glucoamylase, can be added to hydrolyze maltodextrins and oligosaccharides into single glucose sugar molecules.

Illustrative enzymes can include, but are not limited to, one or more cellulases, one or more hemicellulases, or a mixture thereof. In some examples a cellulase and a hemicellulase can be used. The cellulase can include, but is not limited to, exo-glucanases, endo-gluconases, beta-glucosidase, and potentially some xylanase activity. The hemicellulase can include a number of different activities such as exo-xylanase, endo-xylanase, arabinose, esterase, and proteases. These enzyme mixtures are available commercially from Novozymes (Franklinton N.C.) and DuPont (Wilmington Del.). Commercially available enzymes that can be used can include, but are not limited to, ACCELLERASE® Trio; ACCELLERASE® 1500; ACCELLERASE® BG, OPTI-MASH®, and SPEZYME® CP (available from Dupont); CELLUCLAST® 1.5L; CELLIC® CTec2; CELLIC® CTec3, CELLIC® CTec4, HTec1, HTec2, HTec3 (available from Novozymes); ROHAMENT® CL, ROHAMENT® CEP, ROHALASEV BXL, ROHALASE® SEP (available from AB Enzymes); SZM XC-150 (available from CTE-Global), and CODEXYME® 4 (available from Codexis).

The saccharification mash via line 236 can be introduced to one or more fermenters 242. One or more strains of yeast, e.g., *Saccharomyces cerevisae, Pichia Stipitis*, and/or *Candida utilis*, can be introduced via line 238 to the fermenter 242 to initiate fermentation of the saccharification mash and produce a fermented product that can include ethanol and a stillage protein product that can be recovered via line 246. The yeast can ferment, metabolize, digest, or otherwise convert the sugars in the saccharification mash with yeast into ethanol and carbon dioxide. The saccharification mash can be heated or otherwise maintained at a temperature of about 28° C., to about 55° C. during the fermentation.

The fermented product via line 246 can be introduced to one or more distillers 252 where the fermented product can be heated to vaporize at least a portion of the ethanol. The distiller 252 can be or include, but is not limited to, one or more distillation columns, distillation trains, one or more condensers, or other devices configured to vaporize the ethanol and to condense the vaporized ethanol. The ethanol can be distilled or otherwise separated from the fermented product within the distiller 252 and recovered via line 254. The stillage protein product can be recovered via line 256.

Figure 3:
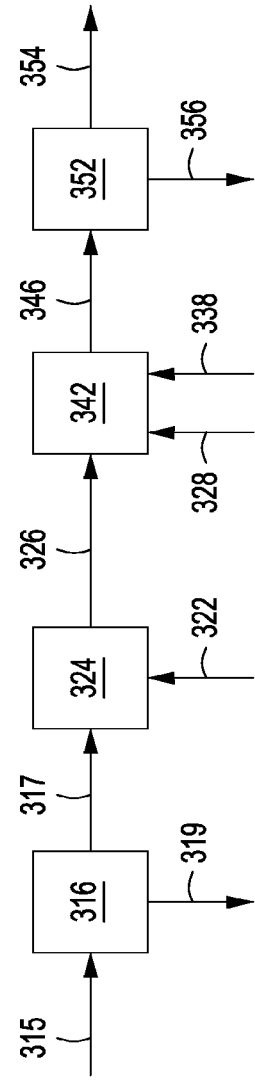
FIG. 3 depicts a schematic view of another illustrative system for producing ethanol from a fiber product recovered from a whole stillage, according to one or more embodiments described.
Figure 4:
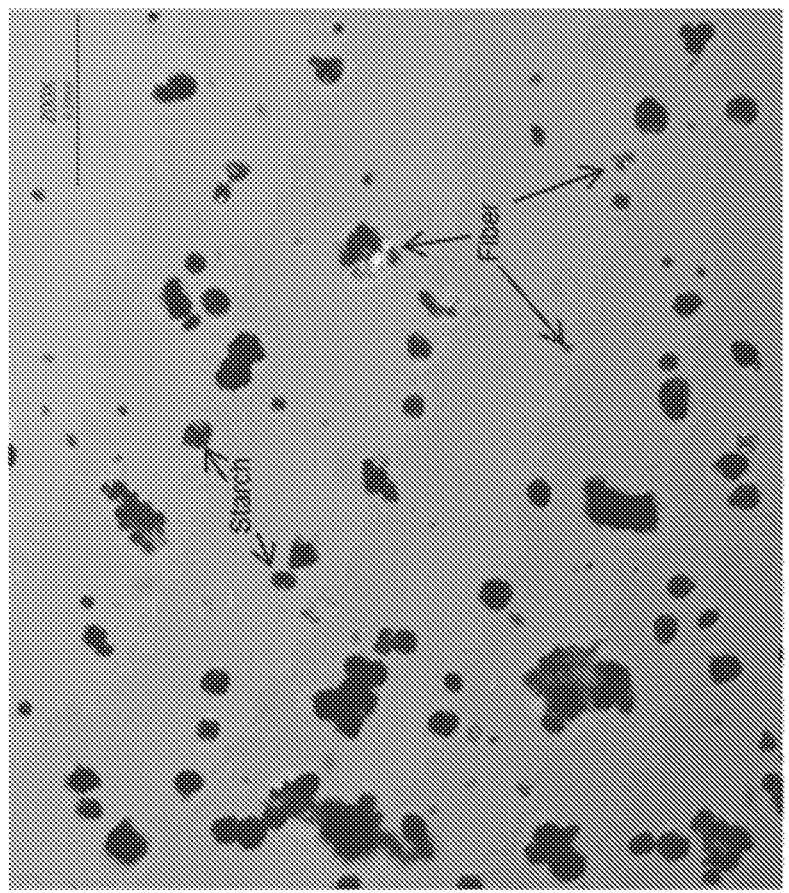
FIG. 4 is an optical microscope image of hammer milled corn (Comparative Example 1) at a magnification of 10×.

FIG. 3 depicts a schematic view of another illustrative system 300 for producing ethanol from a fiber product recovered from a whole stillage, according to one or more embodiments. A whole stillage via line 315 can be introduced to one or more separators 316. The whole stillage can be produced in the same or substantially the same way as the whole stillage in line 315 discussed and described above with reference to FIG. 1. The whole stillage can be contacted or otherwise processed in the separator 316 to separate or otherwise produce a fiber rich product via line 317 and a filtrate via line 319. In some examples, the filtrate in line 319 can be processed in the same or substantially the same manner as the filtrate in line 119 discussed and described above with reference to FIG. 1. The fiber rich product via line 317 can be introduced to one or more pretreatment vessels 324 to produce a pretreated fiber rich product via line 326. The pretreatment vessel 324 can be or include, for example, a slurry tank or a pressure vessel. The pretreatment vessel 324 can disrupt the structure of the fiber rich product to produce a fiber rich product that can be more readily accessible and digestible to hydrolysis with an enzyme, e.g., a cellulose enzyme. For example, hemicellulose can be converted to oligomers, xylose, and/or arabinose and the cellulose and/or hemicellulosic oligomers can be made more accessible and digestible to the cellulase enzyme.

In some examples, one or more acids and/or one or more bases via line 322 can be mixed, blended, combined, or otherwise contacted with the fiber rich product within the pretreatment vessel 324. In some examples, the fiber rich product and the acid and/or base can be heated to a temperature of about 50° C., about 75° C., or about 100° C., to about 115° C., about 125° C., about 150° C., about 175° C., about 200° C., or about 225° C. The fiber rich product and the acid and/or base can be heated for a time of about 10 minutes, about 30 minutes, or about 1 hour to about 2 hours, about 5 hours, or about 10 hours. Illustrative acids that can be contacted with the fiber rich product can include, but are not limited to, sulfuric acid, nitric acid, hydrochloric acid, phosphoric acid, or any mixture thereof. Illustrative bases that can be contacted with the fiber rich product can include, but are not limited to, ammonium hydroxide, potassium hydroxide, sodium hydroxide, calcium hydroxide, or any mixture thereof. In some examples, the fiber rich product and the acid and/or base can also be irradiated, e.g., microwaves and/or radio waves. In some examples, the fiber rich product can be subjected to steam explosion, e.g., contact with steam at a temperature of about 160° C., to about 260° C., under a pressure of about 0.7 Mpa to about 5 Mpa, for a time of about 1 minute to about 20 minutes.

Other processes that can be used to produce the pretreated fiber rich product can include, but are not limited to, liquid hot water (LHW) pre-treatment; ammonia fiber explosion (AFEX); carbon dioxide explosion; contact with heteropolyacids, e.g., $H_5BW_{12}O_{40}$; ozonolysis; organosolvation treatment with an organic solvent such as acetone, methanol, ethanol, phenol, ethylene glycol, and/or tetrahydrofurfuryl; or any combination thereof.

The pretreated fiber rich product via line 326 can be introduced to one or more fermenters 342. The pretreated fiber rich product can be subjected to simultaneous saccharification and fermentation (SSF) within the fermenter 342. For example, one or more enzymes via line 328 and one or more yeasts rains of yeast, e.g., *Saccharomyces cerevisae, Pichia stipitis*, and/or *Candida utilis*, via line 338 can also be introduced to the fermenter 342 to produce a fermented product. In some examples, the enzyme via line 328 and the yeast via line 338 can be introduced to the fermenter 342 at the same time. Illustrative enzymes can include, but are not limited to, one or more cellulases, one or more hemicellulases, or a mixture thereof. In some examples a cellulase and a hemicellulase can be used. The cellulase can include, but is not limited to, exo-glucanases, endo-gluconases, beta-glucosidase, and potentially some xylanase activity. The hemicellulase can include a number of different activities such as exo-xylanase, endo-xylanase, arabinose, esterase, and proteases. These enzyme mixtures are available commercially from Novozymes (Franklinton N.C.) and DuPont (Wilmington Del.).

In other examples, the enzyme via line 328 can be introduced to the fermenter 342 before the yeast via line 338. The saccharification of the pretreated fiber rich product can hydrolyze maltodextrins and oligosaccharides into single glucose sugar molecules. The fermentation of the fiber rich product and/or the saccharification mash can produce additional ethanol and a stillage protein product that can be recovered as the fermented product via line 346 from the fermenter 342. The fiber rich product and/or saccharification mash can be heated or otherwise maintained at a temperature of about 28° C., to about 55° C. during saccharification and fermentation.

The fermented product via line 346 can be introduced to one or more distillers 352 where the fermented product can be heated to vaporize at least a portion of the ethanol. The distiller 352 can be or include, but is not limited to, one or more distillation columns, distillation trains, one or more condensers, or other devices configured to vaporize the ethanol and to condense the vaporized ethanol. The ethanol can be distilled or otherwise separated from the fermented product within the distiller 352 and recovered via line 354. The stillage protein product can be recovered via line 356.

Returning to the fiber rich products in lines 217 and 317, the fiber rich products can include inorganic compounds (commonly referred to as ash); structural protein; extractives such as fats and glycerol; acetate; lignin; C6 polysaccharides; C5 polysaccharides; or any mixture thereof. In some examples, the fiber rich products in lines 217 and 317 can include at least 20 wt %, at least 21 wt %, at least 22 wt %, at least 23 wt %, at least 24 wt %, at least 25 wt %, at least 26 wt %, at least 27 wt %, at least 28 wt %, at least 29 wt %, or at least 30 wt % of C6 polysaccharides, based on a dried weight of the fiber rich products. In some examples, the fiber rich products in lines 217 and 317 can include at least 20 wt %, at least 21 wt %, at least 22 wt %, at least 23 wt %, at least 24 wt %, at least 25 wt %, at least 26 wt %, at least 27 wt %, at least 28 wt %, at least 29 wt %, at least 30 wt %, at least 31 wt %, at least 32 wt %, at least 33 wt %, at least 34 wt %, at least 35 wt %, at least 36 wt %, at least 37 wt %, at least 38 wt %, at least 39 wt %, at least 40 wt %, at least 41 wt %, or at least 42 wt % of C5 polysaccharides, based on the dried weight of the fiber rich products. In some examples, the fiber rich products in lines 217 and 317 can include about 25 wt % to about 35 wt % of C6 polysaccharides and about 23 wt % to about 45 wt % of C5 polysaccharides, based on the dried weight of the fiber rich products. In some examples, the fiber rich products in lines 217 and 317 can include about 27 wt % to about 30 wt % of C6 polysaccharides and about 24 wt % to about 28 wt % of C5 polysaccharides, based on the dried weight of the fiber rich products. In other examples, the fiber rich products in lines 217 and 317 can include about 28 wt % to about 33 wt % of C6 polysaccharides and about 38 wt % to about 45 wt % of C5 polysaccharides, based on the dried weight of the fiber rich products. In some examples, the fiber rich products in lines 217 and 317 can include at least 20 wt % to about 35 wt % of C6 polysaccharides and at least 20 wt % to about 45 wt % of C5 polysaccharides, based on the dried weight of the fiber rich products.

In some examples, the fiber rich products in lines 217 and 317 can include at least 20 wt %, at least 21 wt %, at least 22 wt %, at least 23 wt %, at least 24 wt %, at least 25 wt %, at least 26 wt %, at least 27 wt %, at least 28 wt %, at least 29 wt %, or at least 30 wt % of a combined amount of glucan, galactan, mannan, and starch, based on a dried weight of the fiber rich products. In some examples, the fiber rich products in lines 217 and 317 can include at least 20 wt %, at least 21 wt %, at least 22 wt %, at least 23 wt %, at least 24 wt %, at least 25 wt %, at least 26 wt %, at least 27 wt %, at least 28 wt %, at least 29 wt %, at least 30 wt %, at least 31 wt %, at least 32 wt %, at least 33 wt %, at least 34 wt %, at least 35 wt %, at least 36 wt %, at least 37 wt %, at least 38 wt %, at least 39 wt %, at least 40 wt %, at least 41 wt %, or at least 42 wt % of a combined amount of xylan and arabinan, based on the dried weight of the fiber rich products. In some examples, the fiber rich products in lines 217 and 317 can include about 25 wt % to about 35 wt % of a combined amount of glucan, galactan, mannan, and starch and about 23 wt % to about 45 wt % of a combined amount of xylan and arabinan, based on the dried weight of the fiber rich products. In some examples, the fiber rich products in lines 217 and 317 can include about 27 wt % to about 30 wt % of a combined amount of glucan, galactan, mannan, and starch and about 24 wt % to about 28 wt % of a combined amount of xylan and arabinan, based on the dried weight of the fiber rich products. In other examples, the fiber rich products in lines 217 and 317 can include about 28 wt % to about 33 wt % of a combined amount of glucan, galactan, mannan, and starch and about 38 wt % to about 45 wt % of a combined amount of xylan and arabinan, based on the dried weight of the fiber rich products. In some examples, the fiber rich products in lines 217 and 317 can include at least 20 wt % to about 35 wt % of a combined amount of glucan, galactan, mannan, and starch and at least 20 wt % to about 45 wt % of a combined amount of xylan and arabinan, based on the dried weight of the fiber rich products.

In some examples, the fiber rich products in lines 217 and 317 can include about 12 wt %, about 13 wt %, about 14 wt %, about 15 wt %, about 16 wt %, about 17 wt %, or about 18 wt % to about 19 wt %, about 20 wt %, about 21 wt %, about 22 wt %, about 23 wt %, about 24 wt %, or about 25 wt % of glucan, based on the dried weight of the fiber rich products. In some examples, the fiber rich products in lines 217 and 317 can include about 2 wt %, about 3 wt %, about 4 wt %, about 4.5 wt %, or about 5 w t % to about 6 wt %, about 6.5 wt %, about 7 wt %, about 7.5 wt %, about 8 wt %, about 8.5 wt %, about 9 wt %, about 9.5 wt %, or about 10 wt % of galactan, based on the dried weight of the fiber rich products. In some examples, the fiber rich products in lines 217 and 317 can include about 1 wt %, about 1.3 wt %, about 1.5 wt %, about 1.7 wt %, about 2 wt %, about 2.3 wt %, or about 2.5 wt % to about 2.7 wt %, about 3 wt %, about 3.3 wt %, about 3.5 wt %, about 3.7 wt %, about 4 wt %, about 4.3 wt %, about 4.5 wt %, about 4.7 wt %, or about 5 wt % of starch, based on the dried weight of the fiber rich products. In some examples, the fiber rich products in lines 217 and 317 can include about 10 wt %, about 12 wt %, about 14 wt %, about 16 wt %, or about 18 wt % to about 20 wt %, about 22 wt %, about 24 wt %, about 26 wt %, or about 28 wt % of xylan, based on the dried weight of the fiber rich products. In some examples, the fiber rich products in lines 217 and 317 can include about 7 wt %, about 8 wt %, about 9 wt %, or about 10 wt % to about 12 wt %, about 14 wt %, about 16 wt %, about 17 wt %, about 18 wt %, about 19 wt %, or about 20 wt % of arabinan, based on the dried weight of the fiber rich products. In some examples, the fiber rich products in lines 217 and 317 can include about 12 wt % to about 22 wt % of glucan, about 11 wt % to about 28 wt % of xylan, about 2.5 wt % to about 8 wt % of galactan, about 7 wt % to about 20 wt % of arabinan, and about 2 wt % to about 5 wt % of starch, based on the dried weight of the fiber products. In other examples, the fiber rich products in lines 217 and 317 can include about 16 wt % to about 22 wt % of glucan, about 14 wt % to about 28 wt % of xylan, about 5 wt % to about 8 wt % of galactan, about 8 wt % to about 20 wt % of arabinan, and about 3.7 wt % to about 5 wt % of starch, based on the dried weight of the fiber products. In some examples, the fiber rich products in lines 217 and 317 can include at least 16 wt % of glucan, at least 15 wt % of xylan, at least 5 wt % of galactan, at least 9 wt % of arabinan, and at least 2 wt % of starch, based on the dried weight of the fiber products. In some examples, the fiber rich products in lines 217 and 317 can include at least 18 wt % of glucan, at least 16 wt % of xylan, at least 6 wt % of galactan, at least 9 wt % of arabinan, and at least 2 wt % of starch, based on the dried weight of the fiber products. In some example, the fiber rich products in lines 217 and 317 can include at least 20 wt % of glucan, at least 20 wt % of xylan, at least 6 wt % of galactan, at least 15 wt % of arabinan, and at least 2 wt % of starch, based on the dried weight of the fiber products.

In some examples, the fiber rich products in lines 217 and 317 can include about 10 wt %, about 13 wt %, or about 15 wt % to about 20 wt %, about 23 wt %, about 25 wt %, or about 27 wt % of structural protein based on a dried weight of the fiber rich products. In other examples, the fiber rich products in lines 217 and 317 can include less than 20 wt %, less than 19 wt %, less than 18 wt %, less than 17 wt %, less than 16 wt %, less than 15 wt %, or less than 14 wt % of structural protein, based on a dried weight of the fiber rich products. In other examples, the fiber rich products in lines 217 and 317 can include at least 19 wt %, at least 20 wt %, at least 21 wt %, or at least 22 wt % to about 23 wt %, about 24 wt %, about 25 wt %, or about 27 wt % of structural protein, based on a dried weight of the fiber rich product.

In some examples, the fiber rich products in lines 217 and 317 can include less than 1.4 wt %, less than 1.3 wt %, less than 1.2 wt %, less than 1.1 wt %, less than 1 wt %, less than 0.9 wt %, less than 0.8 wt %, or less than 0.7 wt % of the inorganic compounds, based on a dried weight of the fiber rich products. In some examples, the fiber rich products in lines 217 and 317 can include less than 5 wt %, less than 4.5 wt %, less than 4 wt %, less than 3.5 wt %, less than 3 wt %, less than 2.5 wt % less than 2 wt %, or less than 1.7 wt % of the extractives. In some examples, the fiber rich products in lines 217 and 317 can include about 1.5 wt %, about 1.7 wt %, about 2 wt %, or about 2.3 wt % to about 2.7 wt %, about 3 wt %, about 3.5 wt %, or about 4 wt % of acetate, based on a dried weight of the fiber rich products. In some examples, the fiber rich products in lines 217 and 317 can include about 15 wt %, about 16 wt %, about 17 wt % or about 18 wt % to about 19 wt %, about 20 wt %, about 21 wt %, or about 22 wt % of lignin, based on a dried weight of the fiber rich products.

In some examples, the fiber rich products in lines 217 and 317 can include less than 1 wt % of the inorganic compounds, less than 2 wt % of the extractives, about 1.8 wt % to about 4 wt % of acetate, about 27 wt % to about 30 wt % of C6 polysaccharides, and about 24 wt % to about 28 wt % of C5 polysaccharides, based on a dried weight of the fiber rich products. In some examples, the fiber rich products in lines 217 and 317 can include less than 1 wt % of the inorganic compounds, about 20 wt % to about 26 wt % of structural protein, less than 2 wt % of the extractives, about 2 wt % to about 4 wt % of acetate, about 27 wt % to about 30 wt % of C6 polysaccharides, and about 24 wt % to about 28 wt % of C5 polysaccharides, based on a dried weight of the fiber rich products. In other examples, the fiber rich products in lines 217 and 317 can include less than 1 wt % of the inorganic compounds, less than 2 wt % of the extractives, about 1.8 wt % to about 4 wt % of acetate, about 20 wt % to about 25 wt % of structural protein, about 17 wt % to about 22 wt % of lignin, about 27 wt % to about 30 wt % of C6 polysaccharides, and about 24 wt % to about 28 wt % of C5 polysaccharides, based on a dried weight of the fiber rich products.

In some examples, the fiber rich products in lines 217 and 317 can include less than 1 wt % of inorganic compounds, less than 1 wt % of extractives, about 1.5 wt % to about 3 no of acetate, about 28 wt % to about 33 wt % of C6 polysaccharides, and about 38 wt % to about 45 wt % of C5 polysaccharides, based on a dried weight of the fiber rich products. In other examples, the fiber rich products in lines 217 and 317 can include less than 1 wt % of inorganic compounds, about 10 wt % to about 16 wt % of structural protein, less than 1 wt % of extractives, about 1.5 wt % to about 3 wt % of acetate, about 28 wt % to about 33 wt % of C6 polysaccharides, and about 38 wt % to about 45 wt % of C5 polysaccharides, based on a dried weight of the fiber rich products. In other examples, the fiber rich products in lines 217 and 317 can include less than 1 wt % of inorganic compounds, about 10 wt % to about 16 wt % of structural protein, less than 1 wt % of extractives, about 1.5 wt % to about 3 wt % of acetate, about 17 wt % to about 22 wt % of lignin, about 28 wt % to about 33 wt % of C6 polysaccharides, and about 38 wt % to about 45 wt % of C5 polysaccharides, based on a dried weight of the fiber rich products.

The dried weight or solids weight of the fiber rich products, the stillage protein products, and other products can be determined via standard tests used in the industry. For example, the dried weight or solids weight of the fiber rich product, the stillage protein product, or other product can be determined according to the National Renewable Energy Laboratory (NREL) test. "Determination of Total Solids in Biomass and Total Dissolved Solids in Liquid Process Samples", Version 2008. The amount of the inorganic compounds, structural protein, extractives, acetate, lignin. C6 polysaccharides, and C5 polysaccharides in the fiber rich products can also be determined via standard tests used in the industry. For example, the amount of inorganic compounds in the fiber rich products can be determined according to the NREL Chemical Analysis and Standard Testing Procedure. "Determination of Ash in Biomass", Version 2005. The amount of structural protein in the fiber rich products can be determined according to the NREL Chemical Analysis and Standard Testing Procedure. "Determination of Protein Content in Biomass", Version 2008. The amount of extractives in the fiber rich products can be determined according to the NREL Chemical Analysis and Standard Testing Procedure. "Determination of Extractives in Biomass", Version 2005. The amount of acetate, lignin. C6 polysaccharides, and C5 polysaccharides in the fiber rich products can be determined according to the NREL Chemical Analysis and Standard Testing Procedure. "Determination of Structural Carbohydrates and Lignin in Biomass", Version 2012. The amount of starch in the fiber rich products can be determined according to the NREL Chemical Analysis and Standard Testing Procedure, "Determination of Starch in Solid Biomass Sample", Version 2005.

Other standardized tests that can be used to determine the amount of C6 polysaccharides. C5 polysaccharides, and starch can also be used. For example, rather than using the NREL Chemical Analysis and Standard Test Procedure, "Determination of Structural Carbohydrates and Lignin in Biomass", Version 2012 to determine the amounts of any C6 polysaccharides, e.g., glucan, galactan, mannan, and C5 polysaccharides, e.g., xylan and arabinan, in the fiber rich products in lines 217 and 317, an ASTM test procedure can be used. More particularly, the test procedure outlined in ASTM E1758-01 (2015) can be used to determine the amounts of any C6 polysaccharides and/or C5 polysaccharides in the fiber rich products in lines 217 and 317. In other examples, rather than using the NREL Chemical Analysis Standard Test Procedure, "Determination of Starch in Solid Biomass Sample", Version 2005 to determine the amount of starch in the fiber rich products in lines 217 and 317, an AOAC, AACC, and/or ICC test procedure can be used. More particularly, in other examples the test procedures outlined in AOAC Method 996.11. AACC Method 76.13, and/or ICC Standard Method No. 168 can be used to determine the amount of starch in the fiber rich products in lines 217 and 317. Accordingly, it should be understood that the amount of C6 polysaccharides, C5 polysaccharides, starch, and other components in the fiber rich products in lines 217 and 317 can be determined using any combination of these standardized tests or any other standardized test capable of determining the amount of any one or more of the carbohydrates or starch in the fiber rich products in lines 217 and 317.

In some examples, the fiber rich products in lines 217 and 317 can have an ethanol potential of at least 90 gallons of ethanol per 1,000 kilograms of the fiber rich product, at least 91 gallons of ethanol per 1,000 kilograms of the fiber rich product, at least 92 gallons of ethanol per 1,000 kilograms of the fiber rich product, at least 93 gallons of ethanol per 1,000 kilograms of the fiber rich product, at least 94 gallons of ethanol per 1,000 kilograms of the fiber rich product, at least 95 gallons of ethanol per 1,000 kilograms of the fiber rich product, at least 96 gallons of ethanol per 1,000 kilograms of the Fiber rich product, at least 97 gallons of ethanol per 1,000 kilograms of the fiber rich product, at least 98 gallons of ethanol per 1,000 kilograms of the fiber rich product, at least 99 gallons of ethanol per 1,000 kilograms of the fiber rich product, at least 100 gallons of ethanol per 1,000 kilograms of the Fiber rich product, at least 101 gallons of ethanol per 1,000 kilograms of the fiber rich product, at least 102 gallons of ethanol per 1,000 kilograms of the fiber rich product, at least 103 gallons of ethanol per 1,000 kilograms of the fiber rich product, at least 104 gallons of ethanol per 1,000 kilograms of the fiber rich product, at least 105 gallons of ethanol per 1,000 kilograms of the fiber rich product, at least 107, at least 110 gallons of ethanol per 1,000 kilograms of the fiber rich product, at least 115 gallons of ethanol per 1,000 kilograms of the fiber rich product, at least 120 gallons of ethanol per 1,000 kilograms of the fiber rich product, at least 125 gallons of ethanol per 1,000 kilograms of the fiber rich product, at least 130 gallons of ethanol per 1,000 kilograms of the fiber rich product, at least 135 gallons of ethanol per 1,000 kilograms of the fiber rich product, or at least 140 gallons of ethanol per 1,000 kilograms of the fiber rich product. For example, the fiber rich products in lines 217 and 317 can have an ethanol potential of about 92 gallons of ethanol per 1,000 kilograms of the fiber rich product, about 96 gallons of ethanol per 1,000 kilograms of the fiber rich product, about 99 gallons of ethanol per 1,000 kilograms of the fiber rich product, about 103 gallons of ethanol per 1,000 kilograms of the fiber rich product, or about 105 gallons of ethanol per 1,000 kilograms of the fiber rich product to about 130 gallons of ethanol per 1,000 kilograms of the fiber rich product, about 135 gallons of ethanol per 1,000 kilograms of the fiber rich product, about 140 gallons of ethanol per 1,000 kilograms of the fiber rich product, about 145 gallons of ethanol per 1,000 kilograms of the fiber rich product, about 150 gallons of ethanol per 1,000 kilograms of the fiber rich product, or about 155 gallons of ethanol per 1,000 kilograms of the fiber rich product. In another example, the fiber rich products in lines 217 and 317 can have an ethanol potential of about 90 gallons of ethanol per 1,000 kilograms of the fiber rich product to about 160 gallons of ethanol per 1,000 kilograms of the fiber rich product, about 90 gallons of ethanol per 1,000 kilograms of the fiber rich product to about 145 gallons of ethanol per 1,000 kilograms of the fiber rich product, about 100 gallons of ethanol per 1,000 kilograms of the fiber rich product to about 110 gallons of ethanol per 1,000 kilograms of the fiber rich product, or about 130 gallons of ethanol per 1,000 kilograms of the fiber rich product to about 145 gallons of ethanol per 1,000 kilograms of the fiber rich product. The ethanol potential of the fiber rich product, as discussed and described herein, is on a dry matter basis. i.e., based on a dried weight of the fiber rich product.

As used herein, the "ethanol potential" of the fiber rich product is measured in gallons of ethanol per 1,000 kilograms of the fiber rich product and is determined according to the following procedure. The extractives are removed from the fiber rich product as outlined in the NREL Chemical Analysis and Standard Test Procedure, "Determination of Extractives in Bimass", Version 2005. After the extractives are removed, water is removed from the fiber rich product as outlined in the NREL Chemical Analysis and Standard Test Procedure. "Determination of Total Solids in Biomass", Version 2008. The amounts of any glucan, any xylan, any galactan, any arabinan, and any mannan in the fiber rich product, after removing the extractives and the water, are determined as outlined in the NREL Chemical Analysis and Standard Test Procedure. "Determination of Structural Carbohydrates and Lignin in Biomass", Version 2012. The amount of any starch in the fiber rich product, after removing the extractives and the water, is determined as outlined in the NREL Chemical Analysis Standard Test Procedure, "Determination of Starch in Solid Biomass Sample", Version 2005.

The amounts (wt %) of any glucan, any galactan, any mannan, and any starch are multiplied by 1,000 kg to determine the amount of any glucan, galactan, mannan, and starch in kilograms per 1,000 kg of the fiber rich product (FRP). The mass (kg) of the glucan, galactan, mannan, and starch per 1,000 kg of the FRP are converted to mass (kg) monosaccharides per 1,000 kg of the FRP by multiplying the mass of the glucan, galactan, mannan, and starch by 1.11 to account for the molecule of water that adds to the polysaccharides when the sugar monomers are hydrolyzed from the polysaccharides. The mass (kg) of the monosaccharides per 1,000 kg of the FRP is multiplied by 0.51 (conversion of kilograms sugar to kilograms ethanol assuming 100% of theoretical yield). The kilograms of ethanol per 1,000 kg of the FRP is converted to liters (L) per 1,000 kg of the FRP by dividing the kilograms of ethanol by the density of ethanol (0.789 kg/L). The liters of ethanol per 1,000 kg of the FRP is converted to gallons of ethanol per 1,000 kg of the FRP by dividing the liters of ethanol by 3.789.

The amounts (wt %) of any xylan and any arabinan are multiplied by 1,000 kg to determine the amount of any xylan and any arabinan in kilograms per 1,000 kg of the FRP. The mass (kg) of the xylan and arabinan per 1,000 kg of the FRP are converted to mass (kg) of monosaccharides per 1,000 kg of the FRP by multiplying the mass fraction by 1.136 to account for the molecule of water that adds to the polysaccharides when the sugar monomers are hydrolyzed from the polysaccharides. The mass (kg) of monosaccharides per 1,000 kg of the FRP is multiplied by 0.51 (conversion of kilograms sugar to kilograms ethanol assuming 100% of theoretical yield). The kilograms of ethanol per 1,000 kg of the FRP is converted to liters (L) per 1,000 kg of the FRP by dividing the kilograms of ethanol by the density of ethanol (0.789 kg/L). The liters of ethanol per 1,000 kg of the FRP is converted to gallons of ethanol per 1,000 kg of the FRP by dividing the liters of ethanol by 3.789.

The theoretical amount of ethanol per 1,000 kilograms of the FRP, i.e., the ethanol potential, that can potentially be produced from the glucan, galactan, mannan, and starch and the xylan and arabinan are added to provide the ethanol potential of the fiber rich products. The ethanol potential of the fiber rich products in lines 217 and 317 is limited to any glucan, any galactan, any mannan, any starch, any xylan, and any arabinan present therein and does not include any additional C5 polysaccharides and any additional C6 polysaccharides.

Returning to the saccharification mash in line 236 and the saccharification mash that can be produced within the fermenter 342 via the simultaneous saccharification and fermentation process, in some examples, if the fiber rich product is contacted with an acid to produce the pretreated fiber rich product, the saccharification mash in line 236 and/or the saccharification mash produced within the fermenter 342 can be fermented in the fermenter 242 and 342, respectively, to produce at least 25 gallons of ethanol per 1,000 kilograms of the saccharification mash, at least 30 gallons of ethanol per 1,000 kilograms of the saccharification mash, at least 35 gallons of ethanol per 1,000 kilograms of the saccharification mash, at least 40 gallons of ethanol per 1,000 kilograms of the saccharification mash, at least 45 gallons of ethanol per 1,000 kilograms of the saccharification mash, at least 50 gallons of ethanol per 1,000 kilograms of the saccharification mash, at least 60 gallons of ethanol per 1,000 kilograms of the saccharification mash, or at least 65 gallons of ethanol per 1,000 kilograms of the saccharification mash. For example, if the fiber rich product is contacted with an acid to produce the pretreated fiber rich product, the saccharification mash in line 236 and/or the saccharification mash produced within the fermenter 342 can be fermented in the fermenter 242 and 342, respectively, to produce about 25 gallons of ethanol per 1,000 kilograms of the saccharification mash, about 30 gallons of ethanol per 1,000 kilograms of the saccharification mash, about 35 gallons of ethanol per 1,000 kilograms of the saccharification mash, about 40 gallons of ethanol per 1,000 kilograms of the saccharification mash, or about 45 gallons of ethanol per 1,000 kilograms of the saccharification mash to about 50 gallons of ethanol per 1,000 kilograms of the saccharification mash, about 55 gallons of ethanol per 1,000 kilograms of the saccharification mash, about 60 gallons of ethanol per 1,000 kilograms of the saccharification mash, or about 65 gallons of ethanol per 1,000 kilograms of the saccharification mash.

In some examples, if the fiber rich product is contacted with a base to produce the pretreated fiber rich product, the saccharification mash in line 236 and/or the saccharification mash produced within the fermenter 342 can be fermented in the fermenter 242 and 342, respectively, to produce at least 25 gallons of ethanol per 1,000 kilograms of the saccharification mash, at least 30 gallons of ethanol per 1,000 kilograms of the saccharification mash, at least 35 gallons of ethanol per 1,000 kilograms of the saccharification mash, at least 40 gallons of ethanol per 1,000 kilograms of the saccharification mash, at least 45 gallons of ethanol per 1,000 kilograms of the saccharification mash, at least 50 gallons of ethanol per 1,000 kilograms of the saccharification mash, at least 55 gallons of ethanol per 1,000 kilograms of the saccharification mash, at least 60 gallons of ethanol per 1,000 kilograms of the saccharification mash, or at least 65 gallons of ethanol per 1,000 kilograms of the saccharification mash. For example, if the fiber rich product is contacted with abase to produce the pretreated fiber rich product, the saccharification mash in line 236 and/or the saccharification mash produced within the fermenter 342 can be fermented in the fermenter 242 and 342, respectively, to produce about 25 gallons of ethanol per 1,000 kilograms of the saccharification mash, about 30 gallons of ethanol per 1,000 kilograms of the saccharification mash, about 35 gallons of ethanol per 1,000 kilograms of the saccharification mash, about 40 gallons of ethanol per 1,000 kilograms of the saccharification mash, or about 45 gallons of ethanol per 1,000 kilograms of the saccharification mash to about 50 gallons of ethanol per 1,000 kilograms of the saccharification mash, about 55 gallons of ethanol per 1,000 kilograms of the saccharification mash, about 60 gallons of ethanol per 1,000 kilograms of the saccharification mash, or about 65 gallons of ethanol per 1,000 kilograms of the saccharification mash. The amount of ethanol produced per 1,000 kilograms of the saccharification mash, as discussed and described herein, is on a dry matter basis. i.e., based on a dried weight of the saccharification mash.

Returning to the stillage protein products in lines 256 and/or 356, the stillage protein products can include, but are not limited to, protein, fat, ash, neutral detergent fibers, acid detergent fibers, yeast, or any mixture thereof. In some examples, the stillage protein products in lines 256 and 356 can include about 40 wt %, about 45 wt %, or about 50 wt % to about 60 wt %, about 70 wt %, or about 80 wt % of protein, based on a dry weight of the stillage protein product. In some examples, each stillage protein products in lines 256 and 356 can include about 2 wt %, about 5 wt %, or about 8 wt % of fat to about 12 wt %, about 17 wt %, or about 20 wt % of the fat, based on the dry weight of the stillage protein product. In some examples, the stillage protein products in lines 256 and 356 can include about 0.5 wt %, about 1 wt %, or about 2 wt % to about 3 wt %, about 4 wt %, or about 5 wt % of ash, based on the dry weight of the stillage protein product. In some examples, the stillage protein products in lines 256 and 356 can include about 1 wt %, about 5 wt %, about 10 wt %, or about 15 wt % to about 20 wt %, about 25 wt %, or about 30 wt % of the neutral detergent fibers, based on the dry weight of the stillage protein product. In some examples, the stillage protein products in lines 256 and 356 can include about 1 wt %, about 2 wt %, or about 5 wt % to about 8 wt %, about 10 wt %, or about 15 wt % of acid detergent fibers, based on the dry weight of the stillage protein product. In some examples, the stillage protein products in lines 256 and 356 can include about 15 wt %, about 17 wt %, about 20 wt %, or about 23 wt % to about 25 wt %, about 27 wt %, about 30 wt %, about 33 wt %, or about 35 wt % of yeast, based on the dry weight of the stillage protein product. In other examples, the stillage protein products in lines 256 and 356 can include at least 15 wt %, at least 16 wt %, at least 17 wt % N, at least 18 wt %, at least 19 wt %, at least 20 wt %, at least 21 wt %, at least 22 wt %, at least 23 wt %, at least 24 wt %, or at least 25 wt % to about 26 wt %, about 27 wt %, about 28 wt %, about 29 wt %, about 30 wt %, about 31 wt %, about 32 wt %, about 33 wt %, about 34 wt %, or about 35 wt % of yeast, based on the dr weight of the stillage protein product. In some example, the stillage protein products in lines 256 and 356 can also include water. For example, the stillage protein products in lines 256 and 356 can include about 4 wt %, about 5 wt %, about 6 wt %, or about 7 wt % to about 8 wt %, about 10 wt %, about 12 wt % of water, or about 15 wt % of water, based on a total weight of the stillage protein product.

In some examples, the stillage protein products in lines 256 and 356 can include about 40 wt % to about 80 wt % of protein, about 3 wt % to about 20 wt % of fat, about 1 wt % to about 4 wt % of ash, about 2 wt % to about 30 wt % of neutral detergent fibers, about 1 wt % to about 15 wt % of acid detergent fibers, and about 15 wt % to about 35 wt % of yeast, based on dry weight of the stillage protein product. In some examples, the stillage protein products in lines 256 and 356 can include about 40 wt % to about 80 wt % of protein, about 3 wt % to about 20 wt % of fat, about 1 wt % to about 4 wt % of ash, about 2 wt % to about 30 wt % of neutral detergent fibers, about 2 wt % to about 12 wt % of acid detergent fibers, and about 18 wt % to about 32 wt % of yeast, based on dry weight of the stillage protein product, and about 4 wt % to about 15 wt % of water, based on a total weight of the stillage protein product. In some examples, the stillage protein products in lines 256 and 356 can include about 45 wt % to about 60 wt % of protein, about 2 wt % to about 8 wt % of fat, about 1 wt % to about 4 wt % of ash, about 2 wt % to about 12 wt % of neutral detergent fibers, about 5 wt % to about 8 wt % of acid detergent fibers, and about 20 wt % to about 30 wt % of yeast, based on dry weight of the stillage protein product. In some examples, the stillage protein products in lines 256 and 356 can include about 45 wt % to about 60 wt % of protein, about 2 wt % to about 8 wt % of fat, about 1 wt % to about 4 wt % of ash, about 2 wt % to about 12 wt % of neutral detergent fibers, about 1 wt % to about 15 wt % of acid detergent fibers, and about 20 wt % to about 30 wt % of yeast, based on dry weight of the stillage protein product, and about 5 wt % to about 12 wt % of water, based on a total weight of the stillage protein product. In other examples, the stillage protein products in lines 256 and 356 can include about 50 wt % to about 54 wt % of protein, about 3 wt % to about 6 wt % of fat, about 1 wt % to about 4 wt % of ash, about 4 wt % to about 10 wt % of neutral detergent fibers, about 3 wt % to about 12 wt % of acid detergent fibers, and about 20 wt % to about 30 wt % of yeast, based on dry weight of the stillage protein product. In other examples, the stillage protein products in lines 256 and 356 can include about 50 wt % to about 54 wt % of protein, about 3 wt % to about 6 wt % of fat, about 1 wt % to about 4 wt % of ash, about 4 wt % to about 10 wt % of neutral detergent fibers, about 5 wt % to about 15 wt % of acid detergent fibers, and about 20 wt % to about 30 wt % of yeast, based on dry weight of the stillage protein product, and about 5 wt % to about 12 wt % of water, based on a total weight of the stillage protein product. In other examples, the stillage protein products in lines 256 and 356 can include about 50 wt % to about 54 wt % of protein, about 3 wt % to about 5 wt % of fat, about 1 wt % to about 3 wt % of ash, about 6 wt % to about 7 wt % of neutral detergent fibers, about 5 wt % to about 8 wt % of acid detergent fibers, and about 20 wt % to about 30 wt % of yeast, based on dry weight of the stillage protein product. In other examples, the stillage protein products in lines 256 and 356 can include about 50 wt % to about 54 wt % of protein, about 3 wt % to about 5 wt % of fat, about 1 wt % to about 3 wt % of ash, and about 6 wt % to about 7 wt % of neutral detergent fibers, based on dry weight of the stillage protein product, and about 6 wt % to about 10 wt % of water, based on a total weight of the stillage protein product.

The protein in the stillage protein products can be determined according to the AOAC 990.03 (2000) test method. The fat in the stillage protein products can be determined according to the AOAC 920.39 (2000) test method. Ash is the inorganic residue (minerals) remaining after any water and organic matter have been removed by heating in a furnace. The amount of ash in the stillage protein products can be determined according to test method AOAC 945.02 (2000). The neutral detergent fiber (NDF) in the stillage protein products can be measured according to the Neutral Detergent Fiber in Feeds—Filter Bag Technique (for A200 and A2001), as developed and defined by Ankom Technology, and referred to as (NDF Method. Method 13, last revised on Sep. 21, 2016). The NDF is the residue remaining after digesting in a detergent solution. The fiber residues are predominantly hemicellulose, cellulose, and lignin. The acid detergent fiber (ADF) in the stillage protein products can be measured according to the Acid Detergent Fiber in Feeds—Filter Bag Technique (for A200 and A2001), as developed and defined by Ankom Technology, and referred to as (ADF Method, Method 12 last revised on Sep. 21, 2016). The ADF is the residue remaining after digesting with sulfuric acid and detergent solution. The fiber residues are predominantly cellulose and lignin. Any water or moisture in the stillage protein products can be determined according to test method AOAC 934.01 (2000) test method.

Ground Corn Product

Returning to the ground corn product in line 103, the ground corn product can be quantified by having a particle size distribution, such as by weight percent (wt %) and/or volume percent (vol %), for specified particle sizes. The particle size and the particle size distribution of the ground corn product can be analyzed or otherwise determined by various particle size analyzers, such as laser diffraction analyzers, static and/or dynamic light scattering analyzers, zeta potential analyzers, sieve shaker with graduation test, and others. Generally, the particle size distribution of the ground corn product by weight can be measured using sieves and the particle size distribution of the ground corn product by volume can be measured by laser diffraction, as further discussed and described below.

The particle size and the particle size distribution of the ground corn product by weight can be measured or otherwise determined with a sieve shaker, such as the RO-TAP® RX-29 sieve shaker, commercially available from W. S. Tyler Industrial Group. The sieves analysis can be performed according to the AOAC Official Method 965.22-1966. "Sorting Corn Grits—Sieving Method." available from AOAC International. Sieve sizes of 850 µm, 425 µm, 250 µm, 180 µm, 150 µm, and 105 µm can be used to categorize the particle size distribution of the ground corn product by weight.

The amount of the ground corn product that can have a particle size of less than 100 µm can be about 10 wt %, about 15 wt %, about 20 wt %, about 25 wt %, about 30 wt %, about 35 wt %, or about 40 wt % to about 45 wt %, about 50 wt %, about 55 wt %, about 60 wt %, about 65 wt %, about 70 wt %, about 75 wt %, or greater, as measured according to AOAC 965.22-1966. For example, about 10 wt % to about 68 wt %, about 32 wt % to about 68 wt %, about 41 wt % to about 66 wt %, about 32 wt % to about 62 wt %, or about 35 wt % to about 58 wt % of the ground corn product can have a particle size of less than 100 µm, as measured according to AOAC 965.22-1966. In some examples, greater than 10 wt %, greater than 15 wt %, greater than 20 wt %, greater than 25 wt %, greater than 30 wt %, greater than 35 wt %, greater than 40 wt %, greater than 45 wt %, greater than 50 wt %, greater than 55 wt % greater than 60 wt %, greater than 65 wt %, or greater than 70 wt % of the ground corn product can have a particle size of less than 100 µm, as measured according to AOAC 965.22-1966. In other examples, greater than 10 wt %, greater than 15 wt %, greater than 20 wt %, greater than 25 wt %, greater than 30 wt %, greater than 35 wt %, greater than 40 wt %, greater than 45 wt %, or greater than 50 wt % to about 55 wt %, about 60 wt %, about 65 wt %, or about 70 wt % of the ground corn product can have a particle size of less than 100 µm, as measured according to AOAC 965.22-1966.

The amount of the ground corn product that can have a particle size of 105 µm or less can be about 30 wt %, about 35 wt %, or about 40 wt % to about 45 wt %, about 50 wt %, about 55 wt %, about 60 wt %, about 65 wt %, about 70 wt %, about 75 wt %, or greater, as measured according to AOAC 965.22-1966. For example, about 32 wt % to about 68 wt %, about 41 wt % to about 66 wt %, about 32 wt % to about 62 wt %, or about 35 wt % to about 58 wt % of the ground corn product can have a particle size of 105 µm or less, as measured according to AOAC 965.22-1966. In some examples, greater than 30 wt %, greater than 35 wt %, greater than 40 wt %, greater than 45 wt %, greater than 50 wt %, greater than 55 wt %, greater than 60 wt %, greater than 65 wt %, or greater than 70 wt % of the ground corn product can have a particle size of 105 µm or less, as measured according to AOAC 965.22-1966. In other examples, greater than 25 wt %, greater than 30 wt %, greater than 35 wt %, greater than 40 wt %, greater than 45 wt %, or greater than 50 wt % to about 55 wt %, about 60 wt %, about 65 wt %, or about 70 wt % of the ground corn product can have a particle size of greater than 105 µm, as measured according to AOAC 965.22-1966.

The amount of the ground corn product that can have a particle size of 150 µm or less can be about 41 wt % to about 79 wt %, about 57 wt % to about 90 wt %, about 57 wt % to about 78 wt %, or about 57 wt % to about 75 wt %, as measured according to AOAC 965.22-1966. In some examples, greater than 40 wt %, greater than 50 wt %, greater than 60 wt %, greater than 70 wt %, greater than 75 wt %, or greater than 80 wt % of the ground corn product can have a particle size of 150 µm or less, as measured according to AOAC 965.22-1966.

The amount of the ground corn product that can have a particle size of 180 µm or less can be about 52 wt % to about 97 wt %, about 58 wt % to about 90 wt %, about 56 wt % to about 81 wt %, or about 62 wt % to about 97 wt %, as measured according to AOAC 965.22-1966. In some examples, greater than 50 wt %, greater than 60 wt %, greater than 70 wt %, greater than 80 wt %, greater than 90 wt %, greater than 93 wt %, greater than 95 wt %, or greater than 97 wt % of the ground corn product can have a particle size of 180 μm or less, as measured according to AOAC 965.22-1966.

The amount of the ground corn product that can have a particle size of 250 μm or less can be about 71 wt % to about 98 wt %, about 81 wt % to about 98 wt %, about 91 wt % to about 98 wt %, or about 71 wt % to about 92 wt %, as measured according to AOAC 965.22-1966. In some examples, greater than 70 wt %, greater than 80 wt %, greater than 85 wt %, greater than 90 wt %, greater than 93 wt %, greater than 95 wt %, greater than 96 wt %, greater than 97 wt % or greater than 98 wt % of the ground corn product can have a particle size of 250 μm or less, as measured according to AOAC 965.22-1966.

The amount of the ground corn product that can have a particle size of 425 μm or less can be about 87 wt % to about 96 wt %, about 87 wt % to about 95 wt %, about 87 wt % to about 99.9 wt %, or about 96 wt % to about 99.9 wt %, as measured according to AOAC 965.22-1966. In some examples, greater than 85 wt %, greater than 86 wt %, greater than 87 wt %, greater than 88 wt %, greater than 89 wt %, greater than 90 wt %, greater than 91 wt %, greater than 92 wt %, greater than 93 wt %, greater than 94 wt %, greater than 95 wt %, greater than 96 wt %, greater than 97 wt %, greater than 98 wt %, greater than 99 wt %, greater than 99.5 wt %, greater than 99.7 wt %, or greater than 99.9 wt % of the ground corn product can have a particle size of 425 μm or less, as measured according to AOAC 965.22-1966. In other examples, greater than 80 wt %, greater than 83 wt %, greater than 85 wt %, greater than 87 wt %, greater than 90 wt %, greater than 93 wt %, or greater than 95 wt % of the ground corn product can have a particle size of 425 μm or less, as measured according to AOAC 965.22-1966. In some examples 100% of the ground corn product can have a particle size of 425 μm or less.

The amount of the ground corn product that can have a particle size of 850 μm or less can be about 98 wt % to about 99.95 wt %, about 99.2 wt % to about 99.9 wt %, about 99.2 wt % to about 99.95 wt %, or about 99.9 wt % to about 99.95 wt %, as measured according to AOAC 965.22-1966. In some examples, greater than 97 wt %, greater than 98 wt %, greater than 99 wt %, greater than 99.3 wt %, greater than 99.5 wt %, greater than 99.7 wt %, greater than 99.9 wt %, greater than 99.91 wt %, greater than 99.93 wt %, or greater than 99.95 wt % of the ground corn product can have a particle size of 850 μm or less, as measured according to AOAC 965.22-1966.

In some examples, about 30 wt % to about 65 wt % of the ground corn product can have a particle size of 105 μm or less; about 40 wt % to about 80 wt % of the ground corn product can have a particle size of 150 μm or less; about 50 wt % to about 97 wt % of the ground corn product can have a particle size of 180 μm or less; about 70 wt % to about 98 wt % of the ground corn product can have a particle size of 250 μm or less; about 85 wt % to about 99.9 wt % of the ground corn product can have a particle size of 425 μm or less; and about 98 wt % to about 99.95 wt % of the ground corn product can have a particle size of 850 μm or less, as measured according to AOAC 965.22-1966. In other examples, greater than 30 wt %, greater than 40 wt %, greater than 50 wt %, or greater than 60 wt % of the ground corn product can have a particle size of 105 μm or less; greater than 40 wt %, greater than 50 wt %, greater than 60 wt %, or greater than 70 wt % of the ground corn product can have a particle size of 150 μm or less; greater than 50 wt %, greater than 60 wt %, greater than 70 wt %, or greater than 80 wt % of the ground corn product can have a particle size of 180 μm or less; greater than 70 wt %, greater than 80 wt %, greater than 90 wt %, or greater than 95 wt % of the ground corn product for a particle size of 250 μm or less; greater than 85 wt %, greater than 90 wt %, greater than 95 wt %, greater than 97 wt %, greater than 99 wt %, greater than 99.5 wt %, or greater than 99.9 wt % of the ground corn product can have a particle size of 425 μm or less; greater than 98 wt %, greater than 99 wt %, greater than 99.5 wt %, greater than 99.9 wt %, greater than 99.93 wt %, or greater than 99.95 wt % of the ground corn product can have a particle size of 850 μm or less, as measured according to AOAC 965.22-1966. In at least one example, greater than 25 wt %, greater than 30 wt %, greater than 35 wt %, greater than 40 wt %, or greater than 45 wt % of the ground corn product can have a particle size of greater than 105 μm, and greater than 80 wt %, greater than 85 wt %, greater than 90 wt %, or greater than 95 wt % of the ground corn product can have a particle size of 425 μm or less, as measured according to AOAC 965.22-1966.

The particle size and the particle size distribution of the ground corn product by volume can be analyzed on a LS™ 13-320 laser diffraction particle size analyzer with a Tornado dry sample module attachment, both commercially available from Beckman Coulter Life Sciences. The laser diffraction particle analysis can be conducted according to the ISO 13320:2009, "Particle Size Analysis—Laser Diffraction Methods." available from International Organization for Standardization.

The amount of the ground corn product that can have a particle size of 25 μm or less can be about 2 vol % to about 10 vol %, about 2 vol % to about 9 vol %, about 2 vol % to about 8 vol %, or about 3 vol % to about 10 vol %, as measured according to ISO 13320:2009. In some examples, greater than 2 vol %, greater than 4 vol %, greater than 6 vol %, greater than 8 vol %, or greater than 9 vol % of the ground corn product can have a particle size of 25 μm or less, as measured according to ISO 13320:2009.

The amount of the ground corn product that can have a particle size of 60 μm or less can be about 16 vol % to about 24 vol %, about 19 vol % to about 25 vol %, about 16 vol % to about 26 vol %, or about 19 vol % to about 28 vol %, as measured according to ISO 13320:2009. In some examples, greater than 10 vol %, greater than 13 vol %, greater than 15 vol %, greater than 17 vol %, greater than 18 vol %, greater than 20 vol %, greater than 22 vol %, greater than 23 vol %, greater than 25 vol %, greater than 28 vol %, greater than 30 vol %, greater than 35 vol % of the ground corn product can have a particle size of 60 μm or less, as measured according to ISO 13320:2009.

The amount of the ground corn product that can have a particle size of 400 μm or less can be about 42 vol % to about 74 vol %, about 42 vol % to about 71 vol %, about 59 vol % to about 71 vol %, or about 54 vol % to about 71 vol % of the ground corn product can have a particle size of 400 μm or less, as measured according to ISO 13320:2009. In some examples, greater than 40 vol %, greater than 45 vol %, greater than 50 vol %, greater than 55 vol %, greater than 60 vol %, greater than 65 vol %, or greater than 70 vol % of the ground corn product can have a particle size of 400 μm or less, as measured according to ISO 13320:2009.

The amount of the ground corn product that can have a particle size of 800 μm or less can be about 86 vol % to about 90 vol %, about 86 vol % to about 96 vol %, about 87 vol % to about 95 vol %, or about 87 vol % to about 96 vol %, as measured according to ISO 13320:2009. In some examples, greater than 85 vol %, greater than 87 vol %, greater than 89 vol %, greater than 90 vol %, greater than 93 vol %, greater than 94 vol %, or greater than 95 vol % of the ground corn product can have a particle size of 800 μm or less, as measured according to ISO 13320:2009.

In one or more examples, about 10 vol % to about 30 vol % of the ground corn product can have a particle size of 60 μm or less; about 40 vol % to about 70 vol % of the ground corn product can have a particle size of 400 μm or less; and about 85 vol % to about 95 vol % of the ground corn product can have a particle size of 800 μm or less. In other examples, greater than 10 vol %, greater than 15 vol %, greater than 18 vol %, greater than 20 vol %, greater than 25 vol %, greater than 28 vol %, or greater than 30 vol % of the ground corn product can have a particle size of 60 μm or less; greater than 40 vol %, greater than 50 vol %, greater than 55 vol %, greater than 60 vol %, or greater than 70 vol % of the ground corn product can have a particle size of 400 μm or less; and greater than 85 vol %, greater than 90 vol %, or greater than 95 vol % of the ground corn product can have a particle size of 800 μm or less. For example, greater than 18 vol % of the ground corn product can have a particle size of 60 μm or less and greater than 50 vol % of the ground corn product can have a particle size of 400 μm or less, as measured according to ISO 13320:2009.

In some examples, greater than 20 vol % of the ground corn product can have a particle size of 60 μm or less and greater than 60 vol % of the ground corn product can have a particle size of 400 μm or less, as measured according to ISO 13320:2009. In other examples, greater than 18 vol % of the ground corn product can have a particle size of 60 μm or less and greater than 85 vol % of the ground corn product can have a particle size of 800 μm or less, as measured according to ISO 13320:2009. In some examples, greater than 50 vol % of the ground corn product can have a particle size of 400 μm or less and greater than 85 vol % of the ground corn product can have a particle size of 800 μm or less, as measured according to ISO 13320:2009. In other examples, greater than 22 vol % of the ground corn product can have a particle size of 60 μm or less, greater than 60 vol % of the ground corn product having a particle size of 400 μm or less, and greater than 90 vol % of the ground corn product can have a particle size of 800 μm or less, as measured according to ISO 13320:2009.

The volumetric particle size distribution of the ground corn product can be provided by particle size, $d_v$, where v is the volume percent of the ground corn product that has a particle size smaller than the specified value. For example, if the ground corn product has a din by volume percent of 18 μm, then 10 vol % of the ground corn product has a particle size of less than 18 μm and 90 vol % of the ground corn product has a particle size of 18 μm and larger. In another example, if the ground corn product has a $d_{50}$ by volume percent of 170 μm, then 50 vol % of the ground corn product has a particle size of less than 170 μm and 50 vol % of the ground corn product has a particle size of 170 μm and larger. In another example, if the ground corn product has a $d_{90}$ by volume percent of 800 μm, then 90 vol % of the ground corn product has a particle size of less than 800 μm and 10 vol % of the ground corn product has a particle size of 800 μm and larger.

The ground corn product can have a $d_{10}$ by volume percent of 5 μm, 10 μm, 12 μm, or 15 μm to 20 μm, 25 μm, 30 μm, 40 μm, or 50 μm, as measured according to ISO 13320:2009. For example, the ground corn product can have a $d_{10}$ by volume percent of 10 μm to 30 μm, 10 μm to 25 μm, 10 μm to 20 μm, 12 μm to 30 μm, 12 μm to 25 μm, 12 μm to 20 μm, 14 μm to 30 μm, 14 μm to 25 μm, 14 μm to 20 μm, 15 μm to 25 μm, 16 μm to 30 μm, or 16 μm to 25 μm, as measured according to ISO 13320:2009.

The ground corn product can have a $d_{25}$ by volume percent of 30 μm, 40 μm, or 50 μm to 55 μm, 60 μm, 70 μm, 80 μm, 90 μm, 100 μm, 110 μm, 120 μm, 130 μm, 140 μm, or 150 μm, as measured according to ISO 13320:2009. For example, the ground corn product can have a $d_{25}$ by volume percent of 30 μm to 120 μm, 30 μm to 110 μm, 30 μm to 101 μm, 30 μm to 93 μm, 30 μm to 88 μm, 30 μm to 75 μm, 30 μm to 66 μm, 30 μm to 55 μm, 40 μm to 120 μm, 40 μm to 101 μm, 40 μm to 93 μm, 40 μm to 88 μm, 40 μm to 75 μm, 40 μm to 66 μm, 40 μm to 55 μm, 40 μm to 48 μm, 50 μm to 120 μm, 50 μm to 110 μm, 50 μm to 101 μm, 50 μm to 97 μm, 50 μm to 93 μm, 50 μm to 75 μm, or 50 μm to 66 μm, as measured according to ISO 13320:2009.

The ground corn product can have a $d_{50}$ by volume percent of 100 μm, 110 μm, 125 μm, or 150 μm to 200 μm, 250 μm, 300 μm, 350 μm, 400 μm, 450 μm, or 500 μm, as measured according to ISO 13320:2009. For example, the ground corn product can have a ds by volume percent of 100 μm to 500 μm, 100 μm to 450 μm, 100 μm to 400 μm, 100 μm to 350 μm, 100 μm to 300 μm, 100 μm to 250 μm, 100 μm to 200 μm, 100 μm to 150 μm, 110 μm to 500 μm, 110 μm to 400 μm, 110 μm to 300 μm, 110 μm to 250 μm, 110 μm to 200 μm, 110 μm to 150 μm, 150 μm to 500 μm, 150 μm to 450 μm, 150 μm to 400 μm, 150 μm to 350 μm, 150 μm to 300 μm, 150 μm to 250 μm, 150 μm to 200 μm, or 150 μm to 175 μm, as measured according to ISO 13320:2009.

The ground corn product can have a d-s by volume percent of 350 μm, 375 μm, 400 μm, or 425 μm to 450 μm, 500 μm, 550 μm, 600 μm, 650 μm, or 700 μm, as measured according to ISO 13320:2009. For example, the ground corn product can have a $d_{75}$ by volume percent of 350 μm to 700 μm, 350 μm to 650 μm, 350 μm to 600 μm, 350 μm to 550 μm, 350 μm to 500 μm, 350 μm to 450 μm, 350 μm to 400 μm, 375 μm to 700 μm, 375 μm to 600 μm, 375 μm to 500 μm, 375 μm to 450 μm, 375 μm to 400 μm, 400 μm to 700 μm, 400 μm to 600 μm, 400 μm to 500 μm, 425 μm to 700 μm, 425 μm to 650 μm, 425 μm to 600 μm, 425 μm to 550 μm, or 425 μm to 500 μm, as measured according to ISO 13320:2009.

The ground corn product can have a $d_{90}$ by volume percent of 650 μm, 700 μm, 750 μm, or 800 μm to 850 μm, 900 μm, 950 μm, 1,000 μm, 1,050 μm, or 1,100 μm, as measured according to ISO 13320:2009. For example, the ground corn product can have a do by volume percent of 650 μm to 1,100 μm, 675 μm to 1,100 μm, 700 μm to 1,100 μm, 725 μm to 1,100 μm, 750 μm to 1,100 μm, 800 μm to 1,100 μm, 850 μm to 1,100 μm, 650 μm to 1,000 μm, 675 μm to 1,000 μm, 700 μm to 1,000 μm, 725 μm to 1,000 μm, 750 μm to 1,000 μm, 800 μm to 1,000 μm, 850 μm to 1,000 μm, 650 μm to 950 μm, 700 μm to 950 μm, 725 μm to 950 μm, 750 μm to 950 μm, 800 μm to 950 μm, 850 μm to 950 μm, 650 μm to 900 μm, 675 μm to 900 μm, 700 μm to 900 μm, 750 μm to 900 μm, 800 μm to 900 μm, 650 μm to 850 μm, 675 μm to 850 μm, 700 μm to 850 μm, or 750 μm to 850 μm, as measured according to ISO 13320:2009.

The ground corn product can include, but is not limited to, pericarp particles, floury endosperm particles, germ particles, starch particles, and fiber particles. The starch portions and the germ portions of the corn kernels can be size-reduced to smaller sizes than the fibrous portions of the corn kernels. It is believed that this difference in sizes of the corn portions is a result of the shearing action of the milling device (e.g., air swept pulverizer or disk mill fiberizer). The ground corn product, therefore, can include fiber particles with different particle size distributions than the total particles of the ground corn product.

In one or more examples, the fiber particles of the ground corn product can have a $d_{50}$ by volume percent of 125 μm, 150 μm, or 250 μm to 300 μm, 350 μm, 400 μm, or 500 μm and the total particles of the ground corn product can have a $d_{50}$ by volume percent of 100 μm, 125 μm, or 150 μm to 200 μm, 300 μm, 400 μm, or 500 μm, as measured according to ISO 13320:2009. For example, the fiber particles of the ground corn product can have a $d_{50}$ by volume percent of 125 μm to 450 μm, 150 μm to 450 μm, or 175 μm to 400 μm and the total particles of the ground corn product can have a $d_{50}$ by volume percent of 100 μm to 400 μm, 100 μm to 350 μm, or 125 μm to 300 μm, as measured according to ISO 13320:2009.

In one or more examples, a plurality of total particles of the ground corn product can include a plurality of fiber particles. The fiber particles in the ground corn product can have a $d_{50}$ by volume percent of greater than 160 μm, greater than 180 μm, greater than 200 μm, greater than 250 μm, greater than 300 μm, or greater than 350 μm to 500 μm and the total particles of the ground corn product can have a $d_{50}$ by volume percent of 100 μm to less than 300 μm, less than 350 μm, less than 450 μm, or less than 500 μm, as measured according to ISO 13320:2009. For example, the fiber particles of the ground corn product can have a $d_{50}$ by volume percent of greater than 200 μm and the total particles of the ground corn product can have a $d_{50}$ by volume percent of less than 500 μm, as measured according to ISO 13320: 2009. In another example, the fiber particles of the ground corn product can have a $d_{50}$ by volume percent of greater than 250 μm and the total particles of the ground corn product can have a $d_{50}$ by volume percent of less than 450 μm, as measured according to ISO 13320:2009. In some examples, the fiber particles of the ground corn product can have a $d_{50}$ by volume percent of greater than 300 μm and the total particles of the ground corn product can have a $d_{50}$ by volume percent of less than 400 μm, as measured according to ISO 13320:2009. In other examples, the fiber particles of the ground corn product can have a ds by volume percent of greater than 350 μm and the total particles of the ground corn product can have a $d_{50}$ by volume percent of less than 350 μm, as measured according to ISO 13320:200). In other examples, the fiber particles of the ground corn product can have a $d_{50}$ by volume percent of greater than 200 μm to 500 μm and the total particles of the ground corn product can have a $d_{50}$ by volume percent of 100 μm to less than 500 μm, as measured according to ISO 13320:2009.

In other examples, the fiber particles of the ground corn product can have a $d_{50}$ by volume percent of 375 μm, 400 μm, or 450 μm to 500 μm, 600 μm, or 700 μm and the total particles of the ground corn product can have a $d_{75}$ by volume percent of 350 μm, 400 μm, or 425 μm to 450 μm, 500 μm, 600 μm, or 700 μm, as measured according to ISO 13320:2009. For example, the fiber particles of the ground corn product can have a $d_{75}$ by volume percent of 375 μm to 700 μm, 400 μm to 600 μm, or 450 μm to 700 μm and the total particles of the ground corn product can have a d-s by volume percent of 350 μm to 600 μm, 350 μm to 500 μm, or 325 μm to 550 μm, as measured according to ISO 13320: 2009.

It should be understood that the ground corn product or any portion thereof (e.g., fiber particles) can have a combination of any two or more properties discussed and described above or elsewhere herein. For example, the ground corn product can have a combination of any two, any three, any four, or more, of the following properties: the particle size by weight, the particle size by volume, the particle size distribution by weight, the particle size distribution by volume, the $d_{10}$ value, the $d_{25}$ value, the $d_{50}$ value, the $d_{75}$ value, the $d_{90}$ value, and the crystallinity, which are discussed and described above or elsewhere herein.

The ground corn product and the corn pieces (e.g., corn kernels) from which the ground corn product is ground can have the same composition or substantially the same composition. The corn pieces and the ground corn product can contain, but are not limited to, water, one or more starches (e.g., saccharides and oligosaccharides), one or more proteins, cellulose, one or more oils and/or greases (e.g., saturated and unsaturated fatty acids), one or more volatile organic compounds, other components, or any combination thereof. Generally, for example, the corn pieces and the ground corn product can each include about 5 wt % to about 40 wt % of water, about 15 wt % to about 25 wt % of oligosaccharides, and about 0.5 wt % to about 5 wt % of corn oil.

The corn oil can be or include one or more oils and/or one or more greases which can include one or more saturated fatty acids and/or one or more unsaturated fatty acids. Illustrative saturated fatty acids and unsaturated fatty acids that can be contained in the corn pieces and the ground corn product can be or include caprylic acid, capric acid, myristic acid, palmitic acid, stearic acid, arachidic acid, oleic acid, linoleic acid, linolenic acid, isomers thereof, or any mixture thereof. For example, the corn oil can include about 10 wt % to about 15 wt % of palmitic acid, about 1 wt % to about 2 wt % of stearic acid, about 0.5 wt % to about 2 wt % of arachidic acid, about 20 wt % to about 40 wt % of oleic acid, about 45 wt % to about 65 wt % of linoleic acid, and about 0.5 wt % to about 2 wt % of linolenic acid.

The corn pieces and the ground corn product can include about 0.5 wt %, about 0.8 wt %, about 1 wt %, about 1.5 wt %, or about 1.8 wt % to about 2 wt %, about 2.2 wt %, about 2.5 wt %, about 2.7 wt %, about 3 wt %, about 3.2 wt %, about 3.5 wt %, about 3.7 wt %, about 4 wt %, about 4.5 wt %, or more of corn oil, based on a solids weight of the corn pieces or the ground corn product. For example, the corn pieces and the ground corn product can include about 0.5 wt % to about 4.5 wt %, about 0.5 wt % to about 4 wt %, about 0.5 wt % to about 3.5 wt %, about 0.5 wt % to about 3 wt %, about 0.5 wt % to about 2.5 wt %, about 0.5 wt %, to about 2 wt %, about 0.5 wt % to about 1.5 wt %, about 0.5 wt % to about 1 wt %, about 1 wt % to about 4.5 wt %, about 1 wt % to about 4 wt %, about 1 wt % to about 3.5 wt %, about 1 wt % to about 3 wt %, about 1 wt % to about 2.5 wt %, about 1 wt % to about 2 wt %, about 1 wt % to about 1.5 wt %, about 1 wt % to about 1.3 wt %, about 2 wt % to about 4.5 wt %, about 2 wt % to about 4 wt %, about 2 wt % to about 3.5 wt %, about 2 wt % to about 3 wt %, about 2 wt % to about 2.5 wt %, about 2 wt % to about 2.3 wt %, about 2.5 wt % to about 4.5 wt %, about 2.5 wt % to about 4 wt %, about 2.5 wt % to about 3.5 wt %, about 2.5 wt % to about 3 wt %, about 2.5 wt % to about 2.8 wt %, about 3 wt % to about 4.5 wt %, about 3 wt % to about 4 wt %, about 3 wt % to about 3.7 wt %, about 3 wt % to about 3.5 wt %, or about 3 wt % to about 3.2 wt % of corn oil, based on a solids weight of the corn pieces or the ground corn product.

In one or more examples, the corn pieces and the ground corn product can include about 5 wt % to about 40 wt % of water, about 15 wt % to about 25 wt % of soluble starches, about 5 wt % to about 15 wt % of cellulose, and about 0.5 wt % to about 4 wt % of corn oil, based on a solids weight of the corn pieces or the ground corn product. In some examples, the corn pieces and the ground corn product can include about 10 wt % to about 35 wt % of water, about 17 wt % to about 28 wt % of soluble starches, about 10 wt % to about 15 wt % of cellulose, and about 2 wt % to about 4 wt % of corn oil, based on a solids weight of the corn pieces or the ground corn product.

Corn pieces (e.g., corn kernels) can be milled, ground, pulverized, fiberized, or otherwise size-reduced to produce the ground corn product. The corn pieces can also be milled, ground, pulverized, fiberized, or otherwise size-reduced two, three, or more times to produce the ground corn product. The plurality of corn pieces, therefore, can be or include size-reduced corn that is further size-reduced to produce the ground corn product. Illustrative corn pieces that are suitable to be size-reduced can be or include, but are not limited to, whole corn kernels, milled corn kernels, pulverized corn kernels, fiberized corn kernels, ground corn kernels, fragmented corn kernels, crushed corn kernels, smashed corn kernels, shredded corn kernels, other size-reduced corn kernels, fresh corn kernels, dried corn kernels, or any mixture thereof.

In some examples, the corn pieces (e.g., corn kernels) can be size-reduced one or more times with a hammer mill, a roller mill, or other type of mill to produce the plurality of corn pieces that can be further size-reduced one or more times with a high shear mill to produce the ground corn product. For example, the corn pieces can be passed through one or more hammer mills to produce size-reduced corn that subsequently can be passed through a disk mill fiberizer, an air swept pulverizer, and/or any other high shear mills to produce the ground corn product. The ground corn product can be or include fiberized corn, pulverized corn, disk milled corn, other high shear milled corn, or any mixtures thereof.

The corn pieces can be introduced to a high shear mill that can have two rotating surfaces, such as a first rotatable disk and a second rotatable disk. In other examples, the corn pieces can be introduced to a high shear mill that can have one rotating surface and one stationary surface, such as one rotatable disk and one stationary disk, plate, or other surface. The corn pieces can make contact to the two rotating surfaces or can make contact to the one rotating surface and the one stationary surface to mill, shear, grind, fiberize, pulverize, or otherwise size-reduce the corn pieces between the two rotating surfaces or between the one rotating surface and the one stationary surface to produce the ground corn product. For example, the high shear mill can be a disk attrition mill and the corn pieces can be milled or otherwise side-reduced between: a rotatable disk and a stationary disk; a rotatable disk and a stationary surface; or two rotatable disks to produce the ground corn product. In some examples, the corn pieces can be fiberized between two sets of triangular teeth, relatively sharp teeth, or fiberizing teeth of the disk attrition mill to produce fiberized corn product. In other examples, the corn pieces can be pulverized between two sets of rectangular teeth, relatively dull teeth, or pulverizing teeth of the disk attrition mill to produce pulverized corn product. In some examples, at least one disk can have grinding teeth for fiberizing the corn pieces into the ground corn product. Various disk attrition mills can be used to fiberize and/or pulverize. Some disk attrition mills can have a fiberizing side and a pulverizing side which are independent from each other. Disk attrition mills that can be used to mill, grind, or otherwise size-reduce corn can include, for example, the 167.64 cm (66 inch) fiberizer, commercially available from Reynolds Engineering and Equipment. Inc.

In one or more examples, the corn pieces can be introduced into a disk attrition mill, such as a high shear fiberizer or a high shear pulverizer. The disk attrition mill can include a first rotatable disk and either a second rotatable disk or a stationary surface. The disk attrition mill can have at least one set of grinding teeth disposed on each of the first rotatable disk, the second rotatable disk, and the stationary surface. In some configurations, any of the first rotatable disk, the second rotatable disk, or the stationary surface can be free of grinding teeth. In some examples of the disk attrition mill, the first rotatable disk can have a first set of grinding teeth and either the second rotatable disk or the stationary surface is free of grinding teeth. In other examples of the disk attrition mill, the first rotatable disk can have a first set of grinding teeth and either the second rotatable disk or the stationary surface can have a second set of grinding teeth.

The first rotatable disk and either the second rotatable disk or the stationary surface can be separated by a predetermined distance from each other to provide a shearing gap therebetween. The predetermined distance can be fixed or adjustable. If the first rotatable disk and/or either the second rotatable disk or the stationary surface have one or more sets of grinding teeth, then the shearing gap can be measured by the distance between two sets of grinding teeth or between one set of grinding teeth and either the rotatable disk or the stationary surface. For example, the shearing gap can be measured by the distance between the first set of grinding teeth on the first rotatable disk and the second set of grinding teeth on either the second rotatable disk or the stationary surface. In another example, the shearing gap can be measured by the distance between the first set of grinding teeth on the first rotatable disk and either the second rotatable disk or the stationary surface absent of grinding teeth. The shearing gap can be adjusted and/or can be maintained before and/or during the milling of the corn pieces to produce the ground corn product. The shearing gap can be adjusted to produce the ground corn product having the particle size of the ground corn product and a desired distribution of the particle size of the ground corn product. Once the ground corn product is produced within the shearing gap, the ground corn product can pass through the shearing gap to exit the disk mill.

The shearing gap or the distance between the first rotatable disk and/or either the second rotatable disk or the stationary surface can be less than 3,000 µm, less than 2,600 µm, less than 2,000 µm, less than 1,500 µm, less than 1,000 µm, less than 800 µm, less than 500 µm, or less than 250 µm. The shearing gap or the distance between the first rotatable disk and/or either the second rotatable disk or the stationary surface can be about 50 µm, about 100 µm, about 150 µm, or about 250 µm to about 300 µm, about 500 µm, about 700 µm, about 800 µm, about 1,000 µm, about 1,500 µm, about 2,000 µm, about 2,500 µm, or about 2.750 µm. For example, the shearing gap or the distance between the first rotatable disk and/or either the second rotatable disk or the stationary surface can be about 250 µm to about 3,000 µm, about 400 µm to about 2,000 µm, about 500 µm to about 1,000 µm, about 700 µm to about 800 µm, about 700 µm to about 2,800 µm, or about 600 µm to about 2,600 µm.

The corn pieces can be ground, milled, fiberized, pulverized, or otherwise size-reduced to produce the ground corn product that maintains at least a substantial amount of the crystallinity relative to the corn pieces ground to produce the ground corn product. The ground corn product can have a crystallinity that is greater than 75%, about 80%, about 85%, or about 90% to about 92%, about 94%, about 95%, about 96%, about 97%, about 98%, about 99%, about 99.2%, about 99.5%, about 99.7%, about 99.8%, about 99.9%, about 99.95%, about 99.97%, about 99.98%, about 99.99%, or 100%, as compared to the crystallinity of the corn pieces ground to produce the ground corn product. For example, the ground corn product can have a crystallinity that is greater than 75%, greater than 80%, greater than 85%, greater than 90%, greater than 92%, greater than 94%, greater than 95%, greater than 96%, greater than 97%, greater than 98%, greater than 99%, greater than 99.2%, greater than 99.5%, greater than 99.7%, greater than 99.8%, greater than 99.9%, greater than 99.95%, greater than 99.97%, greater than 99.98%, greater than 99.99%, or 100%, as compared to the crystallinity of the corn pieces ground to produce the ground corn product.

For example, the ground corn product can have a crystallinity that is about 80% to 100%, about 85% to 100%, about 90% to 100%, about 95% to 100%, about 97% to 100%, about 98% to 100%, about 99% to 100%, about 99.5% to 100%, about 99.9% to 100%, about 99.95% to 100%, about 75% to about 99%, about 80% to about 99%, about 85% to about 99%, about 90% to about 99%, about 95% to about 99%, about 97% to about 99%, about 98% to about 99%, or about 98.5% to about 99%, as compared to the crystallinity of the corn pieces ground to produce the ground corn product. In other examples, the ground corn product can have a crystallinity that is greater than 75% to 100%, greater than 80% to 100%, greater than 85% to 100%, greater than 90%36 to 100%, greater than 95% to 100%, greater than 97% to 100%, greater than 98% to 100%, greater than 99% to 100%, greater than 99.5% to 100%, greater than 99.9% to 100%, greater than 99.95% to 100%, greater than 75% to about 99%, greater than 80% to about 99%, greater than 85% to about 99%, greater than 90% to about 99%, greater than 95% to about 99%, greater than 97% to about 99%, greater than 98% to about 99%, or greater than 98.5% to about 99%, as compared to the crystallinity of the corn pieces ground to produce the ground corn product.

The ground corn product can have a crystallinity that is reduced by less than 25%, less than 23%, less than 20%, less than 17%, less than 15%, less than 12%, less than 10%, less than 8%, less than 6%, less than 5%, less than 4%, less than 3%, less than 2%, less than 1%, less than 0.8%, less than 0.5%, less than 0.3%, less than 0.2%, less than 0.1%, less than 0.05%, less than 0.03%, or less than 0.01%, as compared to the crystallinity of the corn pieces ground to produce the ground corn product. For example, the ground corn product can have a crystallinity that is reduced by less than 25% to about 0.001%, less than 25% to about 0.01%, less than 25% to about 0.05%, less than 25% to about 0.1%, less than 10% to about 0.001%, less than 10% to about 0.01%, less than 10% to about 0.05%, less than 10% to about 0.1%, less than 5% to about 0.001%, less than 5% to about 0.01%, less than 5% to about 0.05%, less than 5% to about 0.1%, less than 1% to about 0.001%, less than 1% to about 0.01%, less than 1% to about 0.05%, less than 1% to about 0.1%, less than 0.1% to about 0.001%, less than 0.1% to about 0.01%, less than 0.1% to about 0.08%, or less than 0.1% to about 0.04%, as compared to the crystallinity of the corn pieces ground to produce the ground corn product.

As used herein, the term "crystallinity" refers to a volume ratio of the crystalline portion of cellulose to the total volume of cellulose that includes both the amorphous portion and the crystalline portion. The degree of crystallinity of the ground corn product can be calculated from X-ray diffraction (XRD) data by using a crystalline area integration method based on Cheetham and Leping (Carbohydrate Polymers 36:277-284 (1998)); Nara el al. (Starch 35.12:407-410 (1983)); and Benedetti el al. (Journal of Material Science 18.4:1039-1048 (1983)). The intensities are first normalized over a limited range of data (e.g., 10° to 30° 2-theta). The normalization is determined by a baseline connecting the upper and lower bounds of 10° and 30° 2-theta and then dividing the intensities by the integrated area below the intensities curve and above the baseline. After normalization, a Savitzky-Gola, filter is used to smooth the data. The crystalline and amorphous regions can be separated by a function that connects peak baselines. The crystalline portion is the upper region and the amorphous portion is the lower region. The crystalline portion area and the total diffraction area are integrated. The degree of crystallinity is defined as the ratio of the crystalline area over the total diffraction area.

In one or more examples, at least a portion of the corn oil can be extracted or otherwise removed from the ground corn product, the slurry tank mixture containing the ground corn product, the liquefaction mash derived from the ground corn product, the fermentation mash, and/or the stillage. In some examples, the portion of the corn oil that is extracted from the ground corn product is the oil liberated from the corn cellular matrix within the ground corn product and any other oil that is bound by the corn cellular matrix remains in the ground corn product. The corn oil extraction and the corn oil testing can be performed on the SPE-DEX® 3000XL Automated Extractor System and the SPEED-VAP™ Solvent Evaporation System, both commercially available from the Horizon Technology Company, using EPA Method 1664A. The corn oil removed from the ground corn product can be greater than 0.6 wt %, greater than 0.7 wt %, or greater than 0.75 wt % to about 0.9 wt %, about 1 wt %, about 1.2 wt %, or greater of the total weight of the ground corn product. For example, the corn oil removed from the ground corn product can be greater than 0.6 wt % to about 1.2 wt %, greater than 0.65 wt % to about 1.1 wt %, or greater than 0.7 wt % to about 1.05 wt % of the total weight of the ground corn product. In another example, the corn oil removed from the ground corn product, e.g., the stillage, can be greater than 0.6 wt %, greater than 0.7 wt %, greater than 0.75 wt %, greater than 0.8 wt %, or greater than 0.85 wt % to about 0.9 wt %, about 1 wt %, about 1.2 wt %, about 1.3 wt %, about 1.4 wt %, about 1.5 wt %, about 1.6 wt %, about 1.7 wt %, about 1.8 wt %, about 1.9 wt %, about 2 wt %, about 2.3 wt %, about 2.5 wt %, about 2.7 wt %, about 3 wt %, about 3.3 wt %, about 3.5 wt %, about 3.7 wt %, about 4 wt %, or greater of the total weight of the ground corn product.

EXAMPLES

In order to provide a better understanding of the foregoing discussion, the following non-limiting examples are offered. Although the examples can be directed to specific embodiments, they are not to be viewed as limiting the invention in any specific respect.

Corn Sample Grind Description

For Examples 1-4, the following mill or mills were used as specified in each example. The hammer mill was a Model MG mill, manufactured by Kelly Duplex Mill and Manufacturing Company in Springfield. Ohio. The pulverizer was a Model 16-H air swept pulverizer manufactured by Schutz-O'Neill Company in Minneapolis, Minn. The disk mill fiberizer was a Model TOQ-18 fiberizer, manufactured by Reynolds Engineering & Equipment. Inc. in Muscatine, Iowa.

Ex. 1 was corn that was passed through the hammer mill and through the air swept pulverizer. Raw whole corn kernels were milled to produce hammermilled corn pieces. The hammer mill was operated at about 90 Hz with a tip speed of about 124 meters per second (about 24,500 fpm) using a number 8 screen (3.175 mm) or (⅛", or 0.125") at a feed rate of about 925 kg/hr (about 2.040 lbs/hr). The hammermilled corn pieces were pulverized in the air swept pulverizer to produce the ground corn product. The air swept pulverizer was operated at about 80 Hz with a tip speed of about 157 meters per second (about 30.840 fpm) using three 43.18 cm (about 17-inch) diameter CCD beater plates and a CLP liner at a feed rate of about 599 kg/hr (about 1,320 lbs/hr).

Ex. 2 was the same as Ex. 1, but the speed of the air swept pulverizer was reduced as compared to the air swept pulverizer in Ex. 1. Raw whole corn kernels were milled to produce hammermilled corn pieces. The hammer mill was operated at about 90 Hz with a tip speed of about 124 meters per second (about 24,500 fpm) using a number 8 screen (3.175 mm) or (⅛", or 0.125") at a feed rate of about 925 kg/hr (about 2,040 lbs/hr). The hammermilled corn pieces were pulverized in the air swept pulverizer to produce the ground corn product. The air swept pulverizer was operated at about 50 Hz with a tip speed of about 97.9 meters per second (about 19,270 fpm) using three 43.18 cm (about 17-inch) diameter CCD beater plates and a CLP liner at a feed rate of about 599 kg/hr (about 1,320 lbs/hr).

Ex. 3 was whole corn that was only run through a disk mill fiberizer. Raw whole corn kernels were milled in the disk mill fiberizer to produce the ground corn product. The disk mill fiberizer used a 45.72 cm (18-inch) diameter TQ18-016 fine tooth plates set with a gap of about 762 μm (about 0.030 inches) and was operated at about 60 Hz with a tip speed of about 124 meters per second (about 24,500 fpm) at a feed rate of about 413 kg/hr (about 910 lbs/hr).

Ex. 4 was corn that was passed through a hammer mill and a disk mill fiberizer. Raw whole corn kernels were milled to produce hammermilled corn pieces. The hammer mill was operated at about 90 Hz with a tip speed of about 124 meters per second (about 24,500 fpm) using a number 8 screen (3.175 mm) or (⅛", or 0.125") at a feed rate of about 925 kg/hr (about 2.040 lbs/hr). The hammermilled corn pieces were milled in the disk mill fiberizer to produce the ground corn product. The disk mill fiberizer used 45.72 cm (about 18-inch) diameter TQ18-016 fine tooth plates set with a gap of about 2.54 mm (about 0.100 inches) and was operated at about 60 Hz with a tip speed of about 124 meters per second (about 24,500 fpm) at a feed rate of about 1.890 kg/hr (about 4.170 lbs/hr).

CEx. 1 was corn that was passed through a hammer mill. CEx. 2 was corn that was run through a quad pair set up (a stack of 4 pairs of rolls) roller mill. The corn used in Exs. 1-4 were sourced locally in Muscatine, Iowa; the corn used in CEx. 1 was sourced from a Flint Hills Resources Fairbank facility; and the corn used in CEx. 2 was sourced from RMS in Tea, S. Dak.

Particle Size and Distribution

Table 1 shows the particle size by weight of the ground corn products as measured with sieves for Exs. 1-4 and CExs. 1-2. The sieves analysis was conducted according to the AOAC Official Method 965.22 "Sorting Corn Grits—Sieving Method," available from the AOAC International. The weight percent of the sample that was left on the specified sieve size had a particle size larger than the respective sieve size. For example, in Table 1, the sample particles in Ex. 3 had the following weight percent (wt %) particles for the respective particle sizes: 0.10 wt % larger than 850 μm, 3.60 wt % larger than 425 μm to 850 μm, 4.80 wt % larger than 250 μm to 425 μm, 1.50 wt % larger than 180 μm to 250 μm, 14.90 wt % larger than 150 μm to 180 μm, 9.75 wt % larger than 105 μm to 150 μm, and 65.35 wt % 105 μm or less in the pan.

TABLE 1

Particle Size by Weight (measured with sieves)

| Sieve Size (μm) | Particle Size (μm) | Weight Percent Left on Sieve (wt %) | | | | | |
|---|---|---|---|---|---|---|---|
| | | Ex. 1 | Ex. 2 | Ex. 3 | Ex. 4 | CEx. 1 | CEx. 2 |
| 850 | >850 | 0.05 | 0.05 | 0.10 | 0.60 | 15.00 | 3.01 |
| 425 | >425 to 850 | 0.05 | 5.20 | 3.60 | 12.40 | 25.05 | 27.28 |
| 250 | >250 to 425 | 2.10 | 14.05 | 4.80 | 15.40 | 11.90 | 38.45 |
| 180 | >180 to 250 | 1.20 | 24.55 | 1.50 | 9.10 | 6.30 | 10.40 |
| 150 | >150 to 180 | 21.90 | 15.55 | 14.90 | 4.80 | 3.90 | 9.13 |
| 105 | >105 to 150 | 15.00 | 8.85 | 9.75 | 16.25 | 7.90 | 6.72 |
| pan | 105 and smaller | 59.70 | 31.75 | 65.35 | 41.25 | 29.95 | 5.02 |

Table 2 shows the particle size by volume of the ground corn products and Table 3 shows the particle size distribution by volume of the ground corn products that were analyzed on a LS™ 13-320 laser diffraction particle size analyzer with a Tornado dry sample module attachment, both commercially available from Beckman Coulter Life Sciences. The laser diffraction particle analysis was conducted according to the ISO 13320:2009 "Particle Size Analysis—Laser Diffraction Methods".

The particle size by volume of the ground corn products shown in Table 2 is smaller than the particle size listed. For example: 10 vol % of the particles in the Ex. 3 sample had a particle size smaller than 17.68 μm.

TABLE 2

Particle Size by Volume (measured by laser diffraction)

| | Particle Size (μm) | | | | | |
|---|---|---|---|---|---|---|
| vol % | Ex. 1 | Ex. 2 | Ex. 3 | Ex. 4 | CEx. 1 | CEx. 2 |
| 10 | 18.34 | 24.92 | 17.68 | 21.10 | 88.71 | 135.20 |
| 25 | 54.89 | 101.10 | 47.44 | 92.33 | 282.90 | 304.80 |
| 50 | 168.70 | 287.30 | 167.10 | 285.00 | 686.50 | 531.60 |
| 75 | 404.20 | 630.30 | 486.70 | 587.40 | 1111.00 | 797.10 |
| 90 | 793.30 | 1097.00 | 967.70 | 876.20 | 1450.00 | 1125.00 |

Table 3 gives the complete distribution of particles within each of the listed size ranges. For example: 28.3 vol % of the particles in the Ex. 3 sample had a particle size of greater than 4 μm (e.g., about 4.01 μm) to about 60 μm.

TABLE 3

Volume % by Particle Size

| Particle Size (μm) | Particle Size Distribution (vol %) | | | | | |
|---|---|---|---|---|---|---|
| | Ex. 1 | Ex. 2 | Ex. 3 | Ex. 4 | CEx. 1 | CEx. 2 |
| 0-4 | 0 | 0 | 0 | 0 | 0 | 0 |
| >4-60 | 26.3 | 25.1 | 98.3 | 19.6 | 7.8 | 4.9 |
| >60-400 | 48.5 | 49.5 | 42.5 | 40.2 | 23.9 | 29.8 |
| >400-800 | 15.4 | 20.8 | 15.4 | 27.2 | 25.6 | 40.5 |
| >800-2,000 | 9.9 | 4.6 | 13.9 | 13.0 | 42.7 | 24.8 |

Oil and Grease Analysis

Each liquefaction sample was first centrifuged to separate the slurry into separate phases. Each phase was subjected to oil and grease analysis. Oil and grease testing was performed on the SPE-DEX® 3000XL Automated Extractor System and the SPEED-VAP™ Solvent Evaporation System, both commercially available from the Horizon Technology Company. The Horizon Technology automated extraction method. EPA Method 1664A, has been modified and validated to only remove liberated oil from the sample, leaving any oil that may be bound by the corn cellular matrix. The total average weight percent values are listed as the average of two analysis, summarized in Table 4.

TABLE 4

Percent recoveries of each slurry sample level after separation by centrifuge and their averages

| Sample | Total average oil/grease (wt %) |
|---|---|
| Ex. 1 | 0.97 |
| Ex. 2 | 1.01 |
| Ex. 3 | 1.03 |
| Ex. 4 | 0.70 |
| CEx. 1 | 0.26 |
| CEx. 2 | 0.55 |

As shown in Table 4, the average amount of oil/grease recovered in Examples 1-4 was significantly greater than the amount of oil/grease recovered in the Comparative Examples 1 and 2.

Microscopy Analysis

On each selected dry ground sample, microscopy was performed using polarized light and iodine staining on both a Wild Heerbrugg Observation microscope (10×) and an AmScope trinocular microscope (50×-500×). Observation for starch and fiber were noted.

Analytical Methodology

Liquefaction

About 70 g of each ground corn sample was combined with about 200 mL of water having a temperature of about 80° C., to provide a slurry of about 35 wt % of ground corn. About 1 mL of alpha amylase was added to the slurry. Enough 1.2 M HCl was added to each slurry to adjust the pH of the slurry to about 4. Each slurry sample was then placed in a shaker water bath at about 85° C. for about 60 min. After removing slurry sample from the shaker bath, about 0.3 nL of 12 M HCl was added to lower the slurry pH and arrest the amylase activity. The time needed to complete each process of liquefaction for each sample slurry was kept constant to limit sample to sample variability.

Oil and Grease Analysis

About 2 g of each ground corn sample and about 100 mL of diluted distilled water were combined in a vial. Drops of HCl was added to the diluted sample in the vial until the pH of sample was adjusted to less than 2. Oil and grease extraction and testing was performed on the SPE-DEX® 3000XL Automated Extractor System and the SPEED-VAP™ Solvent Evaporation System, both commercially available from the Horizon Technology Company. The sample was processed by the extractor and evaporation systems using hexane as the extraction solvent. The results for the oil and grease analysis are reported in Table 4.

Microscopy Analysis

For Comparative Examples 1-2 and Examples 1-4, microscopy was performed using polarized light and iodine staining on both a Wild Heerbrugg observation microscope having a magnification of 10× (FIGS. 1, 3, 5, 7, 9, and 11) and an AmScope trinocular microscope that had a magnification of 50×-500× (FIGS. 2, 4, 6, 8, 10, and 12).

Iodine Staining Procedure

About 1 g of each ground corn sample was combined with 14 mL distilled water in a 250 mL beaker. About 1 mL of pH 5 buffer was added to the solution. About 84 mL of distilled water was combined with about 1.2 nL of a 0.5 N iodine solution and added to the sample slurry. One or two drops of the sample was transferred to a slide and blended with about 1-2 drops of an aqueous glycerin solution (about 50 wt % of glycerin and about 50 wt % of water). A cover slip was placed on the sample and the sample was observed under the microscope at the referenced magnifications. In the iodine stained sample under polarized light, a distinct Maltese cross formed in each of the starch particles. Particles of fiber and other material appeared brown or showed no color on a lightly blue hued background.

In the CEx. 1 sample of hammer milled corn, pericarp and floury endosperm particles were viewed at 10× magnification (FIG. 1) and starch and fiber particles were viewed at 200× magnification (FIG. 3).

Figure 5:
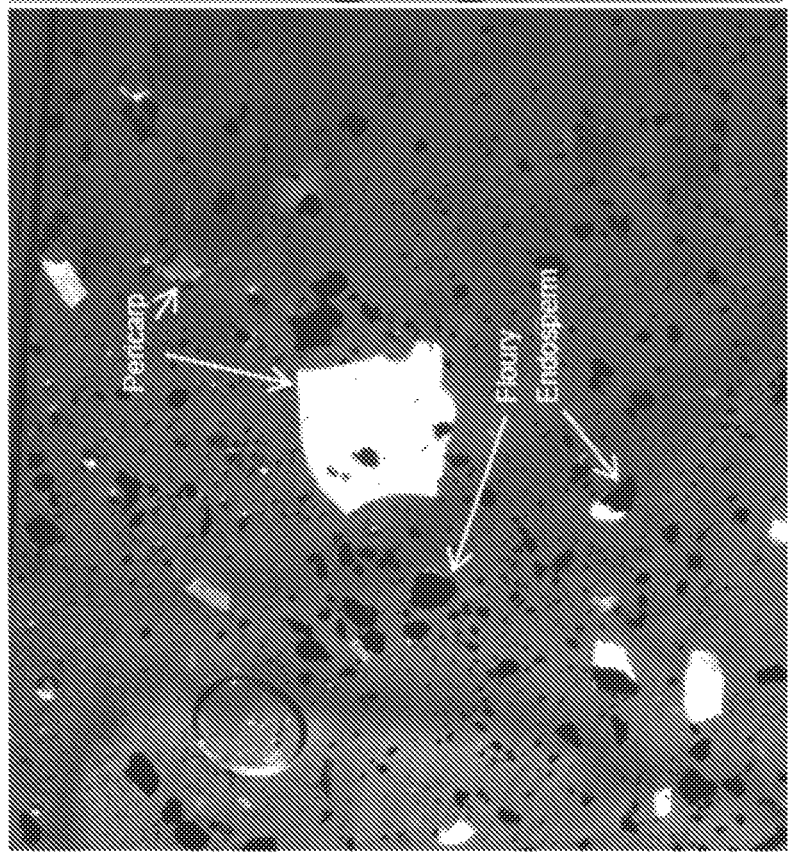
FIG. 5 is an optical microscope image of hammer milled corn (Comparative Example 1) at a magnification of 200×.

In the CEx. 2 sample of roller milled corn, pericarp and floury endosperm particles were viewed at 10× magnification (FIG. 4) and starch and fiber particles were viewed at 200× magnification (FIG. 5).

Figure 7:
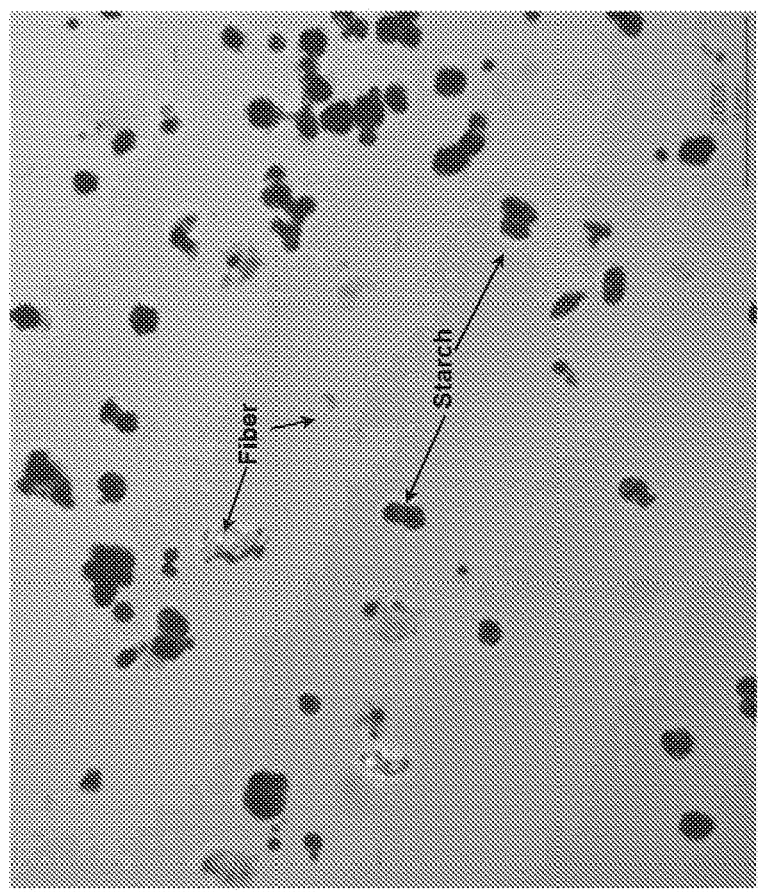
FIG. 7 is an optical microscope image of roller milled corn (Comparative Example 2) at a magnification of 200×.
Figure 6:
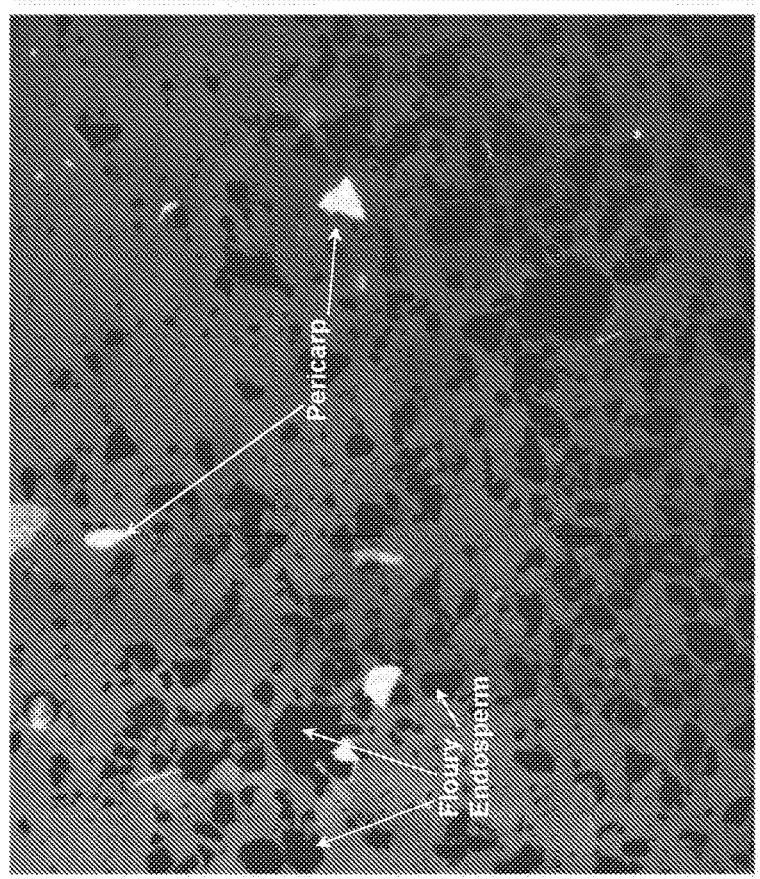
FIG. 6 is an optical microscope image of roller milled corn (Comparative Example 2) at a magnification of 10×.

In the Ex. 1 sample of disk pulverized corn, pericarp and floury endosperm particles were viewed at 10× magnification (FIG. 6) and starch and fiber particles were viewed at 200× magnification (FIG. 7).

Figure 9:
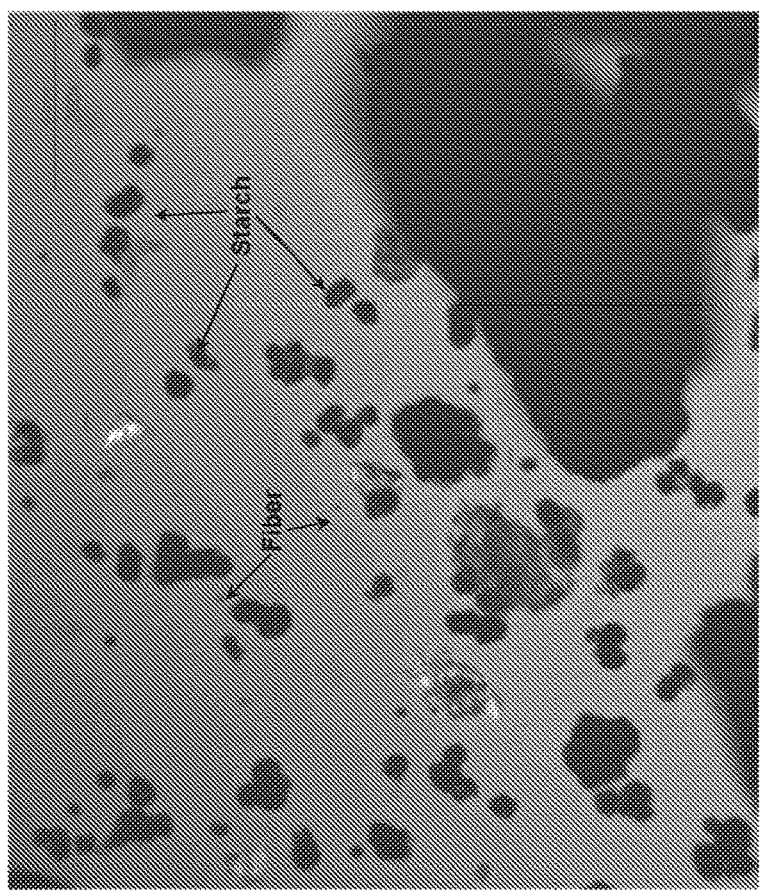
FIG. 9 is an optical microscope image of disk pulverized corn (Example 1) at a magnification of 200×.
Figure 8:
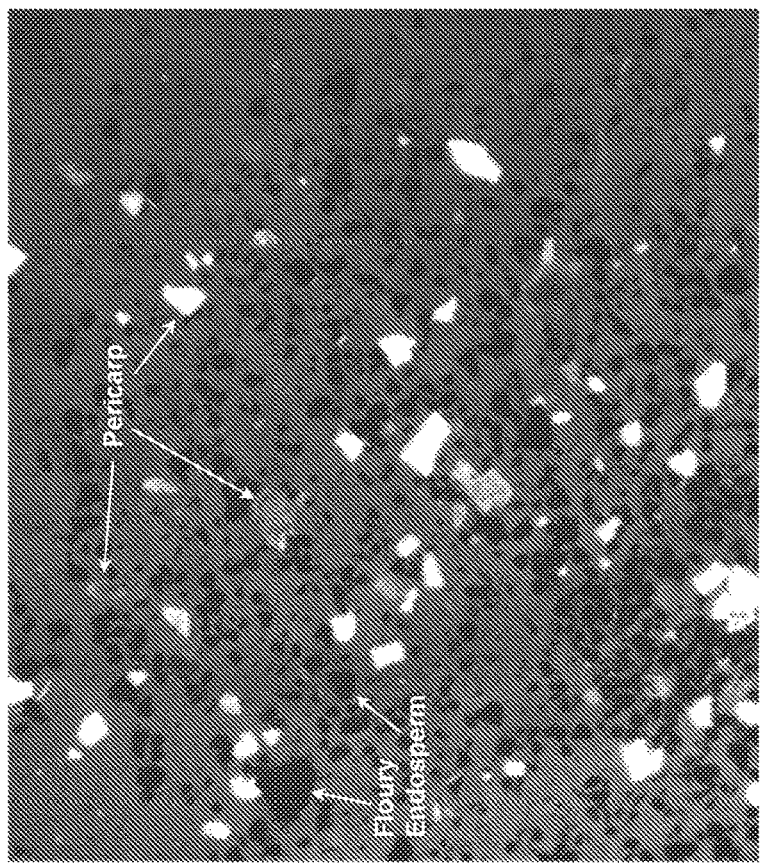
FIG. 8 is an optical microscope image of disk pulverized corn (Example 1) at a magnification of 10×.

In the Ex. 2 sample of disk pulverized corn, pericarp and floury endosperm particles were viewed at 10× magnification (FIG. 8) and starch and fiber particles were viewed at 100× magnification (FIG. 9).

Figure 11:
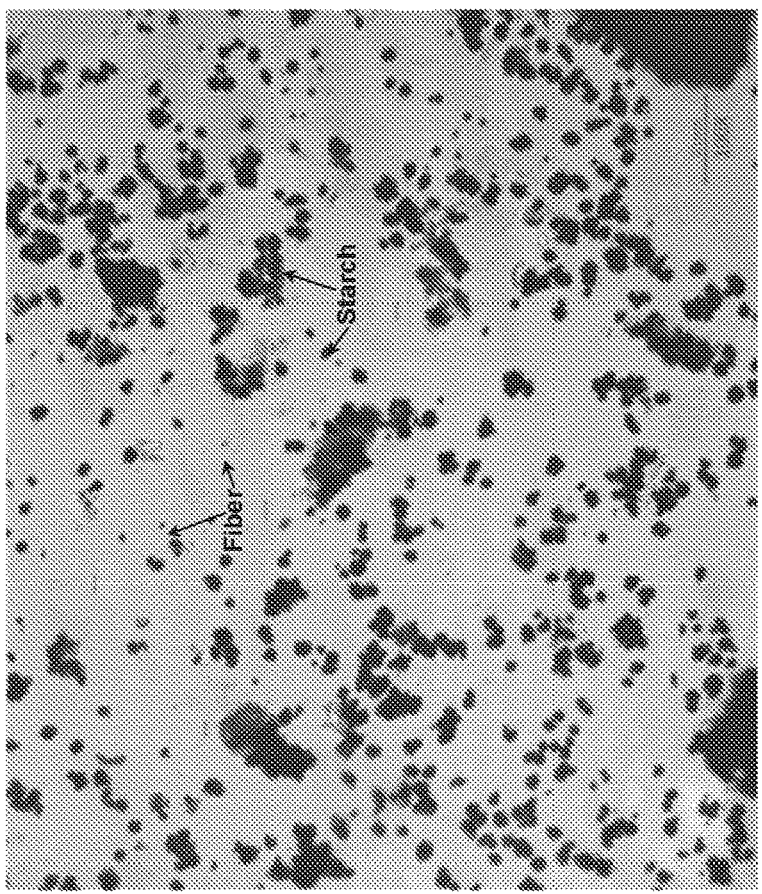
FIG. 11 is an optical microscope image of disk pulverized corn (Example 2) at a magnification of 100×.
Figure 10:
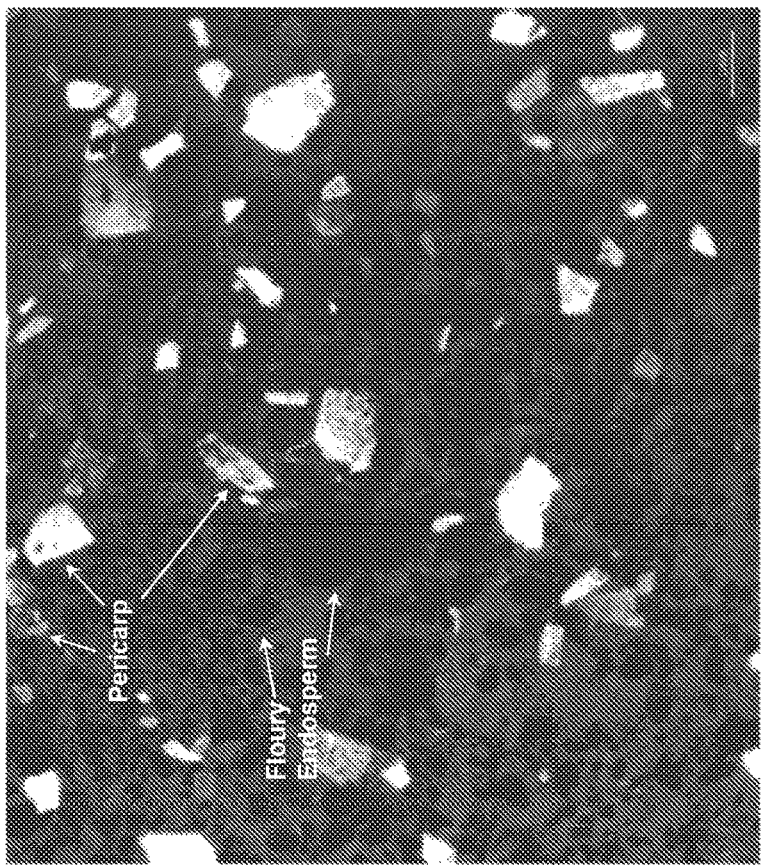
FIG. 10 is an optical microscope image of disk pulverized corn (Example 2) at a magnification of 10×.

In the Ex. 3 sample of disk fiberized corn, pericarp and floury endosperm particles were viewed at 10× magnification (FIG. 10) and starch and fiber particles were viewed at 200× magnification (FIG. 11).

Figure 13:
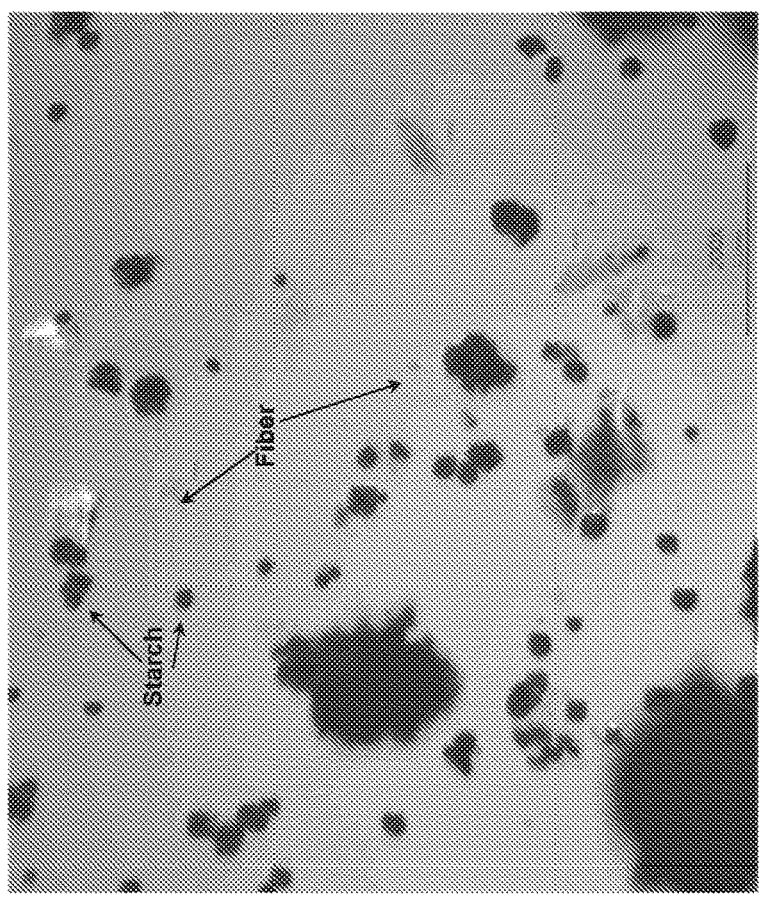
FIG. 13 is an optical microscope image of disk fiberized corn (Example 3) at a magnification of 200×.
Figure 12:
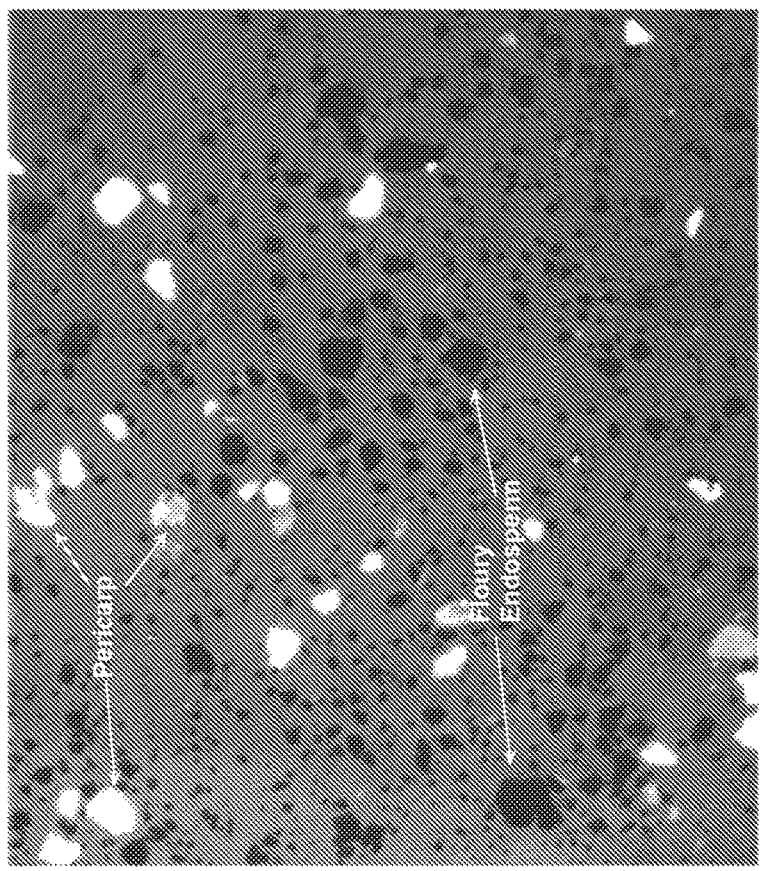
FIG. 12 is an optical microscope image of disk fiberized corn (Example 3) at a magnification of 10×.
Figures 14, 15:
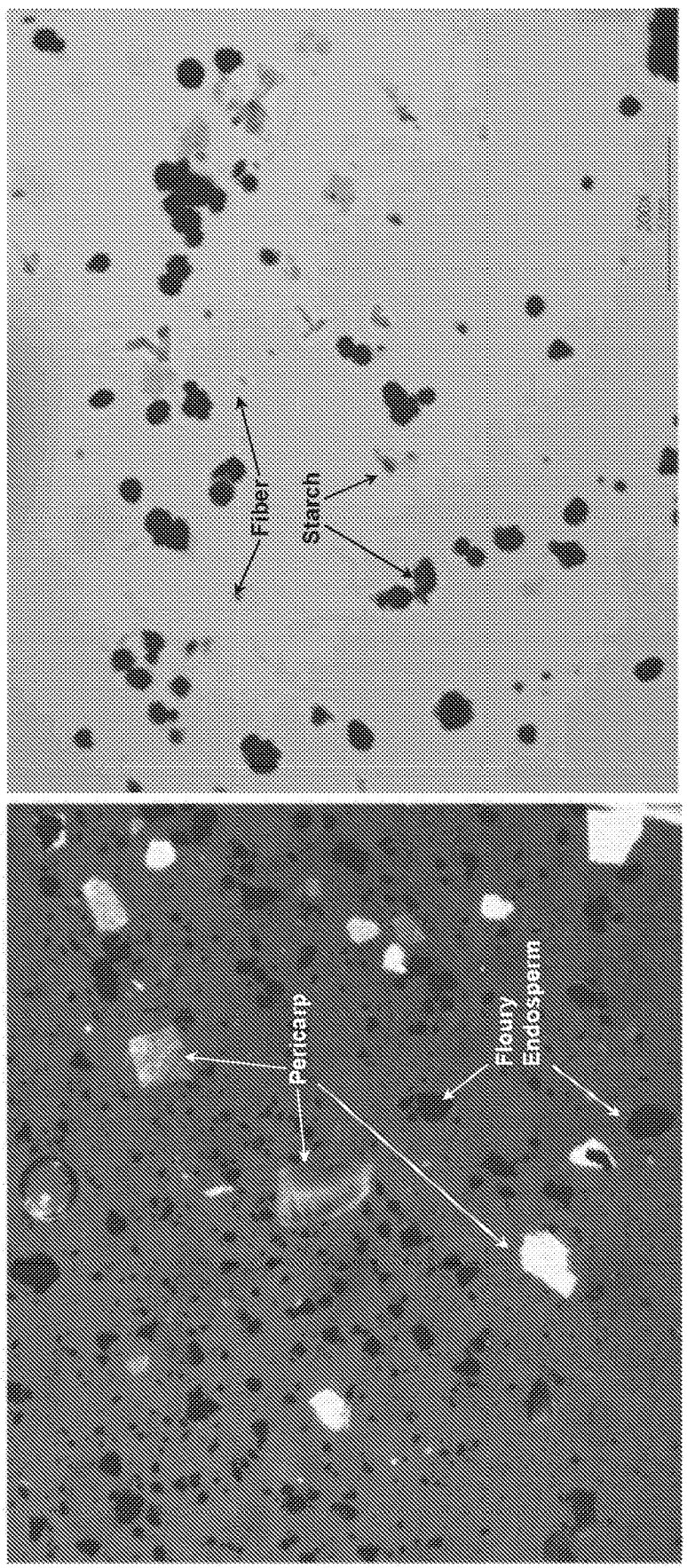
FIG. 14 is an optical microscope image of disk fiberized corn (Example 4) at a magnification of 10×.
FIG. 15 is an optical microscope image of disk fiberized corn (Example 4) at a magnification of 200×.

In the Ex. 4 sample of disk fiberized corn, pericarp and floury endosperm particles were viewed at 10× magnification (FIG. 12) and starch and fiber particles were viewed at 200× magnification (FIG. 13).

Secondary Fermentation

Secondary fermentation was conducted on four fiber containing samples. The first sample (Comparative Example 3 (CEx. 3)) was a wet cake produced by separating ethanol from a fermentation mash to provide the wet cake. The ground corn that was subjected to the first or primary fermentation that produced the fermentation mash was ground with a hammermill (Roskamp Champion Champion Series 48×38). The particle size distribution of the ground corn is similar to the CEx. 1 distribution given above. The whole stillage was not subjected to a fiber/protein separation process.

The second sample (Example 5 (Ex. 5)) was a fiber product produced by separating a whole stillage into a fiber rich product and a protein product. The ground corn that was subjected to the first or primary fermentation that produced the fermentation mash from which the whole stillage was separated was ground with a hammermill (Roskamp Champion Champion Series 48×38). The particle size distribution of the ground corn was similar to the CEx. 1 distribution given above.

The third sample (Example 6 (Ex. 6)) was a fiber product produced by separating a whole stillage into a fiber rich product and a protein product. The ground corn that was subjected to the first or primary fermentation that produced the fermentation mash from which the whole stillage was separated was ground with the disk mill fiberizer. i.e., Model TOQ-18 fiberizer, manufactured by Reynolds Engineering & Equipment. Inc. in Muscatine. Iowa.

The fourth sample (Example 7 (Ex. 7)) was a fiber product produced by separating a whole stillage into a fiber rich product and a protein product. The ground corn that was subjected to the first or primary fermentation that produced the fermentation mash from which the whole stillage was separated was ground with the disk mill fiberizer. i.e., Model TOQ-18 fiberizer, manufactured by Reynolds Engineering & Equipment. Inc. in Muscatine, Iowa. This ground corn had a similar particle size distribution as Example 3 above.

Ex 6 and Ex 7 were separate fermentation batches of different lots of corn that were milled to the same specification. The only difference in the separation process that was used between Ex. 6 and Ex. 7 is that a smaller screen size was used to separate the fibers from the protein in the whole stillage. More particularly, a fiber screen size of about 45 μm was used to separate the fiber product of Ex. 6, whereas a fiber screen size of about 20 μm was used to separate the fiber product of Ex. 7. The filter used was an FF6 Fiber Filter from Vincent Corporation, Tampa Fla.

The composition of CEx. 3 and Exs. 5-7 was determined and the results are shown in Table 5 below.

sion 2005; Determination of Extractives in Biomass Version 2005; Determination of Total Solids in Biomass Version 2008; Determination of Structural Carbohydrates and Lignin in Biomass Version 2012; and Determination of Starch in Solid Biomass Sample Version 2005.

The ethanol potential per 1,000 kg of each fiber containing sample was calculated and the results are shown in Table 7 below. The ethanol potential was determined according to the procedure discussed and described above. For illustrative purposes, the determination of the ethanol potential of Ex. 6, a fiber rich product (FRP) was calculated as follows.

The amount of glucan, galactan, mannan and starch (20.71 wt % of glucan, 6.93 wt % of galactan, 0 wt % of mannan, and 2.84 wt % of starch) were added together and equaled a total of 30.48 wt % of glucan, galactan, mannan and starch. The amount (wt %) of the combined amount of glucan, galactan, mannan and starch was multiplied by 1,000 kg (0.3048×1,000) to determine the amount of any glucan, galactan, mannan, and starch in kilograms per 1,000 kg of the FRP, which was equal to 304.8 kg of glucan, galactan, mannan and starch per 1,000 kg of the FHP. The mass (kg) of glucan, galactan, mannan and starch per 1,000 kg of the FRP was converted to mass (kg) of monosaccharides per 1,000 kg of the FRP by multiplying the mass of the glucan, galactan, mannan, and starch (304.8 kg) by 1.11 to

TABLE 5

Compositional Analysis

| Example | Total Inorganics (%) | Structural Protein (%) | Total Extractives (%) | Acetate (%) | Lignin (%) | C6 Polysaccharide (%) | C5 Polysaccharide (%) | Fermentable Sugars (C5 + C6) % |
|---|---|---|---|---|---|---|---|---|
| CEx. 3 | 5.89 | 21.35 | 6.00 | 0.59 | 26.34 | 22.19 | 16.40 | 43.26 |
| Ex. 5 | 1.49 | 19.73 | 17.24 | 1.70 | 16.29 | 21.84 | 20.98 | 48.08 |
| Ex. 6 | 0.63 | 13.26 | 0.26 | 2.05 | 18.12 | 30.48 | 42.56 | 82.18 |
| Ex. 7 | 0.64 | 22.86 | 1.48 | 3.19 | 19.32 | 28.82 | 26.11 | 61.65 |
| *Bagasse | 2.83 | 0.75 | 4.38 | 2.40 | 23.71 | 44.07 | 25.36 | 77.73 |

*Bagasse was a baseline sample used to validate the compositional analysis

A more detailed compositional analysis of the inorganics, extractives, C6 polysaccharides, and C5 polysaccharides is shown in Table 6 below.

account for the molecule of water that adds to the polysaccharides when the sugar monomers are hydrolyzed from the polysaccharides, which was equal to 338.3 kg of monosac-

TABLE 6

Compositional Analysis Continued

| Example | Structural Inorganics (%) | Non-Structural Inorganics (%) | Water Extractables (%) | Ethanol Extractables (%) | Glucan (%) | Xylan (%) | Galactan (%) | Arabinan (%) | Mannan (%) | Starch (%) |
|---|---|---|---|---|---|---|---|---|---|---|
| CEx. 3 | 3.26 | 2.63 | 3.37 | 2.63 | 14.51 | 9.74 | 4.11 | 6.66 | not detected | 3.57 |
| Ex. 5 | 0.17 | 1.32 | 3.66 | 13.58 | 14.26 | 12.53 | 3.39 | 8.45 | not detected | 4.19 |
| Ex. 6 | 0.12 | 0.51 | 0.10 | 0.16 | 20.71 | 25.35 | 6.93 | 17.21 | not detected | 2.84 |
| Ex. 7 | 0.35 | 0.29 | 0.39 | 1.09 | 18.07 | 16.14 | 6.46 | 9.97 | not detected | 4.29 |
| *Bagasse | 1.87 | 0.96 | 2.41 | 1.97 | 41.68 | 23.76 | 2.39 | 1.60 | not detected | not detected |

*Bagasse was a baseline sample used to validate the compositional analysis

The tests used to determine the amounts in Tables 5 and 6 above were the standard tests used in the industry that are based on the National Renewable Energy Laboratory (NREL) Methods, NREL Chemical Analysis and Standard Testing Procedures: Determination of Ash in Biomass Vercharides per 1,000 kg of the FRP. The mass (kg) of the monosaccharides per 1,000 kg of the FRP was multiplied by 0.51 to convert the kilograms of monosaccharides per 1,000 kg of the FRP to kilograms ethanol per 1,000 kg of the FRP while assuming 100% of the theoretical yield, which was equal to 172.5 kg of ethanol per 1,000 kg of the FRP. The 172.5 kg of ethanol per 1,000 kg of the FRP was converted to liters (L) per 1,000 kg of the FRP by dividing the 172.5 kg of ethanol per 1,000 kg of the FRP by 0.789 kg/liter, which was equal to 218.7 liters of ethanol per 1,000 kg of the FRP. The 218.7 liters of ethanol per 1,000 kg of the FRP was divided by 3.789 to convert the amount of ethanol per 1,000 kg of the FRP to gallons of ethanol per 1,000 kg of the FRP, which was equal to 57.7 gallons of ethanol per 1,000 kg of the FRP.

The same calculations were done for the amounts of xylan and arabinan. The amount of xylan and arabinan (25.35 wt % of xylan and 17.21 wt % of arabinan) were added together and equaled a total of 42.56 wt % of xylan and arabinan. The amount (wt %) of the combined amount of xylan and arabinan was multiplied by 1,000 kg (0.4256×1,000 kg) to determine the amount of any xylan and arabinan in kilograms per 1,000 kg of the FRP, which was equal to 425.6 kg of xylan and arabinan per 1,000 kg of the FRP. The mass (kg) of xylan and arabinan per 1,000 kg of the FRP was then converted to the mass (kg) of monosaccharides per 1,000 kg of the FRP by multiplying the mass of the xylan and arabinan (425.6 kg) by 1.136 to account for the molecule of water that adds to the polysaccharides when the sugar monomers are hydrolyzed from the polysaccharides, which was equal to 483.5 kg of monosaccharides per 1,000 kg of the FRP. The mass (kg) of the monosaccharides per 1,000 kg of the FRP was multiplied by 0.51 to convert the kilograms of monosaccharides per 1,000 kg of the FRP to kilograms of ethanol per 1,000 kg of the FRP while assuming 100% of the theoretical yield, which was equal to 246.6 kg of ethanol per 1,000 kg of the FRP. The 246.6 kg of ethanol per 1,000 kg of the FRP was converted to liters (L) per 1,000 kg of the FRP by dividing the 246.6 kg of ethanol per 1,000 kg of the FRP by 0.789 kg/liter, which was equal to 312.5 liters of ethanol per 1,000 kg of the FRP. The 312.5 liters of ethanol per 1,000 kg of the FRP was divided by 3.789 to convert the amount of ethanol per 1,000 kg of the FRP to gallons of ethanol per 1,000 kg of the FRP, which was equal to 82.5 gallons of ethanol per 1,000 kg of the FRP.

Accordingly, the ethanol potential of the fiber rich product of Ex. 6 was equal to the combined amount of ethanol derived from the glucan, galactan, mannan, and starch (57.7 gallons of ethanol per 1,000 kg of the FRP) and the amount of ethanol derived from xylan and arabinan (82.5 gallons of ethanol per 1,000 kg of the FRP), which was equal to 140.2 gallons of ethanol per 1,000 kg of fiber rich product.

TABLE 7

| | Ethanol Potential | | | |
|---|---|---|---|---|
| | CEx. 3 (gallons of ethanol per 1,000 kilograms of the wet cake on a dry basis) | Ex. 5 (gallons of ethanol per 1,000 kilograms of the FRP) | Ex. 6 (gallons of ethanol per 1,000 kilograms of the FRP) | Ex. 7 (gallons of ethanol per 1,000 kilograms of the FRP) |
| Ethanol Potential | 73.8 | 82.0 | 140.2 | 105.1 |

As shown in Table 7, the fiber product recovered from the whole stillage that was produced with corn ground in the disk mill fiberizer (Exs. 6 and 7) had a significantly greater ethanol potential than CEx. 3. More particularly, Ex. 6 had the potential to make about 1.90 times the amount of ethanol as CEx. 3 and Ex. 7 had the potential to make about 1.42 times the amount of ethanol as CEx. 3.

Acid Pretreatment of Fiber Containing Samples

The fiber samples (CEx. 3 and Exs. 5-7) were subjected to an acid pretreatment process to produce pre-treated fiber containing samples. All supplies were purchased from ThermoFisher and Sigma Aldrich and used as received. The moisture level of each substrate was determined by the moisture balance and following the manufacturer's suggested usage.

The fiber containing samples were all pretreated to convert the hemicellulose to oligomers, xylose, and arabinose and to make the cellulose and hemicellulosic oligomers more accessible and digestible to cellulase enzymes. The acid used in these experiments was about 93% sulfuric acid containing about 7% water. The pretreatments were all setup with a set amount of sample, water, and acid which were mixed together and placed in an autoclavable vessel or jar with a lid. The lid was sealed. The full jar was placed into an autoclave and heated to about 120° C. for about 2 hours.

The water in the acid as well as the water in the fiber containing samples were accounted for in the calculations to maintain the required solids and acid loadings. The added water was tap water from the City of Wichita, Kans. The amount of fiber containing sample was 100 grams on a dry weight basis (DWB). Table 8 provides the setup for these examples.

TABLE 8

| | Acid Pretreatment | | | | | | | | |
|---|---|---|---|---|---|---|---|---|---|
| | Mass of Sample (g) | Moisture Content (%) | Moisture in Fiber (g) | Fiber DWB (g) | Total Weight (g) | Water (g) | Acid (g) | Water in Acid (g) | Acid Loading (g/Kg) |
| CEx. 3 | 219 | 54.3 | 119 | 100 | 300 | 80.6 | 0.54 | 0.04 | 5 |
| Ex. 5 | 258.4 | 61.3 | 158.4 | 100 | 300 | 41 | 0.54 | 0.04 | 5 |
| Ex. 6 | 111.6 | 10.4 | 11.6 | 100 | 300 | 187.8 | 0.54 | 0.04 | 5 |
| Ex. 7 | 104.2 | 4 | 4.2 | 100 | 300 | 195.3 | 0.54 | 0.04 | 5 |

The acid-treated fiber containing material was allowed to cool upon removal from the autoclave and the moisture content was determined to calculate a recovery of pretreated fiber substrate.

Enzyme Hydrolysis of the Acid Pretreated Fiber Containing Samples

Once the acid pretreatments were completed, the acid pretreated solids were hydrolyzed, which as discussed and described above can be accomplished with two enzyme systems. The first system was a cocktail of enzymes that is termed by the industry as a cellulase, but contains exo-glucanases, endo-gluconases, beta-glucosidase, and potentially some xylanase activity. The second enzyme system was a hemicellulase and may contain a number of different activities including exo-xylanase, endo-xylanase, arabinose, esterase, and proteases. These enzyme cocktails are available commercially from Novozymes (Franklinton N.C.) and DuPont (Wilmington Del.).

The specific process variables for the enzyme hydrolysis of the acid pretreated fiber containing samples is shown in Table 9 below. The moisture or solids content of each acid pretreated fiber containing sample was used to determine the amount of wet material to use in order to obtain 15 g of the acid pretreated fiber containing sample on a dry weight basis. This amount was weighed into an appropriately sized plastic container (about 250 mL container) to hold 100 g of enzyme hydrolysis solids and liquid) with a screw on lid (to provide a water tight seal), followed by the addition of water, the pH of each sample was adjusted to about 5 to about 5.2, the enzyme was added, and the lid was closed. The 250 mL containers were placed in a heated mechanical shaker set to about 50° C., and a shake rpm of about 150. The hydrolysis was allowed to proceed for a time of about 72 hours with the pH adjusted back to about 5 to about 5.2 at each 24 hour period. At 72 hours, the containers were removed from the shaker and the contents of each container was centrifuged to separate the residual solids from the liquid sugar solution. The separated sugar solution was filtered through a 0.20 μm syringe filter into HPLC vials or into a 96 well plate for analysis to determine the amount of sugar released by pretreatment and enzyme hydrolysis.

The results showing the sugar concentrations of the enzyme hydrolyzed acid pretreated fiber containing sample are shown in Table 10 below. Three separate sugar analysis were conducted for each example and the average of those three tests is shown in Table 10. The sugar analysis results were collected from a YSI biochemistry analyzer (2950D YSI Incorporated, 1700/1725 Brannum Lane, Yellow Springs, Ohio 45387-1107 USA.

TABLE 10

Sugar Concentrations for Enzyme Hydrolyzed Acid Pretreated Fiber Containing Samples

| Feed Stock | Glucose (g/L) | Std. Dev. | Xylose (g/L) | Std. Dev. |
|---|---|---|---|---|
| CEx. 3 | 14.5 | 3.33 | 3.6 | 0.39 |
| Ex. 5 | 10.0 | 2.16 | 5.1 | 0.21 |
| Ex. 6 | 35.5 | 2.30 | 6.6 | 1.34 |
| Ex. 7 | 26.8 | 1.28 | 4.7 | 1.99 |

The results showing the sugar yields for each enzyme hydrolyzed acid pretreated fiber containing sample is shown in Table 11 below.

TABLE 11

Sugar Yields for Enzyme Hydrolyzed Acid Pretreated Fiber Containing Samples

| | Glucose Yield (%) | Glucose Std Dev | Xylose Yield (%) | Xylose Std Dev |
|---|---|---|---|---|
| CEx. 3 | 48.3 | 11.06 | 21.67 | 2.33 |
| Ex. 5 | 32.58 | 7.05 | 24 | 0.97 |
| Ex. 6 | 90.5 | 5.86 | 15.21 | 3.1 |
| Ex. 7 | 71.85 | 3.44 | 17.27 | 7.24 |

Base Pretreatment of Fiber Containing Samples

The structure of the fibers can also be disrupted with a base instead of an acid. Accordingly, the fiber samples (CEx. 3 and Exs. 5-7) were also subjected to a base pretreatment process to produce pre-treated fiber containing samples. Pretreatment with a base induces very little hydrolysis compared to when an acid is used. The base partially solubilizes or swells the cellulose and hemicellulose.

The base used in these experiments was an aqueous ammonium hydroxide solution containing about 30% ammonium hydroxide and about 70% water. The water in the base solution as well as the water in the substrate were accounted for in the calculations to maintain the solids and base loadings required. The added water was tap water (City of Wichita Kans.). The material was allowed to cool upon removal from the autoclave followed a new moisture determination and a weighing to calculate a recovery of pre-treated fiber substrate. The base loading is calculated for ammonia ($NH_3$).

The base pretreatment was setup with a set amount of the fiber containing material, water, and base that were mixed together and placed in an autoclavable vessel and the vessel was sealed with a lid. The vessels were placed into an autoclave and heated to 120° C. for about 2 hours. Table 12 provides the setup for these examples.

TABLE 9

Process Conditions for Enzyme Hydrolyzed Acid Pretreated Fiber Containing Samples

| | Pretreated fiber containing sample (mass fraction) | Target Fermentor Solids (mass frac) | Dry Pretreated Solids (g) | As-is Pretreated Solids (g)-Total | Makeup Water to Add (mL) | Enzyme Dose (g enzyme/ g TS) | Enzyme Amount to Add (g) | Enzyme Dose (g enzyme/ g TS) | Enzyme Amount to Add (g) |
|---|---|---|---|---|---|---|---|---|---|
| CEx. 3 | 0.317 | 0.15 | 15 | 54.3 | 50.18 | 0.13 | 1.29 | 0.05 | 0.75 |
| Ex. 5 | 0.363 | 0.15 | 15 | 41.3 | 56.38 | 0.13 | 1.29 | 0.05 | 0.75 |
| Ex. 6 | 0.343 | 0.15 | 15 | 43.7 | 53.97 | 0.13 | 1.29 | 0.05 | 0.75 |
| Ex. 7 | 0.347 | 0.15 | 15 | 43.2 | 54.47 | 0.13 | 1.29 | 0.05 | 0.75 |

TABLE 12

| | Mass of Sample (g) | Moisture Content (%) | Moisture in Fiber (g) | Fiber DWB (g) | Total Weight (g) | Water (g) | Base (g) | Water in Base (g) | Base Loading (g/Kg) |
|---|---|---|---|---|---|---|---|---|---|
| | | | | Base Pretreatment | | | | | |
| CEx. 3 | 184.2 | 45.7 | 84.2 | 100 | 300 | 110.9 | 6.9 | 4.9 | 20 |
| Ex. 5 | 258.4 | 61.3 | 158.4 | 100 | 300 | 36.7 | 6.9 | 4.9 | 20 |
| Ex. 6 | 111.6 | 10.4 | 11.6 | 100 | 300 | 183.5 | 6.9 | 4.9 | 20 |
| Ex. 7 | 104.2 | 4.0 | 4.2 | 100 | 300 | 190.9 | 6.9 | 4.9 | 20 |

Enzyme Hydrolysis of the Base Pretreated Fiber Containing Samples

Once the base pretreatments were completed, the base pretreated solids were hydrolyzed, which, as discussed above, can be accomplished with two enzyme systems. The first system was a cocktail of enzymes that is termed by the industry as a cellulase, but contains exo-glucanases, endo-gluconases, beta-glucosidase, and potentially some xylanase activity. The second enzyme system was as a hemicellulase and may contain a number of different activities including exo-xylanase, endo-xylanase, arabinose, esterase, and proteases. These enzyme cocktails were acquired from Novozymes (Franklinton N.C.) and DuPont (Wilmington Del.).

The moisture or solids content of each base pretreated fiber containing sample was used to determine the amount of wet material to use in order to obtain 15 g of the base pretreated fiber containing sample on a dry weight basis. This amount was weighed into an appropriately sized plastic container (about 250 mL container) to hold 100 g of enzyme hydrolysis solids and liquid) with a screw on lid (to provide a water tight seal), followed by the addition of water, the pH of each sample was adjusted to about 5 to about 5.2, the enzyme was added, and the lid was closed. The 250 mL containers were placed in a heated mechanical shaker set to about 50° C., and a shake rpm of about 150. The hydrolysis was allowed to proceed for a time of about 72 hours with the pH adjusted back to about 5 to about 5.2 at each 24 hour period. At 72 hours, the containers were removed from the shaker and the contents of each container was centrifuged to separate the residual solids from the liquid sugar solution. The separated sugar solution was filtered through a 0.20 μm syringe filter into HPLC vials or into a 96 well plate for analysis to determine the amount of sugar released by pretreatment and enzyme hydrolysis. The specific process variables for the enzyme hydrolysis of the base pretreated fiber containing samples is shown in Table 13 below.

The results showing the sugar concentrations of the enzyme hydrolyzed base pretreated fiber containing sample is shown in Table 14 below. Three separate sugar analysis was conducted on each example and the average of those three tests is shown in Table 14. The sugar analysis results were collected from a YSI biochemistry analyzer (2950D YSI Incorporated, 1700/1725 Brannum Lane, Yellow Springs, Ohio 45387-1107 USA.

TABLE 14

| | Sugar Concentrations for Base Pretreated Fiber Containing Samples | | | |
|---|---|---|---|---|
| | Glucose (g/L) | Std. Dev. | Xylose (g/L) | Std. Dev. |
| CEx. 3 | 8.7 | 2.8 | 4.9 | 0.7 |
| Ex. 5 | 11.3 | 3.3 | 6.8 | 1 |
| Ex. 6 | 22.1 | 1 | 10.1 | 1 |
| Ex. 7 | 14.1 | 3.6 | 8.9 | 0.6 |

The results showing the sugary yields for each enzyme hydrolyzed base pretreated fiber containing sample is shown in Table 15 below.

TABLE 15

| | Sugar Yields for Enzyme Hydrolyzed Base Pretreated Fiber Containing Samples | | | |
|---|---|---|---|---|
| | Glucose Yield (%) | Glucose Std Dev | Xylose Yield (%) | Xylose Std Dev |
| CEx. 3 | 28.81 | 9.39 | 29.25 | 4.05 |
| Ex. 5 | 36.90 | 10.61 | 31.56 | 2.83 |
| Ex. 6 | 56.37 | 2.48 | 23.49 | 2.35 |
| Ex. 7 | 37.89 | 9.71 | 32.29 | 2.36 |

Embodiments of the present disclosure further relate to any one or more of the following paragraphs:

1. A process for making ethanol, comprising: processing a ground corn product to produce a fermentation mash comprising ethanol; separating at least a portion of the ethanol from the fermentation mash to produce a whole stillage; and separating the whole stillage to produce a fiber rich product and a filtrate, wherein the fiber rich product has an ethanol potential of at least 90 gallons of ethanol per 1,000 kilograms of the fiber rich product.

TABLE 13

| | Process Conditions for Enzyme Hydrolyzed Base Pretreated Fiber Containing Samples | | | | | | | | |
|---|---|---|---|---|---|---|---|---|---|
| | PT Material Solids (mass frac) | Target Fermentor Solids (mass frac) | Dry Pretreated Solids (g) | As-is Pretreated Solids (g)-Total | Makeup Water to Add (mL) | Enzyme Dose (g enzyme/ g TS) | Enzyme Amount to Add (g) | Enzyme Dose (g enzyme/ g TS) | Enzyme Amount to Add (g) |
| CEx. 3 | 0.281 | 0.15 | 15 | 53.4 | 45.31 | 0.06 | 0.94 | 0.03 | 0.38 |
| Ex. 5 | 0.322 | 0.15 | 15 | 46.6 | 52.1 | 0.06 | 0.94 | 0.03 | 0.38 |
| Ex. 6 | 0.336 | 0.15 | 15 | 44.6 | 54.04 | 0.06 | 0.94 | 0.03 | 0.38 |
| Ex. 7 | 0.368 | 0.15 | 15 | 40.8 | 57.93 | 0.06 | 0.94 | 0.03 | 0.38 |

2. A process for making ethanol, comprising: processing a ground corn product to produce a fermentation mash comprising ethanol; separating at least a portion of the ethanol from the fermentation mash to produce a whole stillage; separating the whole stillage to produce a fiber rich product and a filtrate; hydrolyzing the fiber rich product to produce a saccharification mash; and processing the saccharification mash to produce additional ethanol and a stillage protein product.

3. A process for recovering products from a corn fermentation mash, comprising: processing a ground corn product to produce a fermentation mash comprising ethanol; separating at least a portion of the ethanol from the fermentation mash to produce a whole stillage; separating the whole stillage with a fiber filter to produce a fiber rich product and a filtrate; hydrolyzing the fiber rich product to produce a saccharification mash; processing the saccharification mash to produce additional ethanol and a stillage protein product.

4. A process for recovering products from a corn fermentation mash, comprising: separating ethanol from a fermentation mash to produce a whole stillage, wherein the fermentation mash is derived from a ground corn product milled from a plurality of corn pieces, wherein the plurality of corn pieces comprises whole corn kernels, fragmented corn kernels, size-reduced corn kernels, milled corn kernels, or any mixture thereof, wherein greater than 80 wt % of the ground corn product has a particle size of 425 µm or less, as measured according to AOAC 965.22-1966; separating the whole stillage to produce a fiber rich product and a filtrate; hydrolyzing the fiber rich product to produce a saccharification mash; and processing the saccharification mash to produce additional ethanol and a stillage protein product.

5. A process for recovering products from a corn fermentation mash, comprising: processing a ground corn product to produce a fermentation mash comprising ethanol; separating at least a portion of the ethanol from the fermentation mash to produce a whole stillage; and separating the whole stillage with a separator to produce a fiber rich product and a filtrate, wherein the separator comprises a rotary drum screen, a rotary vacuum drum filter, a brush strainer, a vibratory separator, a linear motion screen, a vacu-deck screen, or a combination thereof; hydrolyzing the fiber rich product to produce a saccharification mash; and processing the saccharification mash to produce additional ethanol and a stillage protein product.

6. A process for making ethanol, comprising: processing a ground corn product to produce a fermentation mash comprising ethanol; separating at least a portion of the ethanol from the fermentation mash to produce a whole stillage; separating the whole stillage to produce a fiber rich product and a filtrate; processing the fiber rich product to produce additional ethanol and a stillage protein product comprising about 40 wt % to about 80 wt % of protein, about 3 wt % to about 20 wt % of fat, about 1 wt % to about 4 wt % of ash, about 2 wt % to about 30 wt % of neutral detergent fibers, about 1 wt % to about 15 wt % of acid detergent fibers, and about 15 wt % to about 35 wt % of yeast, based on a dry weight of the stillage protein product.

7. A process for making ethanol, comprising: processing a ground corn product to produce a fermentation mash comprising ethanol; separating at least a portion of the ethanol from the fermentation mash to produce a whole stillage; separating the whole stillage to produce a fiber rich product and a filtrate; processing the fiber rich product to produce additional ethanol and a stillage protein product comprising about 15 wt % to about 35 wt % of yeast, based on a dry weight of the stillage protein product.

8. A process for recovering products from a corn fermentation mash, comprising: processing a ground corn product to produce a fermentation mash comprising ethanol, wherein the ground corn product has a $d_{50}$ by volume percent of 100 µm to 400 µm, as measured according to ISO 13320:2009; separating at least a portion of the ethanol from the fermentation mash to produce a whole stillage; separating the whole stillage with a single pressure screen to produce a fiber rich product and a filtrate; and processing the fiber rich product to produce additional ethanol and a stillage protein product.

9. A process for recovering products from a corn fermentation mash, comprising: processing a ground corn product to produce a fermentation mash, wherein the ground corn product has a $d_{50}$ by volume percent of 100 µm to 400 µm, as measured according to ISO 13320:2009; separating ethanol from the fermentation mash to produce a whole stillage; separating the whole stillage with a fiber filter to produce a fiber rich product and a filtrate; and processing the fiber rich product to produce additional ethanol and a stillage protein product.

10. A process for recovering products from a corn fermentation mash, comprising: processing a ground corn product to produce a fermentation mash, wherein greater than 25 wt % of the ground corn product has a particle size of greater than 105 µm, and wherein greater than 80 wt % of the ground corn product has a particle size of 425 µm or less, as measured according to AOAC 965.22-1966; separating ethanol from the fermentation mash to produce a whole stillage; separating the whole stillage to produce a fiber rich product and a filtrate; hydrolyzing the fiber rich product to produce a saccharification mash; and processing the saccharification mash to produce additional ethanol and a stillage protein product.

11. A process for making ethanol, comprising: processing a ground corn product to produce a fermentation mash comprising ethanol; separating ethanol from the fermentation mash to produce a whole stillage; separating the whole stillage to produce a fiber rich product and a filtrate; and processing the fiber rich product to produce additional ethanol and a stillage protein product.

12. A process for recovering products from a corn fermentation mash, comprising: processing a ground corn product to produce a fermentation mash comprising ethanol; separating at least a portion of the ethanol from the fermentation mash to produce a whole stillage; separating the whole stillage with a fiber filter to produce a fiber rich product and a filtrate; and processing the fiber rich product to produce additional ethanol and a stillage protein product.

13. A process for recovering products from a corn fermentation mash, comprising: separating ethanol from a fermentation mash to produce a whole stillage, wherein the fermentation mash is derived from aground corn product milled from a plurality of corn pieces, wherein the plurality of corn pieces comprises whole corn kernels, fragmented corn kernels, size-reduced corn kernels, milled corn kernels, or any mixture thereof, wherein greater than 80 wt % of the ground corn product has a particle size of 425 µm or less, as measured according to AOAC 965.22-1966; separating the whole stillage to produce a fiber rich product and a filtrate; and processing the fiber rich product to produce additional ethanol and a stillage protein product.

14. A process for recovering products from a corn fermentation mash, comprising: processing a ground corn product to produce a fermentation mash comprising ethanol; separating at least a portion of the ethanol from the fermentation mash to produce a whole stillage; and separating the whole stillage with a separator to produce a fiber rich product and a filtrate, wherein the separator comprises a rotary drum screen, a rotary vacuum drum filter, a brush strainer, a vibratory separator, a linear motion screen, a vacu-deck screen, or a combination thereof; and processing the fiber rich product to produce additional ethanol and a stillage protein product.

15. A process for recovering products from a corn fermentation mash, comprising: processing a ground corn product to produce a fermentation mash, wherein greater than 25 wt % of the ground corn product has a particle size of greater than 105 μm, and wherein greater than 80 wt % of the ground corn product has a particle size of 425 μm or less, as measured according to AOAC 965.22-1966; separating ethanol from the fermentation mash to produce a whole stillage; separating the whole stillage to produce a fiber rich product and a filtrate; and processing the fiber rich product to produce additional ethanol and a stillage protein product.

16. The process according to any one of paragraphs 2 to 15, wherein the fiber rich product has an ethanol potential of at least 90 gallons of ethanol per 1,000 kilograms of the fiber rich product.

17. The process according to any one of paragraphs 1 to 15, wherein the fiber rich product has an ethanol potential of at least 95 gallons of ethanol per 1,000 kilograms of the fiber rich product.

18. The process according to any one of paragraphs 1 to 15, wherein the fiber rich product has an ethanol potential of at least 100 gallons of ethanol per 1,000 kilograms of the fiber rich product.

19. The process according to any one of paragraphs 1 to 15, wherein the fiber rich product has an ethanol potential of at least 105 gallons of ethanol per 1,000 kilograms of the fiber rich product.

20. The process according to any one of paragraphs 1 to 15, wherein the fiber rich product has an ethanol potential of at least 110 gallons of ethanol per 1,000 kilograms of the fiber rich product.

21. The process according to any one of paragraphs 1 to 15, wherein the fiber rich product has an ethanol potential of at least 115 gallons of ethanol per 1,000 kilograms of the fiber rich product.

22. The process according to any one of paragraphs 1 to 15, wherein the fiber rich product has an ethanol potential of at least 120 gallons of ethanol per 1,000 kilograms of the fiber rich product.

23. The process according to any one of paragraphs 1 to 15, wherein the fiber rich product has an ethanol potential of at least 125 gallons of ethanol per 1,000 kilograms of the fiber rich product.

24. The process according to any one of paragraphs 1 to 15, wherein the fiber rich product has an ethanol potential of at least 130 gallons of ethanol per 1,000 kilograms of the fiber rich product.

25. The process according to any one of paragraphs 1 to 15, wherein the fiber rich product has an ethanol potential of at least 135 gallons of ethanol per 1,000 kilograms of the fiber rich product.

26. The process according to any one of paragraphs 1 to 15, wherein the fiber rich product has an ethanol potential of at least 140 gallons of ethanol per 1,000 kilograms of the fiber rich product.

27. The process according to any one of paragraphs 1 to 26 wt % herein the fiber rich product has an ethanol potential of up to about 145 gallons of ethanol per 1,000 kilograms of the fiber rich product.

28. The process according to any one of paragraphs 1 to 26, wherein the fiber rich product has an ethanol potential of up to about 150 gallons of ethanol per 1,000 kilograms of the fiber rich product.

29. The process according to any one of paragraphs 1 to 26, wherein the fiber rich product has an ethanol potential of up to about 155 gallons of ethanol per 1,000 kilograms of the fiber rich product.

30. The process according to any one of paragraphs 1 to 26, wherein the fiber rich product has an ethanol potential of up to about 160 gallons of ethanol per 1,000 kilograms of the fiber rich product.

31. The process according to any one of paragraphs 1 to 15, wherein the fiber rich product has an ethanol potential of about 100 gallons of ethanol per 1,000 kilograms of the fiber rich product to about 150 gallons of ethanol per 1,000 kilograms of the fiber rich product.

32. The process according to any one of paragraphs 1 to 15, wherein the fiber rich product has an ethanol potential of about 135 gallons of ethanol per 1,000 kilograms of the fiber rich product to about 150 gallons of ethanol per 1,000 kilograms of the fiber rich product.

33. The process according to any one of paragraphs 1 to 15, wherein the fiber rich product has an ethanol potential of about 95 gallons of ethanol per 1,000 kilograms of the fiber rich product to about 110 gallons of ethanol per 1,000 kilograms of the fiber rich product.

34. The process according to any one of paragraphs 1 to 33, wherein greater than 80 wt % of the ground corn product has a particle size of 425 μm or less, as measured according to AOAC 965.22-1966.

35. The process according to any one of paragraphs 1 to 34, wherein the ground corn product has a $d_{50}$ by volume percent of 100 μm to 400 μm, as measured according to ISO 13320:2009.

36. The process according to any one of paragraphs 1 to 35, wherein greater than 85 wt % of the ground corn product has a particle size of 425 μm or less, as measured according to AOAC 965.22-1966.

37. The process according to paragraphs 1 to 36, wherein the ground corn product has a crystallinity of greater than 75%, as compared to a crystallinity of the corn pieces.

38. The process according to any one of paragraphs 1 to 37, wherein greater than 94 wt % of the ground corn product has a particle size of 425 μm or less, as measured according to AOAC 965.22-1966.

39. The process according to any one of paragraphs 1 to 38, wherein the ground corn product has a ds) by volume percent of 120 μm to 350 μm, as measured according to ISO 13320:2009.

40. The process according to any one of paragraphs 1-4, 6, 7, 9, 10-13, and 15-39, wherein the whole stillage is separated with a fiber filter to produce the fiber rich product and the filtrate, and wherein the fiber filter comprises a filter sleeve having openings of about 10 μm to about 400 μm.

41. The process according to any one of paragraphs 1 to 40, further comprising: separating the filtrate to produce a protein rich portion, an oil product, and a clarified stillage.

42. The process according to paragraph 41, further comprising removing water from the protein rich portion to produce a protein rich product.

43. The process according to paragraph 41 or 42, further comprising removing water from the clarified stillage to produce an evaporated clarified stillage.

44. The process according to any one of paragraphs 1 to 43, wherein the stillage protein product comprises about 15 wt % to about 35 wt % of yeast, based on a dry weight of the stillage protein product.

45. The process according to any one of paragraphs 1 to 43, wherein the stillage protein product comprises about 20 wt % to about 30 wt % of yeast, based on a dry weight of the stillage protein product.

46. The process according to any one of paragraphs 1 to 43, wherein the stillage protein product comprises about 20 wt % to about 27 wt % of yeast, based on a dry weight of the stillage protein product.

47. The process according to any one of paragraphs 1 to 43, wherein the stillage protein product comprises at least 20 wt % to about 30 wt % of yeast, based on a dry weight of the stillage protein product.

48. The process according to any one of paragraphs 1 to 43, wherein the stillage protein product comprises about 40 wt % to about 80 wt % of protein, about 3 wt % to about 20 wt % of fat, about 1 wt % to about 4 wt % of ash, about 2 wt % to about 30 wt/% of neutral detergent fibers, about 1 wt % to about 15 wt % of acid detergent fibers, and about 15 wt % to about 35 wt % of yeast, based on a dry weight of the stillage protein product.

49. The process according to any one of paragraphs 1 to 43, wherein the stillage protein product comprises about 47 wt % to about 57 wt % of protein, about 3 wt % to about 5 wt % of fat, about 1 wt % to about 3 wt % of ash, about 4 wt % to about 10 wt % of neutral detergent fibers, about 5 wt % to about 10 wt % of acid detergent fibers, and about 20 wt % to about 30 wt % of yeast, based on a dry weight of the stillage protein product.

50. The process according to any one of paragraphs 2-5, 10, and 16-49, wherein the fiber rich product is contacted with an acid prior to hydrolyzing the fiber rich product to produce the saccharification mash.

51. The process according to any one of paragraphs 2-5, 10, and 16-49, wherein the fiber rich product is contacted with a base prior to hydrolyzing the fiber rich product to produce the saccharification mash.

52. The process according to any one of paragraphs 2-5, 10, and 16-49, wherein the fiber rich product is contacted with an acid and a base prior to hydrolyzing the fiber rich product to produce the saccharification mash.

53. The process according to paragraph 50 and 52, wherein the acid comprises sulfuric acid, nitric acid, hydrochloric acid, phosphoric acid, strong acid resins, acetic acid, citric acid, trichloroacetic acid, or any mixture thereof.

54. The process according to any one of paragraphs 51-53, wherein the base comprises ammonium hydroxide, potassium hydroxide, sodium hydroxide, calcium hydroxide, magnesium hydroxide, strong base resins, sodium carbonate, potassium carbonate, lime, or any mixture thereof.

55. The process according to any one of paragraphs 1 to 54, wherein the fiber rich product comprises about at least 20 wt % of C5 polysaccharides and at least 20 wt % of C6 polysaccharides, based on a dried weight of the fiber rich product.

56. The process according to any one of paragraphs 1 to 54, wherein the fiber rich product comprises at least 23 wt % of C5 polysaccharides and at least 24 wt % of C6 polysaccharides, based on a dried weight of the fiber rich product.

57. The process according to any one of paragraphs 1 to 54, wherein the fiber rich product comprises about 23 wt % to about 34 wt % of C5 polysaccharides and about 25 wt % to about 35 wt % of C6 polysaccharides, based on a dried weight of the fiber rich product.

58. The process according to any one of paragraphs 1 to 54, wherein the fiber rich product comprises about 24 wt % to about 28 wt % of C5 polysaccharides and about 27 wt % to about 30 wt % of C6 polysaccharides, based on a dried weight of the fiber rich product.

59. The process according to any one of paragraphs 1 to 54, wherein the fiber rich product comprises about 38 wt % to about 45 wt % of C5 polysaccharides and about 28 wt % to about 33 wt % of C6 polysaccharides, based on a dried weight of the fiber rich product.

60. The process according to any one of paragraphs 1 to 54, wherein the fiber rich product comprises about 12 wt % to about 22 wt % of glucan, about 11 wt % to about 28 wt % of xylan, about 2.5 wt % to about 8 wt % of galactan, about 7 wt % to about 20 wt % of arabinan, and about 2 wt % to about 5 wt % of starch, based on the dried weight of the fiber product.

61. The process according to any one of paragraphs 1 to 54, wherein the fiber rich product comprises about 16 wt % to about 22 wt % of glucan, about 14 wt % to about 28 wt % of xylan, about 5 wt % to about 8 wt % of galactan, about 8 wt % to about 20 wt % of arabinan, and about 3.7 wt % to about 5 wt % of starch, based on the dried weight of the fiber products.

62. The process according to any one of paragraphs 1 to 54, wherein the fiber rich product comprises at least 16 wt % of glucan, at least 15 wt % of xylan, at least 5 wt % of galactan, at least 9 wt % of arabinan, and at least 2 wt % of starch, based on the dried weight of the fiber products.

63. The process according to any one of paragraphs 1 to 54, wherein the fiber rich product comprises at least 18 wt % of glucan, at least 16 wt % of xylan, at least 6 wt % of galactan, at least 9 wt % of arabinan, and at least 2 wt % of starch, based on the dried weight of the fiber products.

64. The process according to any one of paragraphs 1 to 54, wherein the fiber rich product comprises at least 20 wt % of glucan, at least 20 wt % of xylan, at least 6 wt % of galactan, at least 15 wt % of arabinan, and at least 2 wt % of starch, based on the dried weight of the fiber products.

65. The process according to any one of paragraphs 1 to 54, wherein the fiber rich product comprises less than 1 wt % of inorganic compounds, less than 1 wt % of extractives, about 1.5 wt % to about 3 wt % of acetate, about 28 wt % to about 33 wt % of C6 polysaccharides, and about 38 wt % to about 45 wt % of C5 polysaccharides, based on a dried weight of the fiber rich products.

66. The process according to any one of paragraphs 1 to 54, wherein the fiber rich product comprises less than 1 wt % of inorganic compounds, about 10 wt % to about 16 wt % of structural protein, less than 1 wt % of extractives, about 1.5 wt % to about 3 wt % of acetate, about 28 wt % to about 33 wt % of C6 polysaccharides, and about 38 wt % to about 45 wt % of C5 polysaccharides, based on a dried weight of the fiber rich products.

67. The process according to any one of paragraphs 1 to 54, wherein the fiber rich product comprises less than 1 wt % of inorganic compounds, about 10 wt % to about 16 wt % of structural protein, less than 1 wt % of extractives, about 1.5 wt % to about 3 wt % of acetate, about 17 wt % to about 22 wt % of lignin, about 28 wt % to about 33 wt % of C6 polysaccharides, and about 38 wt % to about 45 wt % of C5 polysaccharides, based on a dried weight of the fiber rich products.

68. The process according to any one of paragraphs 1 to 54, wherein the fiber rich product comprises less than 1 wt % of the inorganic compounds, less than 2 wt % of the extractives, about 1.8 wt % to about 4 wt % of acetate, about 27 wt % to about 30 wt % of C6 polysaccharides, and about 24 wt % to about 28 wt % of C5 polysaccharides, based on a dried weight of the fiber rich products.

69. The process according to any one of paragraphs 1 to 54, wherein the fiber rich product comprises less than 1 wt % of the inorganic compounds, about 20 wt % to about 26 wt % of structural protein, less than 2 wt % of the extractives, about 2 wt % to about 4 wt % of acetate, about 27 wt % to about 30 wt % of C6 polysaccharides, and about 24 wt % to about 28 wt % of C5 polysaccharides, based on a dried weight of the fiber rich products.

70. The process according to any one of paragraphs 1 to 54, wherein the fiber rich product comprises less than 1 wt % of the inorganic compounds, less than 2 wt % of the extractives, about 1.8 wt % to about 4 wt % of acetate, about 20 wt % to about 25 wt % of structural protein, about 17 wt % to about 22 wt % of lignin, about 27 wt % to about 30 wt % of C6 polysaccharides, and about 24 wt % to about 28 wt % of C5 polysaccharides, based on a dried weight of the fiber rich products.

71. The process according to any one of paragraphs 1, 2, 4, 6, 7, 10, 11, 13, and 15-70, wherein the whole stillage is separated with a fiber filter to produce the fiber rich product and the filtrate.

72. The process according to any one of paragraphs 3, 9, 12, and 16 to 71, wherein the fiber filter comprises a filter sleeve and a rotor disposed within the filter sleeve.

73. The process according to any one of paragraphs 3, 9, 12, and 16 to 71, wherein the fiber filter comprises a filter sleeve and a rotor disposed within the filter sleeve, and wherein the filter sleeve comprises a woven polymer fabric.

74. The process according to paragraph 72 or 73, wherein the filter sleeve has openings of 500 μm or less.

75. The process according to paragraph 72 or 73, wherein the filter sleeve has openings of about 10 μm to less than 400 μm.

76. The process according to paragraph 72 or 73, wherein the filter sleeve has openings of about 12 μm to about 200 μm.

77. The process according to any one of paragraphs 1 to 76, wherein at least 10 wt % of the ground corn product has a particle size of less than 100 μm, as measured according to AOAC 965.22-1966.

78. The process according to any one of paragraphs 1 to 76, wherein at least 15 wt % of the ground corn product has a particle size of less than 100 μm, as measured according to AOAC 965.22-1966.

79. The process according to any one of paragraphs 1 to 76, wherein at least 20 wt % of the ground corn product has a particle size of less than 100 μm, as measured according to AOAC 965.22-1966.

80. The process according to any one of paragraphs 1 to 76, wherein at least 25 wt % of the ground corn product has a particle size of less than 100 μm, as measured according to AOAC 965.22-1966.

81. The process according to any one of paragraphs 1 to 76, wherein at least 30 wt % of the ground corn product has a particle size of less than 100 μm, as measured according to AOAC 965.22-1966.

82. The process according to any one of paragraphs 1 to 76, wherein at least 35 wt % of the ground corn product has a particle size of less than 100 μm, as measured according to AOAC 965.22-1966.

83. The process according to any one of paragraphs 1 to 76, wherein at least 40 wt % of the ground corn product has a particle size of less than 100 μm, as measured according to AOAC 965.22-1966.

84. The process according to any one of paragraphs 1 to 83, wherein greater than 25 wt % of the ground corn product has a particle size of greater than 105 μm, as measured according to AOAC 965.22-1966.

85. The process according to any one of paragraphs 1 to 83, wherein greater than 30 wt % of the ground corn product has a particle size of greater than 105 μm, as measured according to AOAC 965.22-1966.

86. The process according to any one of paragraphs 1 to 83, wherein greater than 35 wt % of the ground corn product has a particle size of greater than 105 μm, as measured according to AOAC 965.22-1966.

87. The process according to any one of paragraphs 1 to 83, wherein greater than 40 wt % of the ground corn product has a particle size of greater than 105 μm, as measured according to AOAC 965.22-1966.

88. The process according to any one of paragraphs 1 to 83, wherein greater than 45 wt % of the ground corn product has a particle size of greater than 105 μm, as measured according to AOAC 965.22-1966.

89. The process according to any one of paragraphs 1 to 83, wherein greater than 50 wt % of the ground corn product has a particle size of greater than 105 μm, as measured according to AOAC 965.22-1966.

90. A fiber rich product having an ethanol potential of at least 90 gallons of ethanol per 1,000 kilograms of the fiber rich product, wherein the fiber rich product is separated from a fermentation mash produced by fermenting a ground corn product.

91. The fiber rich product according to paragraph 90, wherein the fiber rich product has an ethanol potential of at least 95 gallons of ethanol per 1,000 kilograms of the fiber rich product, wherein the fiber rich product is separated from a fermentation mash produced by fermenting a ground corn product.

92. The fiber rich product according to paragraph 90, wherein the fiber rich product has an ethanol potential of at least 100 gallons of ethanol per 1,000 kilograms of the fiber rich product, wherein the fiber rich product is separated from a fermentation mash produced by fermenting a ground corn product.

93. The fiber rich product according to paragraph 90, wherein the fiber rich product has an ethanol potential of at least 105 gallons of ethanol per 1,000 kilograms of the fiber rich product, wherein the fiber rich product is separated from a fermentation mash produced by fermenting a ground corn product.

94. The fiber rich product according to paragraph 90, wherein the fiber rich product has an ethanol potential of at least 110 gallons of ethanol per 1,000 kilograms of the fiber rich product, wherein the fiber rich product is separated from a fermentation mash produced by fermenting a ground corn product.

95. The fiber rich product according to paragraph 90, wherein the fiber rich product has an ethanol potential of at least 115 gallons of ethanol per 1,000 kilograms of the fiber rich product, wherein the fiber rich product is separated from a fermentation mash produced by fermenting a ground corn product.

96. The fiber rich product according to paragraph 90, wherein the fiber rich product has an ethanol potential of at least 120 gallons of ethanol per 1,000 kilograms of the fiber rich product, wherein the fiber rich product is separated from a fermentation mash produced by fermenting a ground corn product.

97. The fiber rich product according to paragraph 90, wherein the fiber rich product has an ethanol potential of at least 125 gallons of ethanol per 1,000 kilograms of the fiber rich product, wherein the fiber rich product is separated from a fermentation mash produced by fermenting a ground corn product.

98. The fiber rich product according to paragraph 90, wherein the fiber rich product has an ethanol potential of at least 130 gallons of ethanol per 1,000 kilograms of the fiber rich product, wherein the fiber rich product is separated from a fermentation mash produced by fermenting a ground corn product.

99. The fiber rich product according to paragraph 90, wherein the fiber rich product has an ethanol potential of at least 135 gallons of ethanol per 1,000 kilograms of the fiber rich product, wherein the fiber rich product is separated from a fermentation mash produced by fermenting a ground corn product.

100. The fiber rich product according to paragraph 90, wherein the fiber rich product has an ethanol potential of at least 140 gallons of ethanol per 1,000 kilograms of the fiber rich product, wherein the fiber rich product is separated from a fermentation mash produced by fermenting a ground corn product.

101. The fiber rich product according to any one of paragraphs 90 to 100, wherein the fiber rich product has an ethanol potential of up to about 145 gallons of ethanol per 1.000 kilograms of the fiber rich product, wherein the fiber rich product is separated from a fermentation mash produced by fermenting a ground corn product.

102. The fiber rich product according to any one of paragraphs 90 to 100, wherein the fiber rich product has an ethanol potential of up to about 150 gallons of ethanol per 1,000 kilograms of the fiber rich product, wherein the fiber rich product is separated from a fermentation mash produced by fermenting a ground corn product.

103. The fiber rich product according to any one of paragraphs 90 to 100, wherein the fiber rich product has an ethanol potential of up to about 155 gallons of ethanol per 1.000 kilograms of the fiber rich product, wherein the fiber rich product is separated from a fermentation mash produced by fermenting a ground corn product.

104. The fiber rich product according to any one of paragraphs 90 to 100, wherein the fiber rich product has an ethanol potential of up to about 160 gallons of ethanol per 1,000 kilograms of the fiber rich product, wherein the fiber rich product is separated from a fermentation mash produced by fermenting a ground corn product.

105. The fiber rich product according to any one of paragraphs 90 to 104, wherein greater than 80 wt % of the ground corn product has a particle size of 425 µm or less, as measured according to AOAC 965.22-1966.

106. The fiber rich product according to any one of paragraphs 90 to 105, wherein greater than 25 wt % of the ground corn product has a particle size of greater than 105 µm, as measured according to AOAC 965.22-1966.

107. The fiber rich product according to any one of paragraphs 90 to 106, wherein the ground corn product has a $d_{50}$ by volume percent of 100 µm to 400 µm, as measured according to ISO 13320:2009.

108. The fiber rich product according to any one of paragraphs 90 to 106, wherein greater than 85 wt % of the ground corn product has a particle size of 425 µm or less, as measured according to AOAC 965.22-1966, and wherein the ground corn product has a crystallinity of greater than 75%, as compared to a crystallinity of the corn pieces.

109. The fiber rich product according to any one of paragraphs 90 to 108, wherein the ground corn product is produced by grinding corn in an air swept pulverizer.

110. The fiber rich product according to any one of paragraphs 90 to 108, wherein the ground corn product is produced by grinding corn in a disk mill fiberizer.

111. A fiber rich product comprising at least 20 wt % of C5 polysaccharides and at least 20 wt % of C6 polysaccharides, based on a dried weight of the fiber rich product, wherein the fiber rich product is separated from a fermentation mash produced by fermenting a ground corn product.

112. The fiber rich product according to paragraph 111, wherein the fiber rich product comprises at least 23% of C5 polysaccharides and at least 24 wt % of C6 polysaccharides, based on a dried weight of the fiber rich product.

113. The fiber rich product according to paragraph 111 or 112, wherein the fiber rich product comprises up to about 45 wt % of C5 polysaccharides and up to about 35 wt % of C6 polysaccharides, based on a dried weight of the fiber rich product.

114. The fiber rich product according to paragraph 111, wherein the fiber rich product comprises about 24 wt % to about 28 wt % of C5 polysaccharides and about 27 wt % to about 30 wt % of C6 polysaccharides, based on a dried weight of the fiber rich product.

115. The fiber rich product according to paragraph 111, wherein the fiber rich product comprises about 38 wt % to about 45 wt % of C5 polysaccharides and about 28 wt % to about 33 wt % of C6 polysaccharides, based on a dried weight of the fiber rich product.

116. A fiber rich product, comprising about 12 wt % to about 22 wt % of glucan, about 11 wt % to about 28 wt % of xylan, about 2.5 wt % to about 8 wt % of galactan, about 7 wt % to about 20 wt % of arabinan, and about 2 wt % to about 5 wt % of starch, based on a dried weight of the fiber rich product, wherein the fiber rich product is separated from a fermentation mash produced by fermenting a ground corn product.

117. The fiber rich product according to paragraph 116, wherein the fiber rich product comprises about 16 wt % to about 22 wt % of glucan, about 14 wt % to about 28 wt % of xylan, about 5 wt % to about 8 wt % of galactan, about 8 wt % to about 20 wt % of arabinan, and about 3.7 wt % to about 5 wt % of starch, based on the dried weight of the fiber products.

118. The fiber rich product according to paragraph 116, wherein the fiber rich product comprises at least 16 wt % of glucan, at least 15 wt % of xylan, at least 5 wt % of galactan, at least 9 wt % of arabinan, and at least 2 wt % of starch, based on the dried weight of the fiber products.

119. The fiber rich product according to paragraph 116, wherein the fiber rich product comprises at least 18 wt % of glucan, at least 16 wt % of xylan, at least 6 wt % of galactan, at least 9 wt % of arabinan, and at least 2 wt % of starch, based on the dried weight of the fiber products.

120. The fiber rich product according to paragraph 116, wherein the fiber rich product comprises at least 20 wt % of glucan, at least 20 wt % of xylan, at least 6 wt % of galactan, at least 15 wt % of arabinan, and at least 2 wt % of starch, based on the dried weight of the fiber products.

121. The fiber rich product according to any one of paragraphs 111 to 120, wherein the fiber rich product comprises less than 1 wt % of inorganic compounds, less than 1 wt % of extractives, and about 1.5 wt % to about 3 wt % of acetate, based on a dried weight of the fiber rich products.

122. The fiber rich product according to any one of paragraphs 111 to 120, wherein the fiber rich product comprises less than 1 wt % of inorganic compounds, about 10 wt % to about 16 wt % of structural protein, less than 1 wt % of extractives, and about 1.5 wt % to about 3 wt % of acetate, based on a dried weight of the fiber rich products.

123. The fiber rich product according to any one of paragraphs 111 to 120, wherein the fiber rich product comprises less than 1 wt % of inorganic compounds, about 10 wt % to about 16 wt % of structural protein, less than 1 wt % of extractives, about 1.5 wt % to about 3 wt % of acetate, and about 17 wt % to about 22 wt % of lignin, based on a dried weight of the fiber rich products.

124. The fiber rich product according to any one of paragraphs 111 to 120, wherein the fiber rich product comprises less than 1 wt % of the inorganic compounds, less than 2 wt % of the extractives, and about 1.8 wt % to about 4 wt % of acetate, based on a dried weight of the fiber rich products.

125. The fiber rich product according to any one of paragraphs 111 to 120, wherein the fiber rich product comprises less than 1 wt % of the inorganic compounds, about 20 wt % to about 26 wt % of structural protein, less than 2 wt % of the extractives, and about 2 wt % to about 4 wt % of acetate, based on a dried weight of the fiber rich products.

126. The fiber rich product according to any one of paragraphs 111 to 120, wherein the fiber rich product comprises less than 1 wt % of the inorganic compounds, less than 2 wt % of the extractives, about 1.8 wt % to about 4 wt % of acetate, about 20 wt % to about 25 wt % of structural protein, and about 17 wt % to about 22 wt % of lignin, based on a dried weight of the fiber rich products.

127. A stillage protein product comprising about 40 wt % to about 80 wt % of protein, about 3 wt % to about 20 wt % of fat, about 1 wt % to about 4 wt % of ash, about 2 wt % to about 30 wt % of neutral detergent fibers, and about 1 wt % to about 15 wt % of acid detergent fibers, based on a dry weight of the stillage protein product.

128. A stillage protein product comprising about 40 wt % to about 80 wt % of protein, about 3 wt % to about 20 wt % of fat, about 1 wt % to about 4 wt % of ash, about 2 wt % to about 30 wt % of neutral detergent fibers, about 1 wt % to about 15 wt % of acid detergent fibers, and about 15 wt % to about 30 wt % of yeast, based on a dry weight of the stillage protein product.

129. The stillage protein product according to paragraphs 127 and 128, wherein the stillage protein product comprises about 20 wt % to about 30 wt % of yeast, based on a div weight of the stillage protein product.

130. The stillage protein product according to any one of paragraphs 127 to 129, wherein the stillage protein product comprises about 20 wt % to about 27 wt % of yeast, based on a dry weight of the stillage protein product.

131. The stillage protein product according to any one of paragraphs 127 to 130, wherein the stillage protein product comprises at least 20 wt % to about 30 wt % of yeast, based on a dry weight of the stillage protein product.

132. The stillage protein product according to any one of paragraphs 127 to 131, wherein the stillage protein product comprises about 40 wt % to about 80 wt % of protein, about 3 wt % to about 20 wt % of fat, about 1 wt % to about 4 wt % of ash, about 2 wt % to about 30 wt % of neutral detergent fibers, about 1 wt % to about 15 wt % of acid detergent fibers, and about 15 wt % to about 35 wt % of yeast, based on a dry weight of the stillage protein product.

133. The stillage protein product according to any one of paragraphs 127 to 132, wherein the stillage protein product comprises about 47 wt % to about 57 wt % of protein, about 3 wt % to about 5 wt % of fat, about 1 wt % to about 3 wt % of ash, about 4 wt % to about 10 wt % of neutral detergent fibers, about 5 wt % to about 10 wt % of acid detergent fibers, and about 20 wt % to about 30 wt % of yeast, based on a dry weight of the stillage protein product.

134. The stillage protein product according to any one of paragraphs 127 to 133, wherein the stillage protein product is produced by processing a fiber rich product separated from a whole stillage, wherein the whole stillage is separated from a fermentation mash produced by processing aground corn product.

135. The stillage protein product according to any one of paragraphs 127 to 133, wherein the stillage protein product is separated from a fermented saccharification mash, wherein the saccharification mash is produced by hydrolyzing a fiber rich product, and wherein the fiber rich product is separated from a whole stillage, and wherein the whole stillage is separated from a fermentation mash produced by processing a ground corn product.

136. A process for recovering products from a fermentation mash, comprising: separating ethanol from a fermentation mash to produce a whole stillage, wherein the fermentation mash is derived from aground corn product milled from a plurality of corn pieces, wherein the plurality of corn pieces comprises whole corn kernels, fragmented corn kernels, size-reduced corn kernels, milled corn kernels, or any mixture thereof, wherein greater than 80 wt % of the ground corn product has a particle size of 425 µm or less, as measured according to AOAC 965.22-1966; separating the whole stillage to produce a fiber rich product and a filtrate; hydrolyzing the fiber rich product to produce a saccharification mash; and processing the saccharification mash to produce additional ethanol and a stillage protein product.

137. The process according to paragraph 136, wherein the fiber rich product is contacted with an acid or a base prior to hydrolyzing the fiber rich product to produce the saccharification mash.

138. The process according to paragraph 136 and 137, wherein the fiber rich product has an ethanol potential of at least 90 gallons of ethanol per 1,000 kilograms of the fiber rich product.

139. The process according to any one of paragraphs 136 to 138, wherein the fiber rich product has an ethanol potential of about 100 gallons of ethanol per 1,000 kilograms of the fiber rich product to about 150 gallons of ethanol per 1,000 kilograms of the fiber rich product.

140. The process according to any one of paragraphs 136 to 139, wherein the fiber rich product has an ethanol potential of about 130 gallons of ethanol per 1,000 kilograms of the fiber rich product to about 150 gallons of ethanol per 1,000 kilograms of the fiber rich product.

141. The process according to any one of paragraphs 136 to 140, wherein greater than 25 wt % of the ground corn product has a particle size of greater than 105 µm, as measured according to AOAC 965.22-1966.

142. The process according to any one of paragraphs 136 to 137, wherein: greater than 25 wt % of the ground corn product has a particle size of greater than 105 µm, as measured according to AOAC 965.22-1966, the fiber rich product has an ethanol potential of at least 90 gallons of ethanol per 1,000 kilograms of the fiber rich product, the fiber rich product is contacted with an acid or a base to produce the pretreated fiber rich product, and the stillage protein product comprises about 40 wt % to about 80 wt % of protein, about 3 wt % to about 20 wt % of fat, about 1 wt % to about 4 wt % of ash, about 2 wt % to about 30 wt % of neutral detergent fibers, about 1 wt % to about 15 wt % of acid detergent fibers, and about 15 wt % to about 35 wt % of yeast, based on a dry weight of the stillage protein product.

143. The process, the fiber rich product, or the stillage protein product according to any one of paragraphs 1 to 142, wherein the ground corn product is produced by dry grinding.

144. The process, the fiber rich product, or the stillage protein product according to any one of paragraphs 1 to 143, wherein the ground corn product is milled from a plurality of corn pieces by one or more high shear mills.

145. The process, the fiber rich product, or the stillage protein product according to any one of paragraphs 1 to 144, wherein the ground corn product is milled from a plurality of corn pieces by one or more disk mill fiberizers.

146. The process, the fiber rich product, or the stillage protein product according to any one of paragraphs 1 to 145, wherein the ground corn product is milled from a plurality of corn pieces by one or more air swept pulverizers.

Certain embodiments and features have been described using a set of numerical upper limits and a set of numerical lower limits. It should be appreciated that ranges including the combination of any two values. e.g., the combination of any lower value with any upper value, the combination of any two lower values, and/or the combination of any two upper values are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. And if applicable, all patents, test procedures, and other documents cited in this application are fully incorporated by reference to the extent such disclosure is not inconsistent with this application and for all jurisdictions in which such incorporation is permitted.

While the foregoing is directed to certain illustrative embodiments, other and further embodiments of the invention can be devised without departing from the basic scope thereof, and the scope thereof is determined by the claims that follow.

What is claimed is:

1. A process for producing one or more fermentation products in a second fermentation, the process comprising:
    distilling a first fermentation mash to produce whole stillage;
    separating the whole stillage to produce a fiber rich product;
    producing a second fermentation mash from the fiber rich product via fermentation, wherein the second fermentation mash comprises one or more fermentation products.

2. The process of claim 1, wherein the one or more fermentation products comprise a stillage protein product.

3. The process of claim 1, wherein the second fermentation mash is produced via a strain of yeast chosen from Saccharomyces cerevisae, Pichia stipitis, Candida utilis, and combinations thereof.

4. The process of claim 1, wherein the second fermentation mash is produced via a strain of yeast comprising Candida utilis.

5. The process of claim 1, wherein the one or more fermentation products comprise an alcohol.

6. The process of claim 2, further comprising recovering stillage protein product from the second fermentation mash.

7. The process of claim 1, wherein producing a second fermentation mash comprises simultaneous saccharification and fermentation.

8. The process of claim 1, wherein producing the second fermentation mash comprises pretreating the fiber rich product to form a pretreated fiber rich product.

9. The process of claim 8, wherein one or more enzymes are added to pretreated fiber rich product to saccharify pretreated fiber rich product and form one or more sugars.

10. The process of claim 9, wherein the one or more enzymes are chosen from glucoamylase, one or more cellulases, one or more hemicellulases, and combinations thereof.

11. The process of claim 8, wherein the pretreated fiber rich product is exposed to saccharification conditions to form a saccharification mash followed by the fermenting the saccharification mash to produce the second fermentation mash.

12. The process of claim 1, wherein separating the whole stillage comprises separating whole stillage via one or more pressure screens, one or more centrifuges, one or more paddle screens, one or more fiber filters, one or more rotary drum screens, one or more rotary vacuum drum filters, one or more brush strainers, one or more vibratory separators, one or more centrifugal screeners, one or more linear motion screens, one or more vacu-deck screens, and combinations thereof.

13. The process of claim 1, wherein separating the whole stillage comprises separating whole stillage via one or more pressure screens, one or more filtration centrifuges, one or more paddle screens, and combinations thereof.

14. The process of claim 1, wherein separating the whole stillage produces a first stream comprising the fiber rich product and a second stream, and further comprising separating at least a portion of the second stream via a separator into at least a protein rich product and a clarified stillage.

15. The process of claim 14, wherein the separator comprises a two-phase, nozzle centrifuge.

16. The process of claim 14, further comprising removing water from the protein rich product via one or more centrifuges, one or more ring dryers, one or more flash dryers, one or more fluid bed dryers, one or more heated air dryers, one or more heaters, one or more steam dryers, one or more rotary dryers, one or more steam and rotary dryers, one or more superheated steam dryers, one or more spray dryers, one or more vacuum filtration dryers, and combinations thereof.

17. The process of claim 14, further comprising removing water from the protein rich product via one or more decanter centrifuges and one or more dryers to produce a dried protein product.

18. The process of claim 14, further comprising drying the protein rich product via one or more dryers to produce a dried protein product.

19. The process of claim 14, wherein separating at least a portion of the second stream via a separator comprises supplying wash water and the second stream to the separator to produce at least the protein rich product and the clarified stillage.

20. The process of claim 1, wherein the first fermentation mash is derived from fermenting a slurry to produce ethanol, wherein the slurry comprises water, ground corn, and one or more enzymes.

* * * * *